(12) United States Patent
Basford et al.

(10) Patent No.: US 6,855,724 B2
(45) Date of Patent: Feb. 15, 2005

(54) TROPANE DERIVATIVES USEFUL IN THERAPY

(75) Inventors: Patricia Ann Basford, Sandwich (GB); Peter Thomas Stephenson, Sandwich (GB); Stefan Colin John Taylor, Sandwich (GB); Anthony Wood, Sandwich (GB)

(73) Assignee: Agouron Pharmaceuticals, Inc., San Diego, CA (US)

( * ) Notice: Subject to any disclaimer, the term of this patent is extended or adjusted under 35 U.S.C. 154(b) by 0 days.

(21) Appl. No.: 10/408,856

(22) Filed: Apr. 7, 2003

(65) Prior Publication Data

US 2004/0014742 A1 Jan. 22, 2004

Related U.S. Application Data

(60) Provisional application No. 60/386,670, filed on Jun. 4, 2002, and provisional application No. 60/449,064, filed on Feb. 20, 2003.

(30) Foreign Application Priority Data

Apr. 8, 2002 (GB) .............................................. 0208071
Jan. 23, 2003 (GB) .............................................. 0301575

(51) Int. Cl.$^7$ ...................... A61K 31/46; A61K 31/437; C07D 471/04; C07D 451/04; A61P 31/18
(52) U.S. Cl. .................. 514/303; 514/304; 514/217.07; 514/228.5; 514/234.5; 514/253.04; 546/118; 546/126; 544/60; 544/362; 544/127; 540/597
(58) Field of Search ................................ 546/118, 126; 514/303, 304

(56) References Cited

FOREIGN PATENT DOCUMENTS

| EP | 1118 858 A2 | 7/2001 |
|---|---|---|
| GB | 0208071.1 | 4/2002 |
| GB | 0301575.7 | 1/2003 |
| WO | WO 91/11172 | 8/1991 |
| WO | WO 94/02518 | 2/1994 |
| WO | WO 98/55148 | 12/1998 |
| WO | WO 99/31099 | 6/1999 |
| WO | WO 00/38680 | 7/2000 |
| WO | WO 00/39125 | 7/2000 |
| WO | WO 01/90106 | 11/2001 |

OTHER PUBLICATIONS

Hesselgesser et al., J. Biol. Chem. 1998, 273(25): 15687–15692.*
U.S. Appl. No. 60/386,670, filed Jun. 4, 2002, Pfizer Limited.
U.S. Appl. No. 60/449,064, filed Feb. 20, 2003, Pfizer Limited.
Berge, et. al., "Pharmaceutical Salts," Journal of Pharmaceutical Sciences, 1977, 1–19, vol. 66, No. 1.
Bungaard, H. "Design of Prodrugs", Elsevier Press., 1985, Amsterdam, New York, Oxford.
Cascieri, M., et. al., "The Chemokine/Chemokine Receptor Family: Potential and Progess for Therapeutic Intervention," Current Opinion in Chemical Biology, 2000, 4:420–427, vol. 4, No. 4.
Combadiere, et. al., "Cloning and Functional Expression of CC CKR5, a Human Monocyte CC Chemokine Receptor Selective for MIP-α, MIP-1β, and RANTES," Journal of Leukocyte Biology, 1996, 147–152, vol. 60.
Connor, et. al., "Vpr is Required for Efficient Replication of Human Immunodeficiency Virus Type–1 in Mononuclear Phagocytes," Virology, 1995, 935–944, vol. 206.
Demitrov, et. al., "Microculture Assay for Isolation of Human Immunodeficiency Virus Type 1 and for Titration of Infected Peripheral Blood Mononuclear Cells," Journal of Clinical Microbiology, 1990, 734–737, vol. 28, No. 4.
Greene, T., et. al., "Protection for the Amino Group," Protective Groups in Organic Synthesis, 3$^{rd}$ edition, John Wiley and Sons, 1999, 494–653.
March, Advanced Organic Chemistry, 4$^{th}$ edition, John Wiley and Sons, 1992, 652.

* cited by examiner

Primary Examiner—Evelyn Mei Huang
(74) Attorney, Agent, or Firm—Peter C. Richardson; Bryan C. Zielinski; Keith D. Hutchinson

(57) ABSTRACT

The present invention provides compounds of formula (I)

(I)

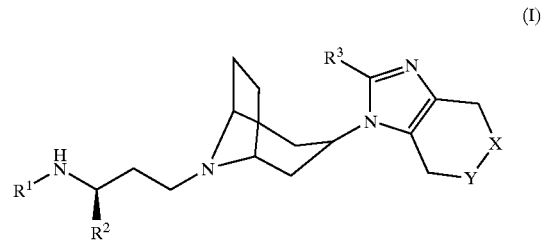

wherein X, Y, R$^1$, R$^2$ and R$^3$ are as defined hereinabove.

The compounds of the present invention are modulators, especially antagonists, of the activity of chemokine CCR5 receptors. Modulators of the CCR5 receptor may be useful in the treatment of various inflammatory diseases and conditions, and in the treatment of infection by HIV and genetically related retroviruses.

20 Claims, No Drawings

US 6,855,724 B2

TROPANE DERIVATIVES USEFUL IN THERAPY

This application claims priority from United Kingdom application number 0208071.1 filed Apr. 8, 2002, United Kingdom application number 0301575.7 filed Jan. 23, 2003, U.S. Provisional application No. 60/386,670 filed Jun. 4, 2002, and U.S. Provisional application No. 60/449,064 filed Feb. 20, 2003 and incorporates each application by reference in its entirety.

FIELD OF INVENTION

This invention relates to tropane derivatives, to processes for their preparation, to compositions containing them and to their use.

More particularly, the present invention relates to the use of 8-azabicyclo[3.2.1]octane derivatives in the treatment of a variety of disorders, including those in which the modulation of chemokine CCR5 receptors is implicated. Accordingly, compounds of the invention are useful in the treatment of HIV, such as HIV-1, and genetically related retroviral infections (and the resulting acquired immune deficiency syndrome, AIDS), and inflammatory diseases.

The name "chemokine", is a contraction of "chemotactic cytokines". The chemokines comprise a large family of proteins which have in common important structural features and which have the ability to attract leukocytes. As leukocyte chemotactic factors, chemokines play an indispensable role in the attraction of leukocytes to various tissues of the body, a process which is essential for both inflammation and the body's response to infection. Because chemokines and their receptors are central to the pathophysiology of inflammatory and infectious diseases, agents which are active in modulating, preferably antagonizing, the activity of chemokines and their receptors, are useful in the therapeutic treatment of such inflammatory and infectious diseases.

The chemokine receptor CCR5 is of particular importance in the context of treating inflammatory and infectious diseases. CCR5 is a receptor for chemokines, especially for the macrophage inflammatory proteins (MIP) designated MIP-1α and MIP-1β, and for a protein which is regulated upon activation and is normal T-cell expressed and secreted (RANTES).

According to a first aspect of the present invention, there is provided a compound of formula (I)

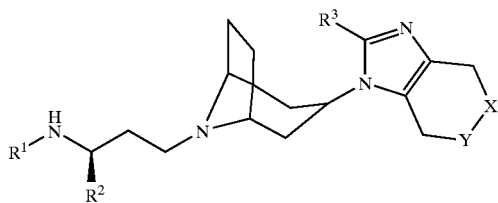

(I)

or a pharmaceutically acceptable salt, solvate of derivative thereof, wherein:

X and Y are selected from $CH_2$ and $NR^4$ such that one of X and Y is $CH_2$ and the other is $NR^4$;

$R^1$ and $R^4$ are independently $R^5$; $COR^5$; $CO_2R^5$; $CONR^6R^7$; $SO_2R^5$; or ($C_{1-6}$ alkylene)phenyl, wherein phenyl is substituted by 0 to 3 atoms or groups selected from $C_{1-6}$ alkyl, $C_{1-6}$ alkylcarbonyl, $C_{1-6}$ alkoxy, $C_{1-6}$ alkoxycarbonyl, halogen, $CF_3$, OH, CN, $NR^6R^7$, $COR^7$, $CO_2R^7$ or $CONR^6R^7$;

$R^2$ is phenyl substituted by 0 to 3 atoms or groups selected from $C_{1-6}$ alkyl, $C_{1-6}$ alkylcarbonyl, $C_{1-6}$ alkoxy, $C_{1-6}$ alkoxycarbonyl, halogen, $CF_3$, OH, CN, $NR^6R^7$, $CO_2R^7$ or $CONR^6R^7$;

$R^3$ is $C_{1-4}$ alkyl substituted by 0 to 3 fluorine atoms;

$R^5$ is $C_{1-6}$ alkyl; $C_{2-6}$ alkenyl; $C_{2-6}$ alkynyl; $C_{3-7}$ cycloalkyl; a 5 or 6-membered aromatic heterocycle; or a 4 to 7-membered saturated heterocycle; wherein said alkyl, alkenyl, alkynyl and cycloalkyl are substituted by 0 to 3 atoms or groups selected from oxo, halogen, $CF_3$, $OR^7$, CN, $NR^6R^7$, $COR^7$, $CO_2R^7$ or $CONR^6R^7$; wherein said heterocylces contain one to three heteroatoms selected from N, O or S; and wherein said heterocylces are substituted by 0 to 3 atoms or groups selected from $C_{1-6}$ alkyl, $C_{1-6}$ alkylcarbonyl, $C_{1-6}$ alkoxy, $C_{1-6}$ alkoxycarbonyl, halogen, $CF_3$, OH, CN, $NR^6R^7$, $COR^7$, $CO_2R^7$ or $CONR^6R^7$;

$R^6$ is H or $R^5$;

$R^7$ is H or $C_{1-6}$ alkyl;

or, when $R^6$ and $R^7$ are both attached to the same N atom, $NR^6R^7$ may also represent a 5 to 7 membered, saturated, partially unsaturated or aromatic, heterocycle containing from 0 to 2 additional heteroatoms selected from O, N or S.

In one aspect of the invention X is $CH_2$, NH, $NC_{1-4}$ alkyl, $NCH_2$phenyl, $NCOC_{1-4}$ alkyl substituted by 0 to 3 fluorine atoms, $NCO_2C_{1-4}$ alkyl or $NSO_2C_{1-2}$ alkyl.

In another aspect of the invention X is $CH_2$, $NCOC_{1-2}$ alkyl substituted by 0 or 3 fluorine atoms, or $NCO_2C_{1-4}$ alkyl.

In another aspect of the invention X is $CH_2$, $NCOC_{1-2}$ alkyl or $NCO_2C_{1-2}$ alkyl.

In another aspect of the invention Y is $CH_2$, NH, $NC_{1-6}$ alkyl, $N(C_{1-6}$ alkylene)phenyl, $NCOC_{1-6}$ alkyl substituted by 0 to 3 fluorine atoms, $NCO_2C_{1-6}$ alkyl or $NSO_2C_{1-6}$ alkyl.

In another aspect of the invention Y is $CH_2$, NH, $NC_{1-4}$ alkyl, $N(C_{1-4}$ alkylene)phenyl, $NCOC_{1-4}$ alkyl substituted by 0 to 3 fluorine atoms, $NCO_2C_{1-4}$ alkyl or $NSO_2C_{1-4}$ alkyl.

In another aspect of the invention Y is $CH_2$, NH, $NCOC_{1-4}$ alkyl, $NCH_2$phenyl, $NCOC_{1-4}$ alkyl substituted by 0 or 3 fluorine atoms, $NCO_2C_{1-4}$ alkyl or $NSO_2C_{1-2}$ alkyl.

In another aspect of the invention Y is $CH_2$, $NCOC_{1-2}$ alkyl, or $NCO_2C_{1-2}$ alkyl.

In one aspect of the invention $R^1$ is $COR^5$ or $CO_2R^5$ and $R^5$ is, $C_{1-6}$ alkyl substituted by 0 to 3 fluorine atoms, $C_{3-7}$ cycloalkyl substituted by 0 to 3 fluorine atoms, $C_{1-6}$ alkoxy substituted by 0 to 3 fluorine atoms, or a 4 to 7-membered saturated heterocycle containing 1 to 3 heteroatoms selected from N, O or S.

In another aspect of the invention $R^1$ is $COR^5$ or $CO_2R^5$, wherein $R^5$ is $C_{1-4}$ alkyl substituted by 0 to 3 fluorine atoms, $C_{3-5}$ cycloalkyl substituted by 0 to 3 fluorine atoms, or a 5 or 6-membered, N, O or S containing, saturated heterocycle.

In another aspect of the invention $R^1$ is $COR^5$ or $CO_2R^5$ and $R^5$ is $C_{1-3}$ alkyl substituted by 0 or 3 fluorine atoms, $C_{3-4}$ cycloalkyl, or a 5 or 6-membered, O-containing, saturated heterocycle.

In another aspect of the invention $R^1$ is $COC_{1-2}$ alkyl or $CO_2C_{1-2}$ alkyl.

In another aspect of the invention $R^2$ is phenyl substituted by 0 to 3 fluorine atoms.

In another aspect of the invention $R^2$ is phenyl substituted by 0 or 1 fluorine atoms.

In another aspect of the invention $R^2$ is unsubstituted phenyl.

In another aspect of the invention $R^2$ is mono-fluoro-substituted (e.g. meta substituted) phenyl.

In another aspect of the invention $R^3$ is $C_{1-4}$ alkyl.

In another aspect of the invention $R^3$ is methyl.

The term "alkyl" as a group or part of a group includes straight chain and branched groups. Examples of alkyl include methyl, ethyl, n-propyl, i-propyl, n-butyl, i-butyl, sec-butyl and t-butyl. The term "$C_{3-7}$ cycloalkyl" means cyclopropyl, cyclobutyl, cyclopentyl, cyclohexyl or cycloheptyl. The term halogen means fluoro, chloro, bromo or iodo.

It is to be understood that the invention covers all combinations of particular aspects of the invention as described hereinabove, consistent with the definition of compounds of formula (I).

The compounds of formula (I) contain at least two basic centres and suitable acid addition salts are formed from acids which form non-toxic salts. Examples include the hydrochloride, hydrobromide, hydroiodide, chloride, bromide, iodide, sulphate, bisulphate, nitrate, phosphate, hydrogen phosphate, acetate, fumarate, pamoate, aspartate, besylate, carbonate, bicarbonate, camsylate, D and L-lactate, D and L-tartrate, esylate, mesylate, malonate, orotate, gluceptate, methylsulphate, stearate, glucuronate, 2-napsylate, tosylate, hibenzate, nicotinate, isethionate, malate, maleate, citrate, gluconate, succinate, saccharate, benzoate, esylate, and pamoate salts. For a review on suitable salts see Berge et al, J. Pharm. Sci., 66, 1–19, 1977.

The pharmaceutically acceptable solvates of the compounds of formula (I) or salts or derivatives thereof include the hydrates thereof.

The compounds of formula (I) may be modified to provide pharmaceutically acceptable derivatives thereof at any of the functional groups in the compounds. It will be appreciated by those skilled in the art that certain protected derivatives of compounds of formula (I), which may be made prior to a final deprotection stage, may not possess pharmacological activity as such, but may, in certain instances, be transformed after administration into or onto the body, for example by metabolism, to form compounds of formula (I) which are pharmacologically active. Such derivatives are included in the term "prodrug". It will further be appreciated by those skilled in the art that certain moieties known to those skilled in the art as "pro-moieties", for example as described in "Design of Prodrugs" by H Bundgaard (Elsevier) 1985, may be placed on appropriate functionalities in compounds of formula (I), also to form a "prodrug". Further, certain compounds of formula (I) may act as prodrugs of other compounds of formula (I). By pharmaceutically acceptable derivatives of a compound of formula (I) is meant all protected derivatives, and prodrugs, of the compounds of formula (I).

Also included within the present scope of the compounds of formula (I) are polymorphs thereof.

It will be appreciated by the skilled artisan that the compounds of formula (I) may contain an additional chiral centre and therefore exist in two or more stereoisomeric forms. It will be further appreciated by the skilled artisan that imidazole substitution of the tropane ring can be in either endo- or exo-configuration, and it is to be understood that the present invention covers both configurations. The present invention includes all the individual stereoisomers (e.g. enantiomers) of the compounds of formula (I) and, where appropriate, the individual tautomeric forms thereof, together with mixtures (e.g. racemic mixtures) thereof.

Imidazole substitution of the tropane ring in the endo-configuration is preferred.

Separation of diastereoisomers may be achieved by conventional techniques, e.g. by fractional crystallisation, chromatography or H.P.L.C. of a stereoisomeric mixture of a compound of formula (I) or a suitable salt or derivative thereof. An individual enantiomer of a compound of formula (I) may also be prepared from a corresponding optically pure intermediate or by resolution, such as by H.P.L.C. of the corresponding racemate using a suitable chiral support or by fractional crystallisation of the diastereoisomeric salts formed by reaction of the corresponding racemate with a suitable optically active acid or base, as appropriate. Alternatively, an individual enantiomer of a compound of formula (I) may be prepared by employing chiral reagents, such as chiral catalysts.

The invention also includes isotopically labelled compounds of formula (I). An isotopic variation of a compound of the formula (I) or a pharmaceutically acceptable salt, solvate or derivative thereof is defined as one in which at least one atom is replaced by an atom having the same atomic number but an atomic mass different from the atomic mass usually found in nature. Examples of isotopes that can be incorporated into compounds of the formula (I) and pharmaceutically acceptable salts, solvates and derivatives thereof include isotopes of hydrogen, carbon, nitrogen, oxygen, phosphorus, sulphur, fluorine and chlorine such as $^2H$, $^3H$, $^{13}C$, $^{14}C$, $^{15}N$, $^{17}O$, $^{18}O$, $^{31}P$, $^{32}P$, $^{35}S$, $^{18}F$ and $^{36}Cl$, respectively. Certain isotopic variations of the compounds of the formula (I) and pharmaceutically acceptable salts, solvates and derivatives thereof, for example, those in which a radioactive isotope such as $^3H$ or $^{14}C$ is incorporated, are useful in drug and/or substrate tissue distribution studies. Tritiated, i.e., $^3H$, and carbon-14, i.e., $^{14}C$, isotopes are particularly preferred for their ease of preparation and detectability. Further, substitution with isotopes such as deuterium, i.e., $^2H$, may afford certain therapeutic advantages resulting from greater metabolic stability, for example, increased in vivo half-life or reduced dosage requirements and hence may be preferred in some circumstances. Isotopic variations of the compounds of formula (I) and pharmaceutically acceptable salts, solvates and derivatives thereof of this invention can be prepared by appropriate adaptation of the general methods discussed hereinafter and the processes illustrated by the Preparations and Examples that follow.

Preferred compounds of formula (I) include the compounds of Examples 7, 13, 17, 27, 29, 33, 34, 35, 36, 37, 39, 41, 44/45, 46, 49; and pharmaceutically acceptable salts, solvates or derivatives thereof.

Compounds of formula (I) and pharmaceutically acceptable salts, solvates and derivatives thereof and intermediates thereto may be prepared by any method known in the art for the preparation of compounds of analogous structure, such as the methods described in WO00/38680 and WO01/90106, both publications incorporated herein by reference. In particular, the reaction conditions described in WO01/90106 for the preparation of compounds of formula (I) from compounds of formulae (XIV), (XIX) and (XXIV) therein, are suitable for use in, respectively, processes, (G), (K) and (L) herein.

In the general processes, and schemes, that follow: $R^1$ to $R^7$, X and Y are as previously defined unless otherwise stated; $R^8$ and $R^{8a}$ in formula (III.2), process (B), are such that the group

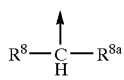

defines the desired $R^5$ substituent, wherein the arrow indicates the point of attachment to the compound of formula (II); Z is H, or a carboxylic acid activating group such as chloro or 1H-imidazol-1-yl; EsGp is an ester-forming group, such as $C_{1-6}$ alkyl; Pg is an amino protecting group, such as boc; ArLg is a leaving group appropriate to aromatic nucleophilic substitution, such as those disclosed in Jerry March, Advanced Organic Chemistry (4th edition), Wiley Interscience, 1992, page 652 (incorporated herein by reference), e.g. F, Cl, Br, OMe or OEt; boc is t-butoxycarbonyl; DMF is N,N-dimethylformamide; DCM is dichloromethane;. THF is tetrahydrofuran; Lg is a leaving group appropriate to aliphatic nucleophilic substitution, such as those disclosed in Jerry March, ibid, page 352 (incorporated herein by reference), including Cl, Br, I and sulfonic esters (e.g. tosylate, mesylate and triflate); WSCDI is 1-(3-dimethylaminopropyl)-3-ethylcarbodiimide hydrochloride; DCC is N,N'-dicyclohexylcarbodiimide; HOAT is 1-hydroxy-7-azabenzotriazole; HOBt is 1-hydroxybenzotriazole hydrate; PyBOP® is benzotriazol-1-yloxytris(pyrrolidino)phosphonium hexafluorophosphate; PyBrOP is bromo-tris-pyrrolidino-phosphonium hexafluorophosphate; and Mukaiyama's reagent is 2-chloro-1-methylpyridinium iodide.

Compounds of formula (I) may be prepared by the following general processes.

According to a first process (A) compounds of formula (I) wherein $R^1$ is $R^5$ may be prepared by alkylating a compound of formula (II)

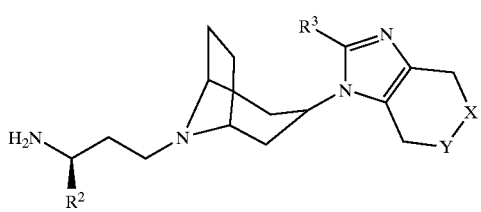

with a compound of formula (III.1), $R^5Lg$ (III.1), under conventional alkylating conditions. Conveniently, alkylation is effected under the conditions described hereinafter in connection with scheme 1, step (i).

According to a second process (B) compounds of formula (I) wherein $R^1$ is $R^5$ may be prepared by reacting a compound of formula (II) with a compound of formula (III.2), $R^8R^{8a}C=O$ (III.2), under conventional conditions of reductive amination. Conveniently, reductive amination is effected under the conditions described hereinafter in connection with scheme 1, step (g).

According to a third process (C) compounds of formula (I) wherein $R^1$ is $COR^5$ may be prepared by reacting a compound of formula (II) with a compound of formula (III.3):

under conventional carboxylic acid/amine coupling conditions. Conveniently, the coupling is effected under the conditions described hereinafter in connection with scheme 1, step (k).

According to a fourth process (D) compounds of formula (I) wherein $R^1$ is $CO_2R^5$ may be prepared by reacting a compound of formula (II) with a haloformate of formula (III.4)

under conventional coupling conditions. Conveniently, the reaction is effected under the conditions described hereinafter in connection with scheme 1 for the preparation of compounds of formula (IV) wherein $R^4$ is $CO_2R^5$.

According to a fifth process (E) compounds of formula (I) wherein $R^1$ is $CONR^6R^7$ may be prepared by reacting an amine of formula (II) with an acylimidazolide of formula (III.5)

under conventional conditions. Conveniently, the reaction is effected under the conditions described hereinafter in connection with scheme 1 for the preparation of compounds of formula (IV) wherein $R^4$ is $CONR^6R^7$.

According to a sixth process (F) compounds of formula (I) wherein $R^1$ is $SO_2R^5$ may be prepared by reacting a compound of formula (II) with a sulphonylhalide of formula (III.6)

under conventional conditions. Conveniently, the reaction is effected under the conditions described hereinafter in connection with scheme 1 for the preparation of compounds of formula (IV) wherein $R^4$ is $SO_2R^6$.

According to another process (G) compounds of formula (I) may be prepared by reduction of a compound of formula (XVII)

(XVII)

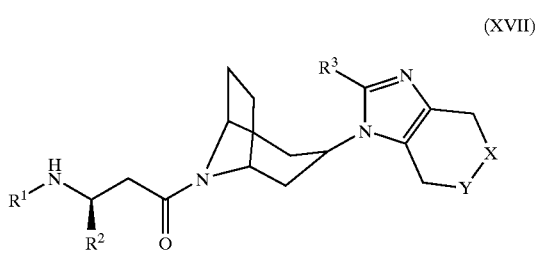

under conventional reduction conditions.

According to another process (H) compounds of formula (I) may be prepared by reductive amination of an aldehyde of formula (XVIII)

(XVIII)

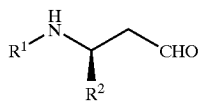

with an amine of formula (XIX)

(XIX)

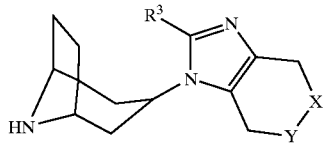

under conventional conditions. Conveniently, reductive amination is effected under the conditions described hereinafter in connection with scheme 1, step (g).

According to another process (I) compounds of formula (I) may be prepared by reductive amination of a nitrile of formula (XX)

(XX)

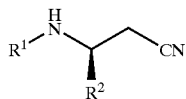

with an amine of formula (XIX) under conventional conditions. Conveniently, reductive amination is effected under the conditions described hereinafter in connection with scheme 1, step (g).

According to another process (J) compounds of formula (I) may be prepared by alkylation of an amine of formula (XIX) or a salt thereof with a compound of formula (XXI)

(XXI)

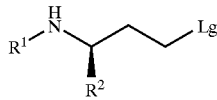

under conventional conditions. Conveniently, alkylation is effected under the conditions described hereinafter in connection with scheme 1, step (i).

According to another process (K) compounds of formula (I) may be prepared by asymmetric reduction of a compound of formula (XXII)

(XXII)

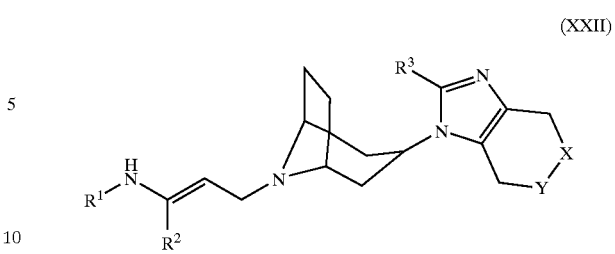

under conventional reduction conditions.

According to another process (L) compounds of formula (I) wherein $R^1$ is $COR^5$ may be prepared from the amine of the formula (II), or a metal salt thereof (i.e. a deprotonated form), by reaction with an ester of the formula (XXIII)

$$R^5CO_2EsGp \qquad (XXIII)$$

under conventional conditions.

According to another process (M) compounds of formula (I) may be prepared by interconversion from another compound of formula (I). Suitable interconversions include the preparation of compounds of formula (I) wherein X or Y is $NR^5$ from the corresponding compound of formula (I) wherein X or, respectively, Y, is NH. The skilled artisan will appreciate that such interconversion can be readily carried out according to methods directly analogous to those described above under processes (A) to (F), and (L).

According to another process (N) compounds of formula (I) may be prepared by deprotection of a protected derivative of a compound of formula (I).

Schemes that further illustrate general methods for the preparation of compounds of formula (I), and intermediates thereto, follow.

It will be appreciated by those skilled in the art that certain of the procedures described in the schemes for the preparation of compounds of formula (I) or intermediates thereto may not be applicable to some of the possible substituents.

It will be further appreciated by those skilled in the art that it may be necessary or desirable to carry out the transformations described in the schemes in a different order from that described, or to modify one or more of the transformations, to provide the desired compound of formula (I).

It will be still further appreciated by those skilled in the art that, as illustrated in the schemes that follow, it may be necessary or desirable at any stage in the synthesis of compounds of formula (I) to protect one or more sensitive groups in the molecule so as to prevent undesirable side reactions. In particular, it may be necessary or desirable to protect amino groups. The protecting groups used in the preparation of compounds of formula (I) may be used in conventional manner. See, for example, those described in 'Protective Groups in Organic Synthesis' by Theodora W Green and Peter G M Wuts, third edition, (John Wiley and Sons, 1999), in particular chapter 7, pages 494–653 ("Protection for the Amino Group"), incorporated herein by reference, which also describes methods for the removal of such groups.

The amino protecting groups boc, benzyloxycarbonyl, benzyl and acetyl are of particular use in the preparation of compounds of formula (I) and intermediates thereto.

Scheme 1

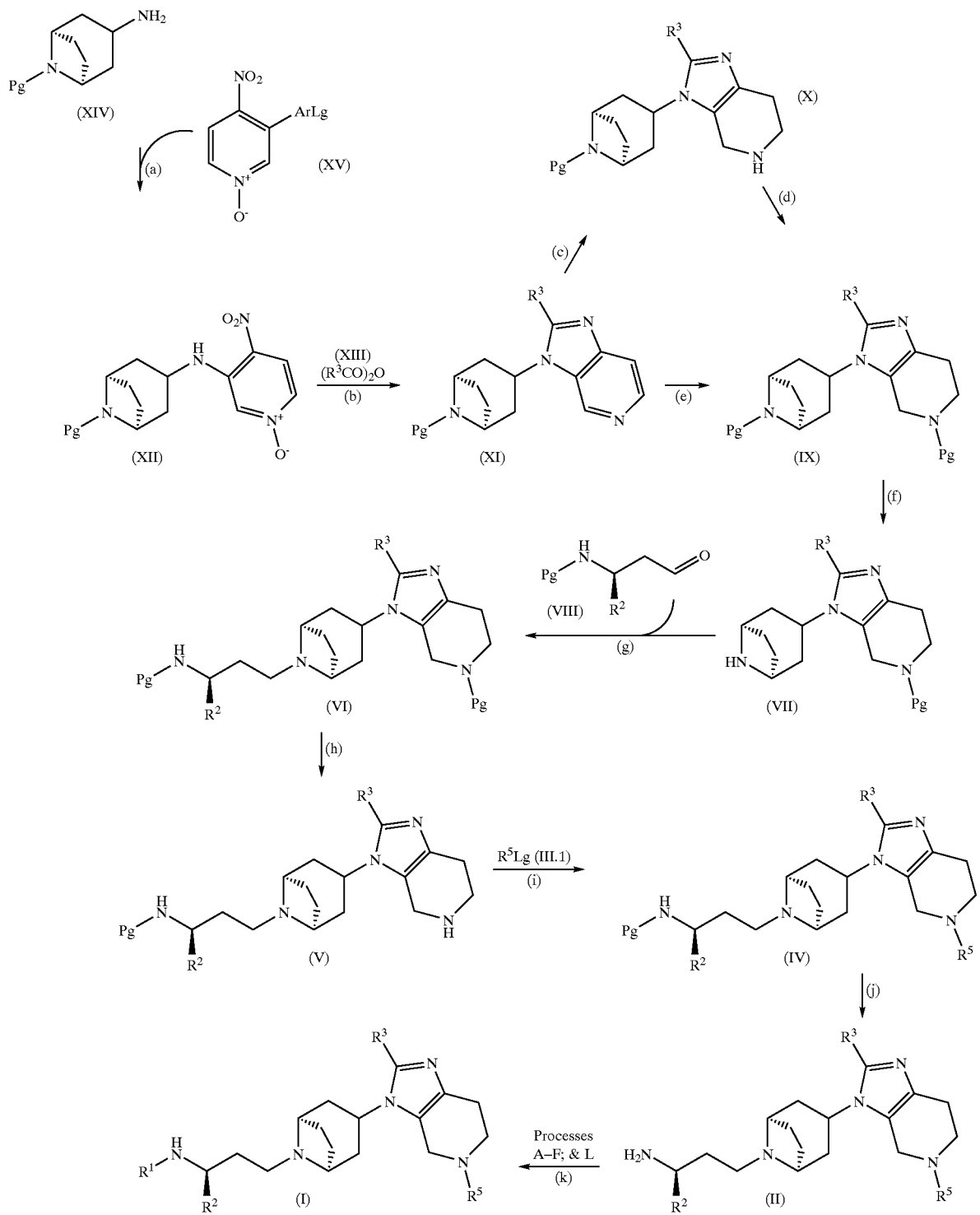

With specific reference to scheme 1, the transformations depicted therein may be effected as follows:

(a) Substitution of a leaving group on a nitropyridine of formula (XV) with an amine of formula (XIV) is conveniently effected in the presence of a base, such as an amine (e.g. triethylamine or N-ethyl-N,N-diisopropylamine) or an alkali metal carbonate (e.g. sodium carbonate or potassium carbonate); in a solvent, such as an alcohol (e.g. methanol or ethanol), a nitrile (e.g. acetonitrile) or an amide (e.g. DMF); and at from ambient to elevated temperature (e.g. up to about 120° C.).

(b) An imidazopyridine of formula (XI) may be prepared by reduction and in situ cyclisation of an amino-nitropyridine of formula (XII). The reduction is conveniently effected in the presence of a reducing agent, such as iron powder; a solvent, such as a carboxylic acid (e.g. acetic acid); and at from ambient temperature up to about 120° C. Cyclisation of the intermediate amino-aminopyridine is conveniently effected by the addition of an anhydride of formula (XIII) and at elevated temperature (e.g. about 140° C.).

(c) Reduction of an imidazopyridine of formula (XI) to an imidazopiperidine of formula (X) is conveniently effected by catalytic hydrogenation in the presence of a suitable catalyst, such as a transition metal catalyst, for instance a platinum (e.g. platinum oxide) or a palladium (e.g. palladium hydroxide or palladium on carbon) catalyst; in a solvent, such as a an alcohol (e.g. methanol or ethanol) or a carboxylic acid (e.g. acetic acid); at ambient to elevated temperature (e.g. up to 80° C.; and at elevated pressure, such as from 150 to 500 kPa of hydrogen (e.g. 400 kPa hydrogen)

(d) The imidazopiperidine of formula (X) may be protected by reaction with a benzyl halide, such as benzyl bromide or benzyl chloride. The reaction is conveniently carried out in a solvent, such as an alcohol (e.g. ethanol) or a haloalkane (e.g. DCM), and at room temperature.

(e) In an alternative to steps (c) and (d), an imidazopyridine of formula (XI) is treated with a benzyl halide, such as benzyl bromide, to give a quaternary intermediate, which is reduced under conventional conditions. Conveniently, benzyl bromide is added to an imidazopyridine of formula (XI) in the presence of a solvent, such as an alcohol (e.g. ethanol) or a haloalkane (e.g. DCM) and at ambient temperature to give a quaternary intermediate, which is then reduced by the addition of an alkali metal halide, such as sodium borohydride, under conditions of reduced temperature (e.g. about −70° C.).

(f) Where the protecting group is an acetyl protecting group or like group, its removal is conveniently effected by treatment with a base, such as an alkali metal hydroxide (e.g. sodium or potassium hydroxide) or an acid, such as an inorganic acid (e.g. hydrochloric acid) and at elevated temperature, such as from 60–100° C.

(g) Compounds of formula (VI) are prepared by reductive amination of an aldehyde of formula (VIII) by an amine of formula (VII). Conveniently, the reaction is carried out in the presence of an acid, such as an organic acid (e.g. acetic acid); in a solvent, such as an ether (e.g. THF) or a haloalkane (e.g. DCM); using an alkali metal hydride reducing agent, such as sodium triacetoxyborohydride, sodium cyanoborohydride or sodium borohydride; and at ambient temperature.

(h) Where protection under step (d) is afforded by means of a benzyl group, its removal is conveniently effected by transfer hydrogenation using a suitable source of hydrogen, such as ammonium formate, over a transition metal catalyst, such as a palladium catalyst (e.g. palladium on carbon or palladium hydroxide on carbon), in a solvent, such as an alcohol (e.g. ethanol) and at elevated temperature, such as about 60° C.

(i) When $R^4$ is $R^5$, compounds of formula (IV) are prepared from amines of formula (V) by alkylation with a compound of formula (III.1). Conveniently, alkylation is effected in a suitable solvent such as a haloalkane (e.g. DCM), alcohol (e.g. ethanol) or ether (e.g. THF); optionally in the presence of a base such as triethylamine or N-ethyl-N,N-diisopropylamine; and at from ambient to elevated temperature (e.g. reflux).

(j) Where the protecting group is a boc protecting group, its removal is conveniently effected in the presence of an acid, such as an inorganic acid (e.g. anhydrous HCl) or trifluoroacetic acid; in a suitable solvent, such as an ester (e.g. ethyl acetate), haloalkane (e.g. DCM) or ether (e.g. THF); and from 0° C. to ambient temperature.

(k) Compounds of formula (I) may be prepared from a compound of formula (II) according to processes (A)–(F), and (L), described hereinabove.

With reference to process (C), the acid/amine coupling is conveniently effected using an acid chloride of formula (III.3); an excess of an acid acceptor such as triethylamine or N-ethyl-N,N-diisopropylamine; a solvent, such as a haloalkane (e.g. DCM) or an ether (e.g. THF); and at ambient temperature.

Alternatively, the acid/amine coupling is effected using an acid of formula (III.3) activated by reagents such as WSCDI or DCC and HOBt or HOAt; an excess of an acid acceptor such as triethylamine or N-ethyl-N,N-diisopropylamine; a solvent, such as a haloalkane (e.g. DCM) or an ether (e.g. THF); and at ambient temperature.

In a further alternative, the acid/amine coupling is effected using an acid of formula (III.3); either PyBOP, PyBrOP or Mukaiyama's reagent; an excess of an acid acceptor such as triethylamine or N-ethyl-N,N-diisopropylamine; a solvent such as a haloalkane (e.g. DCM) or an ether (e.g. THF); and at ambient temperature.

It will be appreciated by those skilled in the art that one or more of the transformations described in the scheme 1 may be carried out in a different order from that described, or may be modified, in order to provide the desired compound of formula (I).

In one variation of scheme 1, step (i) may be effected under conditions of reductive amination, such as those described above for step (g), employing a compound of formula (III.2).

In another variation of scheme 1, compounds of formula (IV) wherein $R^4$ is $COR^5$ may be prepared by reacting a compound of formula (V) with a compound of formula (III.3) under conventional carboxylic acid/amine coupling, such as those described above under step (k).

In another variation of scheme 1, compounds of formula (IV) wherein $R^4$ is $CO_2R^5$ are prepared by reacting a compound of formula (V) with a haloformate of formula (III.4) (e.g. a chloroformate); optionally with an acid acceptor, such as triethylamine or N-ethyl-N,N-diisopropylamine; in a solvent, such as a haloalkane (e.g. DCM) or an ether (e.g. THF); and at from 0° C. to ambient temperature.

In another variation of scheme 1, compounds of formula (IV) wherein $R^4$ is $CONR^6R^7$ may be prepared by reacting a compound of formula (V) with an acylimidazolide of formula (III.5); optionally with an acid acceptor, such as triethylamine or N-ethyl-N,N-diisopropylamine; in a solvent, such as a haloalkane (e.g. DCM) or an ether (e.g. THF); and at from 0° C. to ambient temperature.

In another variation of scheme 1, compounds of formula (IV) wherein $R^4$ is $SO_2R^5$ may be prepared by reacting a compound of formula (V) with a sulphonylhalide of formula (III.6) (e.g. a sulphonylchloride); optionally with an acid acceptor, such as triethylamine or N-ethyl-N,N-diisopropylamine; in a solvent, such as a haloalkane (e.g. DCM); and at from 0° C. to ambient temperature.

In another variation of scheme 1, compounds of formula (I) wherein X is $NR^4$ and Y is $CH_2$ may be prepared by replacing in step (a) the nitropyridine of formula (XV) with a nitropyridine of formula (XVI)

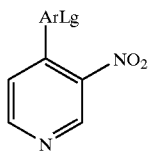

(XVI)

The skilled artisan will appreciate, therefore, that those formulae in Scheme 1 derived from formula (XV), including formulae (I), (II), (IV), (V), (VI), (VII), (IX), (X), (XI) and (XII), are intended to embrace the corresponding compounds derived formula (XVI).

In another variation of scheme 1, compounds of formula (I) may be prepared by carrying out steps (h) to (k) in a different order, as illustrated in scheme 1a that follows.

a compound of formula (XXIV) wherein, respectively, $R^1$ is: $R^5$, $COR^5$, $CO_2R^5$, $CONR^6R^7$ and $SO_2R^5$.

Compounds of formulae (XVII), (XIX) and (XXII) are of analogous structure to compounds of formula (I), or intermediates thereto, and may be prepared by analogous methods.

Compounds of formulae (III.1) to (III.6), (VIII), (XIII) to (XVI), (XVIII), (XX), and (XXI) are either known compounds or may be prepared by conventional chemistry; see, for example: WO01/90106.

A pharmaceutically acceptable salt of a compound of the formula (I) may be readily prepared by mixing together solutions of a compound of the formula (I) and the desired acid. The salt may precipitate from solution and be collected by filtration or may be recovered by evaporation of the solvent.

The compounds of formula (I) and their pharmaceutically acceptable salts, solvates and derivatives are useful because Scheme 1a

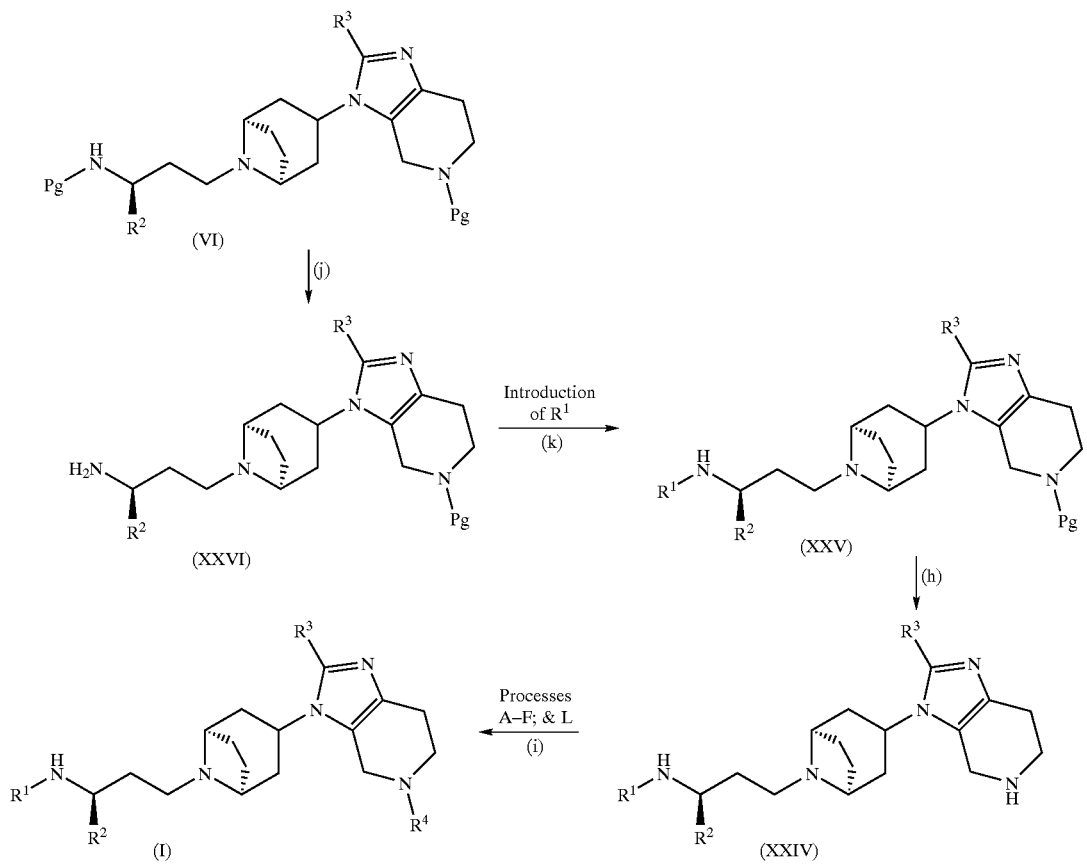

The skilled artisan will appreciate that the variations discussed just above, with respect to $R^4$ and step (i) of scheme 1, apply just as equally to $R^1$ and step (k) of scheme 1a. Likewise, with reference to the variation of scheme 1 discussed just above deriving from formula (XVI), the skilled artisan will appreciate that those formulae in Scheme 1a derived from formula (XV), including formulae (I), (VI), (XXIV), (XXV) and (XXVI), are intended to embrace the corresponding compounds derived formula (XVI).

Moreover, the skilled artisan will further appreciate that processes (A) to (F), and (L), have direct counterparts in respect of the preparation of compounds of formula (I) from they have pharmacological activity in animals, including humans. More particularly, they are useful in the treatment of a disorder in which the modulation of CCR5 receptors is implicated. Disease states of particular interest include HIV, retroviral infections genetically related to HIV, AIDS, and inflammatory diseases.

The compounds of this invention may be used for treatment of respiratory disorders, including adult respiratory distress syndrome (ARDS), bronchitis, chronic bronchitis, chronic obstructive pulmonary disease, cystic fibrosis, asthma, emphysema, rhinitis and chronic sinusitis.

Other conditions that may be treated are those triggered, affected or are in any other way correlated with T-cell trafficking in different organs. It is expected that the compounds of this invention may be useful for the treatment of such conditions and in particular, but not limited to the following for which a correlation with CCR5 or CCR5 chemokines has been established: inflammatory bowel disease, including Crohn's disease and ulcerative colitis, multiple sclerosis, rheumatoid arthritis, graft rejection, in particular but not limited to solid organ translplasnts, such as heart, lung, liver, kidney and pancreas transplants (e.g. kidney and lung allografts), endometriosis, type I diabetes, renal diseases, such as glomerular disease, fibrosis, such as liver, pulmonary and renal fibosis, chronic pancreatitis, inflammatory lung conditions, encephalitis, such as HIV encephalitis, chronic heart failure, psoriasis, stroke, obesity, CNS diseases, such as AIDS related dementias and Alzheimer's Disease, anaemia, atherosclerotic plaque, atopic dermatitis, chronic pancreatitis, cancer, such as non-Hodgkin's lymphoma, Kaposi's sarcoma, melanoma and breast cancer, and pain, such as nociceptive pain and neuropathic pain (e.g. peripheral neuropathic pain).

Infectious diseases where modulation of the CCR5 receptor is implicated include acute and chronic hepatitis B Virus (HBV) and HCV infection, bubonic, septicemic, and pneumonic plague, pox virus infection, such as smallpox, toxoplasmosis infection, mycobacterium infection, trypanosomal infection such as Chagas' Disease, pneumonia, and cytosporidiosis.

For a recent review of possible applications of chemokines and chemokine receptor blockers see Cascieri, M. A., and Springer, M. S., "The chemokine/chemokine receptor family: potential and progress for therapeutic intervention", Curr. Opin. Chem. Biol., 4(4), 420–7 (August 2000).

The utility of the compounds of formula (I) and their pharmaceutically acceptable salts, solvates and derivatives as inhibitors of HIV infection may be demonstrated by any one or more methodologies known in the art, such as by using the HIV microculture assays described in Dimitrov et al., J. Clin. Microbiol., 28, 734–737 (1990), and the pseudotyped HIV reporter assay described in Connor et al., Virology, 206 (2) 935–44 (1995).

The ability of the compounds of formula (I) and their pharmaceutically acceptable salts, solvates and derivatives to modulate chemokine receptor activity is demonstrated by methodology known in the art, such as: by using the assay for CCR5 binding following procedures disclosed in Combadiere et al., J. Leukoc. Biol., 60, 147–52 (1996); by using the intracellular calcium mobilisation assays as described by the same authors; and by their ability to inhibit binding of HIV envelope protein (gp 120) to CCR5 receptors according to the procedure described in Example 1 of EP 1 118 858 A2 (pp 85–88). Cell lines expressing the receptor of interest include those naturally expressing the receptor, such as PM-1, or IL-2 stimulated peripheral blood lymphocytes (PBL), or a cell engineered to express a recombinant receptor, such as CHO, 300.19, L1.2 or HEK-293.

The compounds of the formula (I) can be administered alone but will generally be administered in admixture with a suitable pharmaceutical excipient, diluent or carrier selected with regard to the intended route of administration and standard pharmaceutical practice.

For example, the compounds of the formula (I) can be administered orally, buccally or sublingually in the form of tablets, capsules, multi-particulates, gels, films, ovules, elixirs, solutions or suspensions, which may contain flavouring or colouring agents, for immediate-, delayed-, modified-, sustained-, pulsed- or controlled-release applications. The compounds of the formula (I) may also be administered as fast-dispersing or fast-dissolving dosage forms or in the form of a high energy dispersion or as coated particles. Suitable formulations of the compounds of the formula (I) may be in coated or uncoated form, as desired.

Such solid pharmaceutical compositions, for example, tablets, may contain excipients such as microcrystalline cellulose, lactose, sodium citrate, calcium carbonate, dibasic calcium phosphate, glycine and starch (preferably corn, potato or tapioca starch), disintegrants such as sodium starch glycollate, croscarmellose sodium and certain complex silicates, and granulation binders such as polyvinylpyrrolidone, hydroxypropylmethylcellulose (HPMC), hydroxypropylcellulose (HPC), sucrose, gelatin and acacia. Additionally, lubricating agents such as magnesium stearate, stearic acid, glyceryl behenate and talc may be included.

GENERAL EXAMPLE

A formulation of the tablet could typically contain from 0.01 mg to 500 mg of active compound whilst tablet fill weights may range from 50 mg to 1000 mg. Examples of formulations for, respectively, 5 and 10 mg tablets are illustrated below:

| Ingredient | % w/w |
| --- | --- |
| Compound of the formula (I)* | 5.000 |
| Avicel PH102 | 60.500 |
| DCP Anhydrous | 30.500 |
| Explotab CLV | 3.000 |
| Magnesium Stearate[1] | 1.000 |
| Compound of the formula (I)* | 10.000 |
| Lactose | 64.125 |
| Starch | 21.375 |
| Croscarmellose sodium | 3.000 |
| Magnesium stearate | 1.500 |

[1]0.5% w/w added pre roller compaction and post milling
*or a pharmaceutically acceptable salt, solvate or derivative thereof - quantity adjusted accordingly and also with respect to drug activity The tablets are manufactured by a standard process, for example, direct compression or a wet or dry granulation process. The tablet cores may be coated with appropriate overcoats, such as Opadry White/Opadry Clear, and are suitable packaged (e.g. in bottles or blister packs).

Solid compositions of a similar type may also be employed as fillers in gelatin or HPMC capsules. Preferred excipients in this regard include lactose, starch, a cellulose, milk sugar or high molecular weight polyethylene glycols. For aqueous suspensions and/or elixirs, the compounds of the formula (I) may be combined with various sweetening or flavouring agents, colouring matter or dyes, with emulsifying and/or suspending agents and with diluents such as water, ethanol, propylene glycol and glycerin, and combinations thereof.

The compounds of the formula (I) can also be administered parenterally, for example, intravenously, intra-arterially, intraperitoneally, intrathecally, intraventricularly, intraurethrally, intrasternally, intracranially, intramuscularly or subcutaneously, or they may be administered by infusion or needleless injection techniques. For such parenteral administration they are best used in the form of a sterile aqueous solution which may contain other substances, for example, enough salts or glucose to make the solution isotonic with blood. The aqueous solutions should be suitably buffered (preferably to a pH of from 3 to 9), if necessary. The preparation of suitable parenteral formulations under sterile conditions is readily accomplished by standard pharmaceutical techniques well-known to those skilled in the art.

For oral or parenteral administration to human patients the daily dosage levels of compounds of formula (I) and their pharmaceutically acceptable salts, solvates and derivatives will be from 0.01 to 30 mg/kg (in single or divided doses) and preferably will be in the range 0.01 to 15 mg/kg. Thus tablets will contain 1 mg to 0.5 g of compound for administration singly or two or more at a time, as appropriate. The physician in any event will determine the actual dosage which will be most suitable for any individual patient and it will vary with the age, weight and response of the particular patient. The above dosages are exemplary of the average case. There can, of course, be individual instances where higher or lower dosage ranges are merited and such are within the scope of this invention.

Oral administration is preferred. Preferably, administration takes place shortly before an effect is required.

The compounds of formula (I) can also be administered intranasally or by inhalation and are conveniently delivered in the form of a dry powder inhaler or an aerosol spray presentation from a pressurised container, pump, spray, atomiser or nebuliser, with or without the use of a suitable propellant, e.g. dichlorodifluoromethane, trichlorofluoromethane, dichlorotetrafluoroethane, a hydrofluoroalkane such as 1,1,1,2-tetrafluoroethane (HFA 134A [trade mark]) or 1,1,1,2,3,3,3-heptafluoropropane (HFA 227EA [trade mark]), carbon dioxide or other suitable gas. In the case of a pressurised aerosol, the dosage unit may be determined by providing a valve to deliver a metered amount. The pressurised container, pump, spray, atomiser or nebuliser may contain a solution or suspension of the active compound, e.g. using a mixture of ethanol and the propellant as the solvent, which may additionally contain a lubricant, e.g. sorbitan trioleate. Capsules and cartridges (made, for example, from gelatin) for use in an inhaler or insufflator may be formulated to contain a powder mix of a compound of the formula (I) and a suitable powder base such as lactose or starch.

Aerosol or dry powder formulations are preferably arranged so that each metered dose or "puff" contains from 1 μg to 10 mg of a compound of the formula (I) for delivery to the patient. The overall daily dose with an aerosol will be in the range of from 1 μg to 20 mg which may be administered in a single dose or, more usually, in divided doses throughout the day.

Alternatively, the compounds of the formula (I) can be administered in the form of a suppository or pessary, or they may be applied topically in the form of a gel, hydrogel, lotion, solution, cream, ointment or dusting powder. The compounds of the formula (I) may also be dermally or transdermally administered, for example, by the use of a skin patch. They may also be administered by the pulmonary or rectal routes.

They may also be administered by the ocular route, particularly for treating inflammatory conditions or diseases of the eye. For ophthalmic use, the compounds can be formulated as micronised suspensions in isotonic, pH adjusted, sterile saline, or, preferably, as solutions in isotonic, pH adjusted, sterile saline, optionally in combination with a preservative such as a benzylalkonium chloride. Alternatively, they may be formulated in an ointment such as petrolatum.

For application topically to the skin, the compounds of the formula (I) can be formulated as a suitable ointment containing the active compound suspended or dissolved in, for example, a mixture with one or more of the following: mineral oil, liquid petrolatum, white petrolatum, propylene glycol, polyoxyethylene polyoxypropylene compound, emulsifying wax and water. Alternatively, they can be formulated as a suitable lotion or cream, suspended or dissolved in, for example, a mixture of one or more of the following: mineral oil, sorbitan monostearate, a polyethylene glycol, liquid paraffin, polysorbate 60, cetyl esters wax, cetearyl alcohol, 2-octyldodecanol, benzyl alcohol and water.

The compounds of the formula (I) may also be used in combination with a cyclodextrin. Cyclodextrins are known to form inclusion and non-inclusion complexes with drug molecules. Formation of a drug-cyclodextrin complex may modify the solubility, dissolution rate, bioavailability and/or stability property of a drug molecule. Drug-cyclodextrin complexes are generally useful for most dosage forms and administration routes. As an alternative to direct complexation with the drug the cyclodextrin may be used as an auxiliary additive, e.g. as a carrier, diluent or solubiliser. Alpha-, beta- and gamma-cyclodextrins are most commonly used and suitable examples are described in WO-A-91/11172, WO-A-94/02518 and WO-A-98/55148.

The compounds of formula (I) and their pharmaceutically acceptable salts, solvates and derivatives have the advantage that they are more selective, have a more rapid onset of action, are more potent, are better absorbed, are more stable, are more resistant to metabolism, have a reduced 'food effect', have an improved safety profile or have other more desirable properties (e.g. with respect to solubility or hygroscopicity) than the compounds of the prior art.

The compounds of formula (I) and their pharmaceutically acceptable salts, solvates and derivatives may be administered alone or as part of a combination therapy. Thus included within the scope of the present invention are embodiments comprising coadministration of, and compositions which contain, in addition to a compound of the present invention as active ingredient, additional therapeutic agents and active ingredients. Such multiple drug regimens, often referred to as combination therapy, may be used in the treatment and prevention of any of the diseases or conditions mediated by or associated with CCR5 chemokine receptor modulation, particularly infection by human immunodeficiency virus, HIV. The use of such combinations of therapeutic agents is especially pertinent with respect to the treatment and prevention of infection and multiplication of the human immunodeficiency virus, HIV, and related pathogenic retroviruses within a patient in need of treatment or one at risk of becoming such a patient. The ability of such retroviral pathogens to evolve within a relatively short period of time into strains resistant to any monotherapy which has been administered to said patient is well known in the literature.

In addition to the requirement of therapeutic efficacy, which may necessitate the use of active agents in addition to the CCR5 chemokine receptor modulating compounds of formula (I) and their pharmaceutically acceptable salts, solvates and derivatives, there may be additional rationales which compel or highly recommend the use of combinations of drugs involving active ingredients which represent adjunct therapy, i.e., which complement and supplement the function performed by the CCR5 chemokine receptor modulating compounds of the present invention. Such supplementary therapeutic agents used for the purpose of auxiliary treatment include drugs which, instead of directly treating or preventing a disease or condition mediated by or associated with CCR5 chemokine receptor modulation, treat diseases or conditions which directly result from or indirectly accompany the basic or underlying CCR5 chemokine receptor modulated disease or condition. For example, where the basic CCR5 chemokine receptor modulated disease or condition is HIV infection and multiplication, it may be necessary or at least desirable to treat opportunistic infections, neoplasms, and other conditions which occur as the result of the immune-compromised state of the patient being treated. Other active agents may be used with the compounds of formula (I) and their pharmaceutically acceptable salts, solvates and derivatives, e.g., in order to provide immune stimulation or to treat pain and inflammation which accompany the initial and fundamental HIV infection.

Thus, the methods of treatment and pharmaceutical compositions of the present invention may employ the compounds of formula (I) and their pharmaceutically acceptable salts, solvates and derivatives in the form of monotherapy, but said methods and compositions may also be used in the form of multiple therapy in which one or more compounds of formula (I) or their pharmaceutically acceptable salts, solvates and derivatives are coadministered in combination with one or more known therapeutic agents such as those described in detail further herein.

Preferred combinations of the present invention include simultaneous, or sequential treatments with a compound of formula (I), or a pharmaceutically acceptable salt, solvate or derivative thereof, and one or more inhibitors of HIV protease and/or inhibitors of HIV reverse transcriptase, preferably selected from the class of non-nucleoside reverse transcriptase inhibitors (NNRTI), including but not limited to nevirapine, delavirdine and efavirenz; from among the nucleoside/nucleotide inhibitors, including but not limited to zidovudine, didanosine, zalcitabine, stavudine, lamivudine, abacavir, adefovir and dipivoxil; and from among the protease inhibitors, including but not limited to indinavir, ritonavir, saquinavir, nelfinavir, lopinavir and amprenavir.

Other agents useful in the above-described preferred embodiment combinations of the present invention include current and to-be-discovered investigational drugs from any of the above classes of inhibitors, including but not limited to FTC, PMPA, fozivudine tidoxil, talviraline, S-1153, MKC-442, MSC-204, MSH-372, DMP450, PNU-140690, ABT-378, KNI-764, TMC120 and TMC125.

There is also included within the scope of the preferred embodiments of the present invention, combinations of a compound of formula (I), or a pharmaceutically acceptable salt, solvate or derivative thereof, together with a supplementary therapeutic agent used for the purpose of auxiliary treatment, wherein said supplementary therapeutic agent comprises one or more members independently selected from the group consisting of proliferation inhibitors, e.g., hydroxyurea; immunomodulators, e.g., sargramostim, and various forms of interferon or interferon derivatives; fusion inhibitors, e.g., AMD3100, T-20, T-1249, PRO-140, PRO-542, AD-349, BB-10010 and other chemokine receptor agonists/antagonists; tachykinin receptor modulators, e.g. NK1 antagonists; integrase inhibitors, e.g., AR177; RNaseH inhibitors; inhibitors of viral transcription and RNA replication; and other agents that inhibit viral infection or improve the condition or outcome of HIV-infected individuals through different mechanisms.

Preferred methods of treatment of the present invention for the prevention of HIV infection, or treatment of aviremic and asymptomatic subjects potentially or effectively infected with HIV, include but are not limited to administration of a member independently selected from the group consisting of: (i) a compound within the scope of formula (I) as disclosed herein; (ii) one NNRTI in addition to a compound of (i); (iii) two NRTI in addition to a compound of (i); (iv) one NRTI in addition to the combination of (ii); and (v) a compound selected from the class of protease inhibitors used in place of a NRTI in combinations (iii) and (iv).

The preferred methods of the present invention for therapy of HIV-infected individuals with detectable viremia or abnormally low CD4 counts further include as a member to be selected: (vi) treatment according to (i) above in addition to the standard recommended initial regimens for the therapy of established HIV infections, e.g., see http://hivatis.org/trtgdlns.html. Such standard regimens include but are not limited to an agent from the class of protease inhibitors in combination with two NRTIs; and (vii) a standard recommended initial regimens for the therapy of established HIV infections, e.g., see http://hivatis.org/trtgdlns.html, where either the protease inhibitor component, or one or both of the NRTIs is/are replaced by a compound within the scope of formula (I) as disclosed herein.

The preferred methods of the present invention for therapy of HIV-infected individuals that have failed antiviral therapy further include as a member to be selected: (viii) treatment according to (i) above, in addition to the standard recommended regimens for the therapy of such patients, e.g., see http://hivatis.org/trtgdlns.html; and (ix) a standard recommended initial regimens for the therapy of patients who have failed antiretroviral therapy, e.g., see http://hivatis.org/trtgdlns.html, where either one of the protease inhibitor components, or one or both of the NRTIs is/are replaced by a compound within the scope of formula (I) as disclosed herein.

Additional combinations for use according to the invention include combination of a compound of formula (I), or a pharmaceutically acceptable salt, solvate or derivative thereof with another CCR5 antagonist, such as N-{(1S)-3-[3-(3-isopropyl-5-methyl-4H-1,2,4-triazol-4-yl)-exo-8-azabicyclo[3.2.1]oct-8-yl]-1-phenylpropyl}-4,4-difluorocyclohexanecarboxamide; a CCR1 antagonist, such as BX-471; a beta adrenoceptor agonist, such as salmeterol; a corticosteroid agonist, such fluticasone propionate; a LTD4 antagonist, such as montelukast; a muscarinic antagonist, such as tiotropium bromide; a PDE4 inhibitor, such as cilomilast or roflumilast; a COX-2 inhibitor, such as celecoxib, valdecoxib or rofecoxib; an alpha-2-delta ligand, such as gabapentin or pregabalin; a beta-interferon, such as REBIF; a TNF receptor modulator, such as a TNF-alpha inhibitor (e.g. adalimumab), a HMG CoA reductase inhibitor, such as a statin (e.g. atorvastatin); or an immunosuppressant, such as cyclosporin or a macrolide such as tacrolimus.

In the above-described preferred embodiment combinations of the present invention, the compound of formula (I) or a pharmaceutically acceptable salt, solvate or derivative thereof and other therapeutic active agents may be administered in terms of dosage forms either separately or in conjunction with each other, and in terms of their time of administration, either serially or simultaneously. Thus, the administration of one component agent may be prior to, concurrent with, or subsequent to the administration of the other component agent(s).

It is to be appreciated that all references herein to treatment include curative, palliative and prophylactic treatment.

Thus the invention provides:

a compound of formula (I) or a pharmaceutically acceptable salt, solvate or derivative thereof;

processes for the preparation of a compound of formula (I) or a pharmaceutically acceptable salt, solvate or derivative thereof;

a pharmaceutical composition including a compound of formula (I) or a pharmaceutically acceptable salt, solvate or derivative thereof, together with a pharmaceutically acceptable excipient, diluent or carrier;

a compound of formula (I) or a pharmaceutically acceptable salt, solvate or derivative thereof, for use as a medicament;

a compound of formula (I) or a pharmaceutically acceptable salt, solvate or derivative thereof, for the treatment of a disorder in which the modulation of CCR5 receptors is implicated;

a compound of formula (I) or a pharmaceutically acceptable salt, solvate or derivative thereof, for the treatment of HIV, a retroviral infection genetically related to HIV, AIDS, or an inflammatory disease;

a compound of formula (I) or a pharmaceutically acceptable salt, solvate or derivative thereof, for the treatment of a respiratory disorder including adult respiratory distress syndrome (ARDS), bronchitis, chronic bronchitis, chronic obstructive pulmonary disease, cystic fibrosis, asthma, emphysema, rhinitis or chronic sinusitis;

a compound of formula (I) or a pharmaceutically acceptable salt, solvate or derivative thereof, for the treatment of an inflammatory bowel disease, including Crohn's disease or ulcerative colitis, multiple sclerosis, rheumatoid arthritis, graft rejection, including a kidney or a lung allograft, endometriosis, type I diabetes, a renal disease, chronic pancreatitis, an inflammatory lung condition or chronic heart failure;

the use of a compound of formula (I) or of a pharmaceutically acceptable salt, solvate or derivative thereof, for the manufacture of a medicament for the treatment of a disorder in which the modulation of CCR5 receptors is implicated;

the use of a compound of formula (I) or of a pharmaceutically acceptable salt, solvate or derivative thereof, for the manufacture of a medicament for the treatment of HIV, a retroviral infection genetically related to HIV, AIDS, or an inflammatory disease;

the use of a compound of formula (I) or of a pharmaceutically acceptable salt, solvate or derivative thereof, for the manufacture of a medicament for the treatment of a respiratory disorder including adult respiratory distress syndrome (ARDS), bronchitis, chronic bronchitis, chronic obstructive pulmonary disease, cystic fibrosis, asthma, emphysema, rhinitis or chronic sinusitis;

the use of a compound of formula (I) or of a pharmaceutically acceptable salt, solvate or derivative thereof, for the manufacture of a medicament for the treatment of an inflammatory bowel disease, including Crohn's disease or ulcerative colitis, multiple sclerosis, rheumatoid arthritis, graft rejection, including a kidney or a lung allograft, endometriosis, type I diabetes, a renal disease, chronic pancreatitis, an inflammatory lung condition or chronic heart failure;

a method of treatment of a mammalian disorder in which the modulation of CCR5 receptors is implicated which comprises treating said mammal with an effective amount of a compound of formula (I) or with a pharmaceutically acceptable salt, solvate or derivative thereof;

a method of treatment of HIV, a retroviral infection genetically related to HIV, AIDS, or an inflammatory disease which comprises treating said mammal with an effective amount of a compound of formula (I) or with a pharmaceutically acceptable salt, solvate or derivative thereof;

a method of treatment of a respiratory disorder including adult respiratory distress syndrome (ARDS), bronchitis, chronic bronchitis, chronic obstructive pulmonary disease, cystic fibrosis, asthma, emphysema, rhinitis or chronic sinusitis which comprises treating said mammal with an effective amount of a compound of formula (I) or with a pharmaceutically acceptable salt, solvate or derivative thereof;

a method of treatment of an inflammatory bowel disease, including Crohn's disease or ulcerative colitis, multiple sclerosis, rheumatoid arthritis, graft rejection, including a kidney or a lung allograft, endometriosis, type I diabetes, a renal disease, chronic pancreatitis, an inflammatory lung condition or chronic heart failure which comprises treating said mammal with an effective amount of a compound of formula (I) or with a pharmaceutically acceptable salt, solvate or derivative thereof; and intermediates of the formulae (II), (IV), (V), (VI), (VII), (IX), (X), (XI), (XVII), (XIX), (XXII), (XXIV), (XXV), and (XXVI); the corresponding intermediates obtained by replacing in step (a) the nitropyridine of formula (XV) with a nitropyridine of formula (XVI); and the corresponding deprotected derivatives thereof.

The invention is illustrated by the following Examples and Preparations in which the following further abbreviations may be used:

0.88 ammonia=concentrated ammonium hydroxide solution, 0.88 SG
h=hour
min=minute
MS=mass spectrum
NMR=nuclear magnetic resonance
Me=methyl Example 1

N-{(1S)-3-[3-endo-(5-Benzyl-2-methyl-4,5,6,7-tetrahydro-3H-imidazo[4,5-c]pyridin-3-yl)-8-azabicyclo[3.2.1]oct-8-yl]-1-phenylpropyl}acetamide

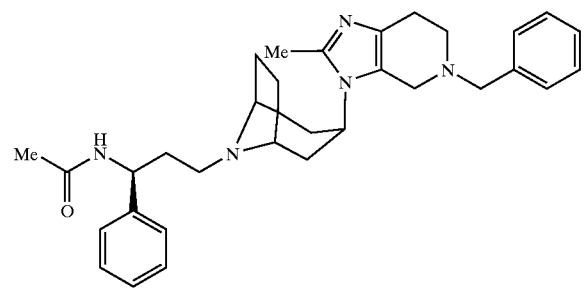

Acetyl chloride (0.3 ml, 4.20 mmol) was added to a solution of (1S)-3-[3-endo-(5-benzyl-2-methyl-4,5,6,7-tetrahydro-3H-imidazo[4,5-c]pyridin-3-yl)-8-azabicyclo

[3.2.1]oct-8-yl]-1-phenylpropylamine (Preparation 13) (1.8 g, 3.84 mmol) dissolved in dichloromethane (30 ml) under nitrogen at room temperature. The reaction was stirred at room temperature for 2 hours, and the solvent was removed under reduced pressure. The residue was purified by flash column chromatography on silica gel eluting with a solvent gradient of dichloromethane:methanol:concentrated aqueous ammonia (94:6:0.6, by volume, changing to 92:8:0.8 then 90:10:1). Product containing fractions were evaporated to afford the title compound as a white foam (1.76 g).

$^1$H NMR (400 MHz, CDCl$_3$): δ: 7.20–7.38 (10H, m), 6.42–6.48 (1H, d), 5.05–5.14 (1H, m), 4.23–4.37 (1H, m), 3.68 (2H, s), 3.44 (2H, s), 3.19–3.28 (2H, m), 2.81–2.89 (2H, m), 2.63–2.69 (2H, m), 2.31–2.45 (5H, m), 2.13–2.22 (2H, m), 1.82–2.02 (7H, m), 1.26–1.42 (2H, q), 1.14–1.41 (2H, m) ppm.

LRMS (electrospray): m/z [M+Na]$^+$ 534, [M+H]$^+$ 512, [M–H]$^+$ 510.

Found C, 72.92; H, 8.06; N, 13.45. C$_{32}$H$_{41}$N$_5$O. 0.75 mol H$_2$O requires C, 73.18; H, 8.16; N, 13.33%.

Example 2

N-{(1S)-3-[3-endo-(2-Methyl-4,5,6,7-tetrahydro-3H-imidazo[4,5-c]pyridin-3-yl)-8-azabicyclo[3.2.1]oct-8-yl]-1-phenylpropyl}acetamide

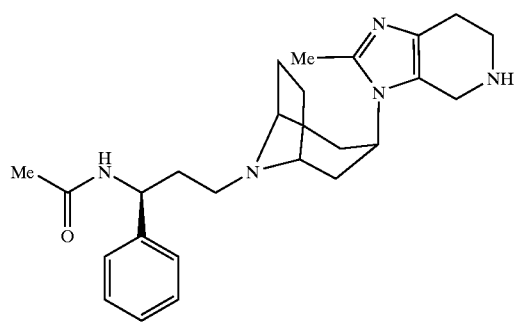

20% Palladium on carbon (0.16 g) was added to a solution of N-{(1S)-3-[3-endo-(5-benzyl-2-methyl-4,5,6,7-tetrahydro-3H-imidazo[4,5-c]pyridin-3-yl)-8-azabicyclo [3.2.1]oct-8-yl]-1-phenylpropyl}acetamide (Example 1) (0.80 g, 1.56 mmol) dissolved in ethanol (20 ml) under nitrogen at room temperature. Ammonium formate (0.40 g, 6.34 mmol) was then added and the reaction mixture was gently refluxed for 30 minutes. A further aliquot of ammonium formate (0.20 g, 3.17 mmol) was then added and the solution gently refluxed for 45 minutes. The reaction mixture was cooled to room temperature and filtered through Arbocel® washing well with ethanol. The filtrate was concentrated under reduced pressure and the residue was purified by flash column chromatography on silica gel eluting with a solvent gradient of dichloromethane:methanol:concentrated aqueous ammonia (92:8:0.8, by volume, changing to 90:10:1). Product containing fractions were evaporated to afford the title compound as a white foam (0.61 g).

$^1$H NMR (400 MHz, CDCl$_3$): δ: 7.20–7.38 (5H, m), 6.26–6.36 (1H, d), 5.12–5.19 (1H, m), 4.36–4.46 (1H, m), 3.89 (2H, s), 3.27–3.37 (2H, m), 3.03–3.09 (2H, m), 2.52–2.63 (2H, m), 2.31–2.53 (5H, m), 2.17–2.29 (2H, m), 1.89–2.17 (7H, m), 1.40–1.59 (4H, m) ppm.

LRMS (electrospray): m/z [M+Na]$^+$ 444, [M+H]$^+$ 422, [M–H]$^+$ 420.

Found C, 67.14; H, 8.29; N, 15.62. C$_{25}$H$_{35}$N$_5$O. 1.5 mol H$_2$O requires C, 66.93; H, 8.54; N, 15.61%.

Example 3

N-{(1S)-3-[3-endo-(5-Acetyl-2-methyl-4,5,6,7-tetrahydro-3H-imidazo[4,5-c]pyridin-3-yl)-8-azabicyclo[3.2.1]oct-8-yl]-1-phenylpropyl}acetamide

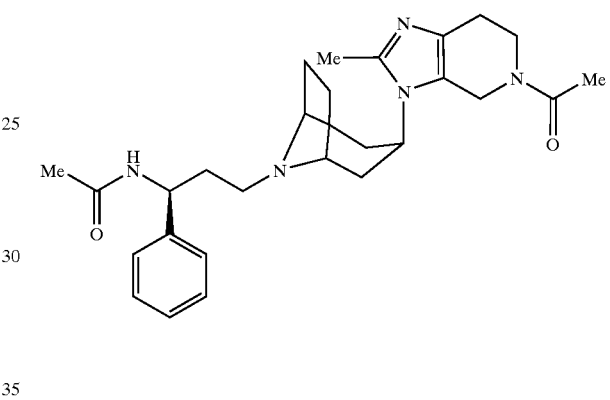

Acetyl chloride (0.015 ml, 0.173 mmol) was added to a solution of N-{(1S)-3-[3-endo-(2-methyl-4,5,6,7-tetrahydro-3H-imidazo[4,5-c]pyridin-3-yl)-8-azabicyclo [3.2.1]oct-8-yl]-1-phenylpropyl}acetamide (Example 2) (0.066 g, 0.157 mmol) dissolved in dichloromethane (4 ml) under nitrogen at room temperature. The reaction was stirred at room temperature for 30 minutes, and the reaction mixture was washed with saturated aqueous sodium hydrogencarbonate solution (5 ml). The organic phase was dried (MgSO$_4$) and the solvent was removed under reduced pressure. The residue was purified by flash column chromatography on silica gel eluting with a solvent gradient of dichloromethane:methanol:concentrated aqueous ammonia (94:6:0.6, by volume, changing to 92:8:0.8). Product containing fractions were evaporated to afford the title compound as a white foam (0.069 g) which was a mixture of rotamers.

$^1$H NMR (400 MHz, CDCl$_3$): δ: 7.23–7.40 (5H, m), 6.26–6.31 (0.83H, d), 6.03–6.07 (0.17H, d), 5.18–5.24 (0.17H, q), 5.12–5.18 (0.83H, q), 4.64 (2H, s), 4.37–4.59 (1H, m), 3.80–3.85 (0.34H, m), 3.64–3.69 (1.66H, t), 3.31–3.38 (2H, m), 2.60–2.66 (0.34H, m), 2.67–2.73 (1.66H, m), 2.38–2.54 (5H, m), 2.20–2.24 (2H, t), 2.18 (3H, s), 2.02–2.17 (2H, m), 2.00 (3H, s), 1.93–1.99 (2H, m), 1.42–1.64 (4H, m) ppm.

LRMS (electrospray): m/z [M+Na]$^+$ 486, [M+H]$^+$ 464, [M–H]$^+$ 462.

Example 4

N-{(1S)-3-[3-endo-(5-Isopropyl-2-methyl-4,5,6,7-tetrahydro-3H-imidazo[4,5-c]pyridin-3-yl)-8-azabicyclo[3.2.1]oct-8-yl]-1-phenylpropyl}acetamide

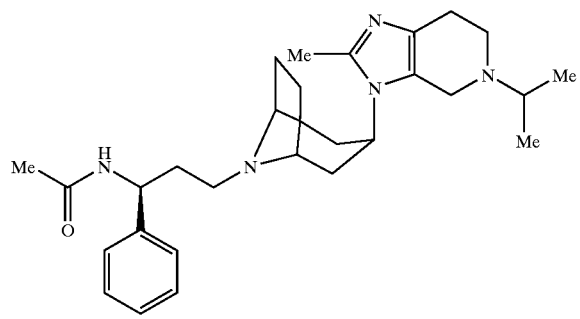

Acetic acid (0.06 ml, 1.04 mmol) was added to a stirred solution of N-{(1S)-3-[3-endo-(2-methyl-4,5,6,7-tetrahydro-3H-imidazo[4,5-c]pyridin-3-yl)-8-azabicyclo[3.2.1]oct-8-yl]-1-phenylpropyl}acetamide (Example 2) (0.09 g, 0.21 mmol) and acetone (0.03 ml, 0.41 mmol) dissolved in dichloromethane (5 ml) under nitrogen at room temperature. Sodium triacetoxyborohydride (0.09 g, 0.42 mmol) was then added and the reaction was held at room temperature for 18 hours. A further aliquot of acetone (0.03 ml, 0.41 mmol) and sodium triacetoxyborohydride (0.09 g, 0.42 mmol) was added and the reaction stirred at room temperature for a further 24 hours. The reaction mixture was partitioned between saturated aqueous sodium hydrogencarbonate solution (10 ml) and dichloromethane (10 ml). The organic phase was removed and the aqueous phase was washed with dichloromethane (10 ml). The combined organic phases were washed with $H_2O$ (10 ml), dried ($MgSO_4$) and the solvent was removed under reduced pressure. The residue was purified by flash column chromatography on silica gel eluting with a solvent gradient of dichloromethane:methanol:concentrated aqueous ammonia (94:6:0.6, by volume, changing to 92:8:0.8). Product containing fractions were evaporated to afford the title compound as a white foam (0.066 g).

$^1$H NMR (400 MHz, $CDCl_3$): δ: 7.24–7.39 (5H, m), 6.26–6.45 (1H, d), 5.12–5.18 (1H, q), 4.31–4.43 (1H, m), 3.62 (2H, s), 3.29–3.38 (2H, m), 2.88–2.97 (1H, m), 2.75–2.81 (2H, m), 2.58–2.65 (2H, m), 2.41–2.51 (2H, m), 2.37 (3H, s), 2.20–2.25 (2H, m), 2.03–2.12 (2H, m), 2.01 (3H, s), 1.91–2.00 (2H, m), 1.47–1.60 (4H, m), 1.11–1.18 (6H, d) ppm.

LRMS (electrospray): m/z $[M+Na]^+$ 486, $[M+H]^+$ 464, $[M-H]^+$ 462.

Found C, 69.93; H, 8.92; N, 14.69. $C_{28}H_{41}N_5O$. 1 mol $H_2O$ requires C, 69.82; H, 9.00; N, 14.54%.

Example 5

N-{(1S)-3-[3-endo-(2,5-Dimethyl-4,5,6,7-tetrahydro-3H-imidazol[4,5-c]pyridin-3-yl)-8-azabicyclo[3.2.1]oct-8-yl]-1-phenylpropyl}acetamide

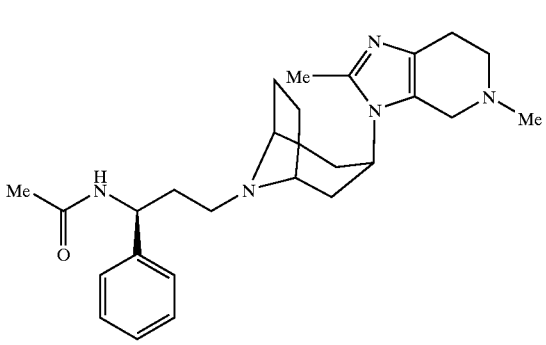

Sodium triacetoxyborohydride (0.50 g, 2.35 mmol) was added to a stirred solution of N-{(1S)-3-[3-endo-(2-methyl-4,5,6,7-tetrahydro-3H-imidazo[4,5-c]pyridin-3-yl)-8-azabicyclo[3.2.1]oct-8-yl]-1-phenylpropyl}acetamide (Example 2) (0.45 g, 1.06 mmol) and paraformaldehyde (0.064 g, 2.13 mmol) dissolved in dichloromethane (4 ml) under nitrogen at room temperature, and the reaction stirred at room temperature for 18 hours. Further aliquots of paraformaldehyde (0.064 g, 2.13 mmol) and sodium triacetoxyborohydride (0.5 g, 2.35 mmol) were added and stirring continued for a further 24 hours. The reaction mixture was partitioned between saturated aqueous sodium hydrogencarbonate solution (10 ml) and dichloromethane (10 ml). The organic phase was removed and the aqueous phase was washed with dichloromethane (10 ml). The combined organic phases were washed with $H_2O$ (10 ml), dried ($MgSO_4$) and the solvent was removed under reduced pressure. The residue was purified by flash column chromatography on silica gel eluting with a solvent gradient of dichloromethane:methanol:concentrated aqueous ammonia (92:8:0.8, by volume, changing to 90:10:0.5 then 90:10:0.6). Product containing fractions were evaporated to afford the title compound as a white foam (0.10 g).

$^1$H NMR (400 MHz, $CDCl_3$): δ: 7.23–7.38 (5H, m), 6.34–6.39 (1H, d), 5.10–5.18 (1H, q), 4.35–4.44 (1H, m), 3.50 (2H, s), 3.31–3.38 (2H, m), 2.63–2.73 (4H, m), 2.37–2.51 (8H, m), 2.19–2.25 (2H, t), 1.90–2.16 (9H, m), 1.43–1.60 (2H, m) ppm.

LRMS (electrospray): m/z $[M+H]^+$ 436, $[M-H]^+$ 434.

Found C, 69.17; H, 8.62; N, 15.43. $C_{26}H_{37}N_5O$. 0.9 mol $H_2O$ requires C, 69.12; H, 8.66; N, 15.50%.

Example 6

N-((1S)-3-{3-endo-[2-Methyl-5-(methylsulfonyl)-4,5,6,7-tetrahydro-3H-imidazol[4,5-c]pyridin-3-yl]-8-azabicyclo[3.2.1]oct-8-yl}-1-phenylpropyl)acetamide

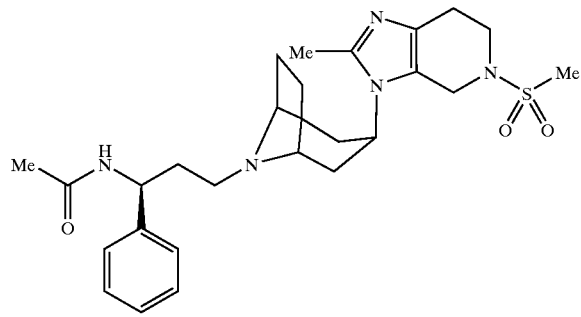

Methanesulfonyl chloride (0.02 ml, 0.25 mmol) was added to a solution of N-{(1S)-3-[3-endo-(2-methyl-4,5,6,7-tetrahydro-3H-imidazo[4,5-c]pyridin-3-yl)-8-azabicyclo[3.2.1]oct-8-yl]-1-phenylpropyl}acetamide (Example 2) (0.08 g, 0.19 mmol) and triethylamine (0.04 ml, 0.29 mmol) dissolved in dichloromethane (3 ml) under nitrogen at room temperature. The reaction was stirred at room temperature for 18 hours, and the solvent was removed under reduced pressure. The residue was purified by flash column chromatography on silica gel eluting with a solvent gradient of dichloromethane:methanol:concentrated aqueous ammonia (94:6:0.6, by volume, changing to 92:8:0.8). Product containing fractions were evaporated to afford the title compound as a pink foam (0.065 g).

$^1$H NMR (400 MHz, CDCl$_3$): δ: 7.22–7.43 (5H, m), 6.03–6.11 (1H, d), 5.13–5.22 (1H, q), 4.38–4.48 (3H, m), 3.56–3.67 (2H, m), 3.28–3.39 (2H, m), 2.84 (3H, s), 2.70–2.78 (2H, m), 2.38–2.68 (5H, m), 2.18–2.37 (2H, m), 1.90–2.17 (7H, m), 1.52–1.68 (2H, d), 1.39–1.51 (2H, m) ppm.

LRMS (electrospray): m/z [M+Na]$^+$ 522, [M+H]$^+$ 500, [M–H]$^+$ 498.

Found C, 60.68; H, 7.50; N, 13.41. C$_{26}$H$_{37}$N$_5$O$_3$S. 0.75 mol H$_2$O requires C, 60.85; H, 7.56; N, 13.65%.

Example 7

Methyl 3-endo-{8-[(3S)-3-(acetamido)-3-phenylpropyl]-8-azabicyclo[3.2.1]oct-3-yl}-2-methyl-4,5,6,7-tetrahydro-3H-imidazo[4,5-c]pyridine-5-carboxylate

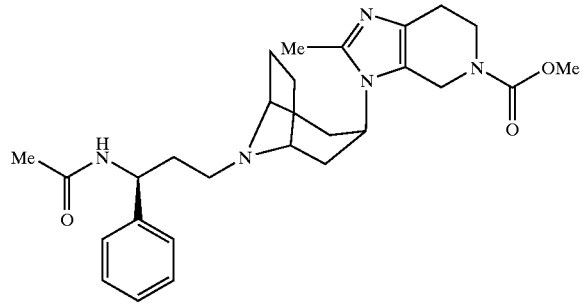

Methyl chloroformate (0.02 ml, 0.25 mmol) was added to a solution of N-{(1S)-3-[3-endo-(2-methyl-4,5,6,7-tetrahydro-3H-imidazo[4,5-c]pyridin-3-yl)-8-azabicyclo[3.2.1]oct-8-yl]-1-phenylpropyl}acetamide (Example 2) (0.08 g, 0.19 mmol) and triethylamine (0.04 ml, 0.29 mmol) dissolved in dichloromethane (3 ml) under nitrogen at room temperature. The reaction was stirred at room temperature for 18 hours, and the solvent was removed under reduced pressure. The residue was purified by flash column chromatography on silica gel eluting with a solvent gradient of dichloromethane:methanol:concentrated aqueous ammonia (94:6:0.6, by volume, changing to 92:8:0.8). Product containing fractions were evaporated to afford the title compound as an off-white foam (0.075 g).

$^1$H NMR (400 MHz, CDCl$_3$): δ: 7.22–7.40 (5H, m), 6.22–6.32 (1H, m), 5.10–5.17 (1H, m), 4.47–4.57 (2H, m), 4.37–4.47 (1H, m), 3.64–3.76 (5H, m), 3.29–3.37 (2H, m), 2.59–2.66 (2H, m), 2.42–2.54 (2H, m), 2.38(3H, s), 2.18–2.28 (2H, m), 1.92–2.15 (7H, m), 1.43–1.60 (4H, m) ppm.

LRMS (electrospray): m/z [M+H]$^+$ 480, [M–H]$^+$ 478.

Found C, 65.92; H, 7.91; N, 14.20. C$_{27}$H$_{37}$N$_5$O$_3$. 0.75 mol H$_2$O requires C, 65.76; H, 7.87; N, 14.20%.

Example 8

N-{(1S)-3-[3-endo-(2-Methyl-5-propionyl-4,5,6,7-tetrahydro-3H-imidazo[4,5-c]pyridin-3-yl)-8-azabicyclo[3.2.1]oct-8-yl[-1-phenylproyl}acetamide

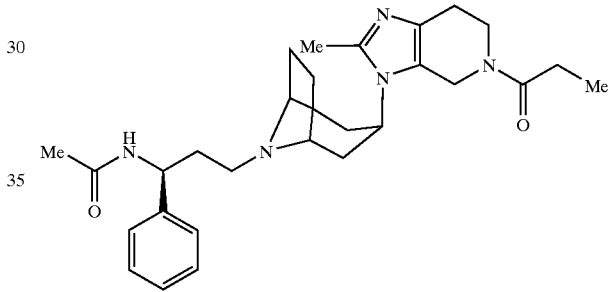

Propionyl chloride (0.02 ml, 0.23 mmol) was added to a solution of N-{(1S)-3-[3-endo-(2-methyl-4,5,6,7-tetrahydro-3H-imidazo[4,5-c]pyridin-3-yl)-8-azabicyclo[3.2.1]oct-8-yl]-1-phenylpropyl}acetamide (Example 2) (0.08 g, 0.19 mmol) and triethylamine (0.04 ml, 0.29 mmol) dissolved in dichloromethane (3 ml) under nitrogen at room temperature. The reaction was stirred at room temperature for 18 hours and the solvent was removed under reduced pressure. The residue was purified by flash column chromatography on silica gel eluting with a solvent gradient of dichloromethane:methanol:concentrated aqueous ammonia (94:6:0.6, by volume, changing to 92:8:0.8). Product containing fractions were evaporated to afford the title compound as a white foam (0.078 g) which was a mixture of rotamers.

$^1$H NMR (400 MHz, CDCl$_3$): δ: 7.22–7.38 (5H, m), 6.28–6.36 (0.8H, d), 6.03–6.08 (0.2H, d), 5.10–5.18 (1H, q), 4.66 (2H, s), 4.37–4.43 (1H, m), 3.82–3.86 (0.4H, m), 3.64–3.73 (1.6H, t), 3.28–3.39 (2H, m), 2.58–2.72 (2H, m), 2.32–2.52 (7H, m), 2.18–2.28 (2H, t), 2.02–2.16 (2H, m), 1.92–2.01 (5H, m), 1.47–1.64 (4H, m), 1.15–1.20 (3H, t) ppm.

LRMS (electrospray): m/z [M+Na]$^+$ 500, [M+H]$^+$ 478, [M–H]$^+$ 476.

Found C, 68.72; H, 8.30; N, 14.29. C$_{28}$H$_{39}$N$_5$O$_2$. 0.75 mol H$_2$O requires C, 68.47; H, 8.31; N, 14.26%.

Example 9

N-{(1S)-3-[3-endo-(5-Isobutyryl-2-methyl-4,5,6,7-tetrahydro-3H-imidazo[4,5-c]pyridin-3-yl)-8-azabicyclo[3.2.1]oct-8-yl]-1-phenylpropyl}acetamide

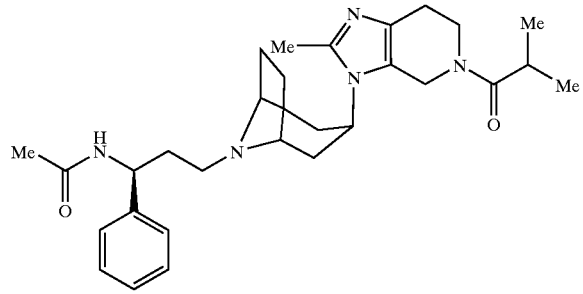

Isobutyryl chloride (0.025 ml, 0.24 mmol) was added to a solution of N-{(1S)-3-[3-endo-(2-methyl-4,5,6,7-tetrahydro-3H-imidazo[4,5-c]pyridin-3-yl)-8-azabicyclo[3.2.1]oct-8-yl]-1-phenylpropyl}acetamide (Example 2) (0.08 g, 0.19 mmol) and triethylamine (0.04 ml, 0.29 mmol) dissolved in dichloromethane (3 ml) under nitrogen at room temperature. The reaction was stirred at room temperature for 18 hours and the solvent was removed under reduced pressure. The residue was purified by flash column chromatography on silica gel eluting with a solvent gradient of dichloromethane:methanol:concentrated aqueous ammonia (94:6:0.6, by volume, changing to 92:8:0.8). Product containing fractions were evaporated to afford the title compound as a white foam (0.078 g) which was a mixture of rotamers.

$^1$H NMR (400 MHz, CDCl$_3$): δ: 7.22–7.38 (5H, m), 6.28–6.34 (0.9H, d), 6.03–6.09 (0.1H, m), 5.18–5.25 (0.1H, m), 5.09–5.17 (0.9H, q), 4.67 (2H, s), 4.52–4.61 (0.1H, m), 4.38–4.52 (0.9H, m), 3.79–3.86 (0.2H, m), 3.70–3.77 (1.8H, t), 3.26–3.37 (2H, m), 2.58–2.74 (2H, m), 2.35–2.50 (5H, m), 2.16–2.28 (2H, t), 2.02–2.15 (2H, m), 1.98 (3H, s), 1.87–1.97 (2H, m), 1.45–1.65 (4H, m), 1.10–1.20 (6H, d) ppm.

LRMS (electrospray): m/z [M+Na]$^+$ 514, [M+H]$^+$ 492, [M–H]$^+$ 490.

Found C, 69.57; H, 8.53; N, 14.08. C$_{29}$H$_{41}$N$_5$O$_2$. 0.5 mol H$_2$O requires C, 69.57; H, 8.46; N, 13.99%.

Example 10

N-{(1S)-3-[3-endo-(2,5-Dimethyl-4,5,6,7-tetrahydro-3H-imidazo[4,5-c]pyridin-3-yl)-8-azabicyclo[3.2.1]oct-8-yl]-1-phenylpropyl}cyclobutanecarboxamide

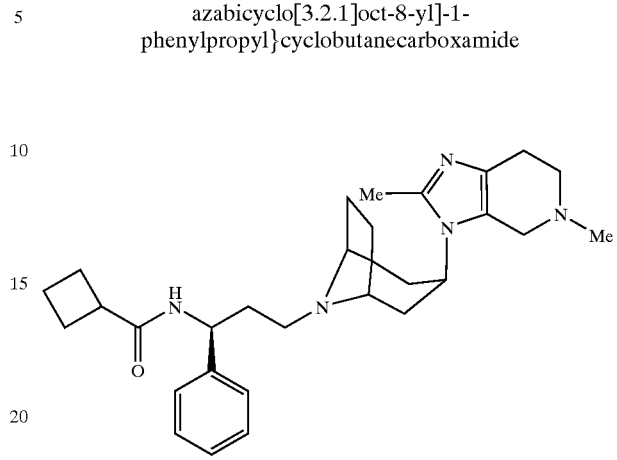

Cyclobutylcarbonyl chloride (0.03 ml, 0.26 mmol) was added to a solution of (1S)-3-[3-endo-(2,5-dimethyl-4,5,6,7-tetrahydro-3H-imidazo[4,5-c]pyridin-3-yl)-8-azabicyclo[3.2.1]oct-8-yl]-1-phenylpropylamine (Preparation 14) (0.085 g, 0.22 mmol) and triethylamine (0.04 ml, 0.29 mmol) dissolved in dichloromethane (3 ml) under nitrogen at room temperature. The reaction was stirred at room temperature for one hour, and the solvent was removed under reduced pressure. The residue was purified by flash column chromatography on silica gel eluting with a solvent gradient of dichloromethane:methanol:concentrated aqueous ammonia (94:6:0.6, by volume, changing to 92:8:0.8 then 90:10:1). Product containing fractions were evaporated to afford the title compound as a white foam (0.089 g).

$^1$H NMR (400 MHz, CDCl$_3$): δ: 7.21–7.37 (5H, m), 6.01–6.07 (1H, d), 5.08–5.15 (1H, q), 4.32–4.43 (1H, m), 3.52 (2H, s), 3.25–3.37 (2H, m), 2.92–3.02 (1H, m), 2.62–2.73 (4H, m), 2.36–2.50 (8H, m), 2.00–2.34 (8H, m), 1.82–1.99 (4H, m), 1.42–1.58 (4H, m) ppm.

LRMS (electrospray): m/z [M+H]$^+$ 476, [M–H]$^+$ 474.

Found C, 71.94; H, 8.79; N, 14.46. C$_{29}$H$_{41}$N$_5$O. 0.5 mol H$_2$O requires C, 71.87; H, 8.73; N, 14.45%.

Example 11

N-{(1S)-3-[3-endo-(2,5-Dimethyl-4,5,6,7-tetrahydro-3H-imidazo[4,5-c]pyridin-3-yl)-8-azabicyclo[3.2.1]oct-8-yl]-1-phenylpropyl}tetrahydropyran-4-carboxamide

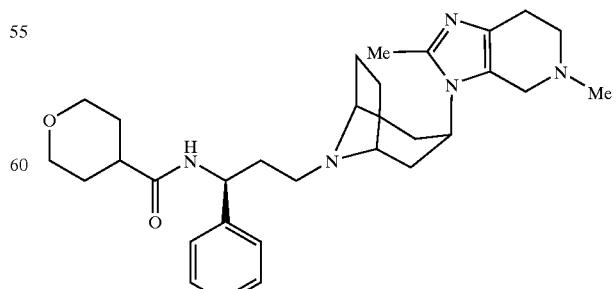

1-(3-Dimethylaminopropyl)-3-ethylcarbodiimide hydrochloride (0.05 g, 0.26 mmol) was added to a solution of tetrahydropyran-4-carboxylic acid (0.03 g, 0.23 mmol), (1S)-3-[3-endo-(2,5-dimethyl-4,5,6,7-tetrahydro-3H-imidazol[4,5-c]pyridin-3-yl)-8-azabicyclo[3.2.1]oct-8-yl]-1-phenylpropylamine (Preparation 14) (0.08 g, 0.20 mmol), triethylamine (0.04 ml, 0.29 mmol) and 1-hydroxybenzotriazole (0.04 g, 0.26 mmol) dissolved in dichloromethane (3 ml) under nitrogen at room temperature. The reaction was stirred at room temperature for 18 hours, and the reaction mixture then partitioned between dichloromethane (10 ml) and saturated aqueous sodium hydrogencarbonate solution (10 ml). The organic phase was dried (MgSO$_4$) and the solvent was removed under reduced pressure. The residue was purified by flash column chromatography on silica gel eluting with a solvent gradient of dichloromethane:methanol:concentrated aqueous ammonia (94:6:0.6, by volume, changing to 92:8:0.8 then 90:10:1). Product containing fractions were evaporated to afford the title compound as a white foam (0.098 g).

$^1$H NMR (400 MHz, CDCl$_3$): δ: 7.33–7.39 (2H, m), 7.23–7.32 (3H, m), 5.88–5.96 (1H, d), 5.08–5.17 (1H, q), 4.35–4.43 (1H, m), 3.97–4.03 (2H, m), 3.48 (2H, s), 3.26–3.44 (4H, m), 2.68–2.73 (2H, m), 2.62–2.68 (2H, m), 2.47 (3H, s), 2.27–2.44 (6H, m), 2.17–2.22 (2H, t), 2.01–2.07 (2H, m), 1.93–2.00 (2H, m), 1.68–1.82 (2H, m), 1.43–1.56 (4H, m) ppm.

LRMS (electrospray): m/z [M+H]$^+$ 506.

Found C, 69.41; H, 8.64; N, 13.50. C$_{30}$H$_{43}$N$_5$O. 0.75 mol H$_2$O requires C, 69.40; H, 8.64; N, 13.49%.

Example 12

N-((1S)-3-{3-endo-2-Methyl-5-(3,3,3-trifluoropropanoyl)-4,5,6,7-tetrahydro-3H-imidazo[4,5-c]pyridin-3-yl]-8-azabicyclo[3.2.1]oct-8-yl}-1-phenylpropyl)acetamide

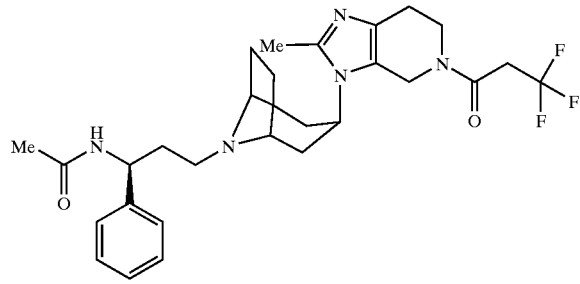

1-(3-Dimethylaminopropyl)-3-ethylcarbodiimide hydrochloride (0.05 g, 0.26 mmol) was added to a solution of 3,3,3-trifluoropropanoic acid (0.027 g, 0.21 mmol), N-{(1S)-3-[3-endo-(2-methyl-4,5,6,7-tetrahydro-3H-imidazo[4,5-c]pyridin-3-yl)-8-azabicyclo[3.2.1]oct-8-yl]-1-phenylpropyl}acetamide (Example 2) (0.08 g, 0.19 mmol), triethylamine (0.04 ml, 0.29 mmol) and 1-hydroxybenzotriazole (0.04 g, 0.26 mmol) dissolved in dichloromethane (3 ml) under nitrogen at room temperature. The reaction mixture was stirred at room temperature for 18 hours, and then partitioned between dichloromethane (10 ml) and saturated aqueous sodium hydrogencarbonate solution (10 ml). The organic phase was dried (MgSO$_4$) and the solvent was removed under reduced pressure. The residue was purified by flash column chromatography on silica gel eluting with a solvent gradient of dichloromethane:methanol (92:8, by volume, changing to 90:10, 85:15 then 80:200). Product containing fractions were evaporated to afford the title compound as a white foam (0.089 g).

$^1$H NMR (400 MHz, CDCl$_3$): δ: 7.21–7.39 (5H, m), 6.17–6.31 (1H, m), 5.10–5.18 (1H, q), 4.71 (2H, s), 4.46–4.83 (1H, m) 3.65–3.75 (2H, m), 3.26–3.48 (4H, m), 2.70–2.76 (1.5H, m), 2.63–2.69 (0.5H, m), 2.44–2.48 (2H, m), 2.42 (0.66H, s), 2.41 (2.33H, s), 2.20–2.37 (2H, m), 1.92–2.19 (7H, m), 1.59–1.62 (2H, m), 1.45–1.61 (2H, m) ppm.

LRMS (electrospray): m/z [M+Na]$^+$ 554, [M+H]$^+$ 532, [M–H]$^+$ 530.

Found C, 60.96; H, 6.80; N, 12.65. C$_{28}$H$_{36}$F$_3$N$_5$O$_2$. 1 mol H$_2$O requires C, 61.19; H, 6.97; N, 12.74%.

Example 13

Methyl 3-endo-{8-[(3S)-3-(acetamido)-3-(3-fluorophenyl)propyl]-8-azabicyclo[3.2.1]oct-3-yl}-2-methyl-4,5,6,7-tetrahydro-3H-imidazo[4,5-c]pyridine-5-carboxylate

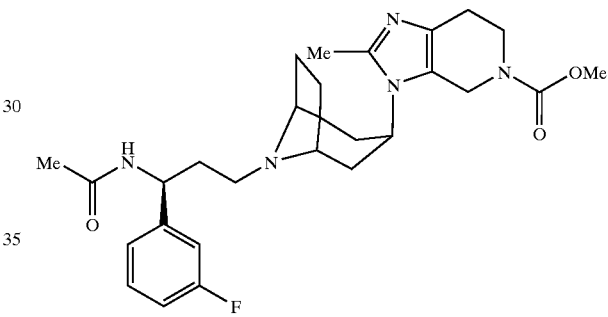

Acetyl chloride (0.026 g, 0.34 mmol) was added to a solution of methyl 3-endo-{8-[(3S)-3-amino-3-(3-fluorophenyl)propyl]-8-azabicyclo[3.2.1]oct-3-yl}-2-methyl-4,5,6,7-tetrahydro-3H-imidazo[4,5-c]pyridine-5-carboxylate (Preparation 21) (0.14 g, 0.31 mmol) and N-ethyl-N,N-diisopropylamine (0.043 g, 0.34 mmol) dissolved in dichloromethane (16 ml) under nitrogen at room temperature. The reaction was stirred at room temperature for 18 hours and quenched with saturated aqueous sodium hydrogencarbonate solution (20 ml). The product was extracted from the organic phase with 2N HCl (3×3 ml) and the aqueous phase was basified to pH 10 using 2N NaOH. This was then extracted with dichloromethane (3×5 ml) and the combined organic extracts were dried (MgSO$_4$). The solvent was removed under reduced pressure to afford the title compound as an off-white solid (0.132 g).

$^1$H NMR (400 MHz, CDCl$_3$): δ: 7.23–7.31 (1H, m), 7.02–7.08 (1H, d), 6.88–6.97 (2H, m), 6.43–6.49 (1H, d), 5.08–5.15 (1H, m), 4.43–4.58 (2H, m), 4.32–4.42 (1H, m), 3.72 (3H, s), 3.58–3.68 (2H, m), 3.25–3.36 (2H, m), 2.57–2.63 (2H, m), 2.39–2.52 (2H, m), 2.37 (3H, s), 2.16–2.23 (2H, t), 1.97–2.12 (5H, m), 1.83–1.96 (2H, m), 1.41–1.63 (4H, m) ppm.

LRMS (electrospray): m/z [M+H]$^+$ 498, [M–H]$^+$ 496.

Example 14

Methyl 3-endo-{8-[(3S)-3-[(cyclobutylcarbonyl)amino]-3-(3-fluorophenyl)propyl]-8-azabicyclo[3.2.1]oct-3-yl}-2-methyl-4,5,6,7-tetrahydro-3H-imidazo[4,5-c]pyridine-5-carboxylate

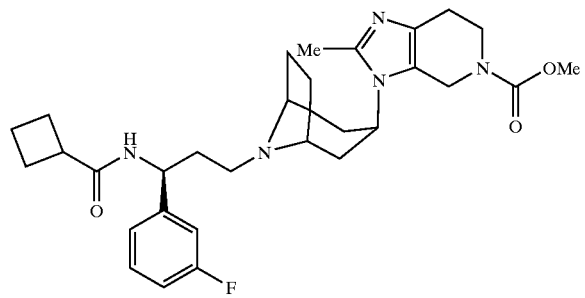

Cyclobutylcarbonyl chloride (0.04 g, 0.34 mmol) was added to a solution of methyl 3-endo-{8-[(3S)-3-amino-3-(3-fluorophenyl)propyl]-8-azabicyclo[3.2.1]oct-3-yl}-2-methyl-4,5,6,7-tetrahydro-3H-imidazo[4,5-c]pyridine-5-carboxylate (Preparation 21) (0.14 g, 0.31 mmol) and N-ethyl-N,N-diisopropylamine (0.043 g, 0.34 mmol) dissolved in dichloromethane (16 ml) under nitrogen at room temperature. The reaction was stirred at room temperature for 18 hours and quenched with saturated aqueous sodium hydrogencarbonate solution (20 ml). The product was extracted from the organic phase with 2N HCl (3×3 ml) and the aqueous phase was basified to pH 10 using 2N NaOH. This was then extracted with dichloromethane (3×5 ml) and the combined organic extracts were dried (MgSO$_4$). The solvent was removed under reduced pressure to afford the title compound as an off-white solid (0.132 g).

$^1$H NMR (400 MHz, CDCl$_3$): δ: 7.22–7.32 (1H, m), 7.00–7.05 (1H, m), 6.87–6.99 (2H, m), 6.04–6.16 (1H, m), 5.03–5.15 (1H, m), 4.45–4.56 (2H, m), 4.32–4.44 (1H, m), 3.57–3.75 (5H, m), 3.24–3.35 (2H, m), 2.92–3.02 (1H, m), 2.56–2.64 (2H, m), 2.34–2.52 (5H, m), 1.98–2.32 (6H, m), 1.79–1.96 (4H, m), 1.40–1.67 (6H, m) ppm.

LRMS (electrospray): m/z [M+H]$^+$ 538, [M−H]$^+$ 536.

Example 15

Methyl 3-endo-(8-{(3S)-3-(3-fluorophenyl)-3-[(3,3,3-trifluoropropanoyl)amino]propyl}-8-azabicyclo[3.2.1]oct-3-yl)-2-methyl-4,5,6,7-tetrahydro-3H-imidazo[4,5-c]pyridine-5-carboxylate

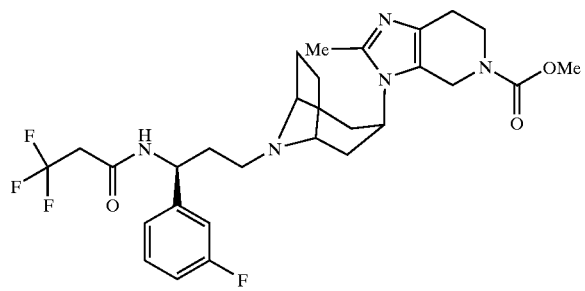

3,3,3-Trifluoropropanoic acid (0.043 g, 0.34 mmol), 1-hydroxybenzotriazole (0.056 g, 0.37 mmol), 1-(3-dimethylaminopropyl)-3-ethylcarbodiimide hydrochloride (0.076 g, 0.4 mmol) and methyl 3-endo-{8-[(3S)-3-amino-3-(3-fluorophenyl)propyl]-8-azabicyclo[3.2.1]oct-3-yl}-2-methyl-4,5,6,7-tetrahydro-3H-imidazo[4,5-c]pyridine-5-carboxylate (Preparation 21) (0.14 g, 0.31 mmol) were dissolved in dichloromethane (16 ml) under nitrogen at room temperature. The reaction was stirred at room temperature for 18 hours and quenched with saturated aqueous sodium hydrogencarbonate solution (20 ml). The organic phase was removed and dried (MgSO$_4$). The solvent was removed under reduced pressure to afford the title compound as an off-white solid (0.136 g).

$^1$H NMR (400 MHz, CDCl$_3$): δ: 7.23–7.32 (1H, m), 7.02–7.07 (1H, d), 6.92–6.97 (2H, m), 6.57–6.69 (1H, m), 5.14–5.22 (1H, m), 4.45–4.56 (2H, m), 4.12–4.23 (1H, m), 3.60–3.72 (5H, m), 3.26–3.36 (2H, m), 2.99–3.14 (2H, q), 2.56–2.62 (2H, m), 2.38–2.50 (2H, m), 2.37 (3H, s), 2.18–2.28 (2H, m), 2.01–2.13 (2H, m), 1.82–1.99 (2H, m), 1.41–1.65 (4H, m) ppm.

LRMS (electrospray): m/z [M+H]$^+$ 566, [M−H]$^+$ 564.

Example 16

Methyl 3-endo-(8-{(3S)-3-(3-fluorophenyl)-3-[(methoxycarbonyl)amino]propyl}-8-azabicyclo[3.2.1]oct-3-yl)-2-methyl-4,5,6,7-tetrahydro-3H-imidazo[4,5-c]pyridine-5-carboxylate

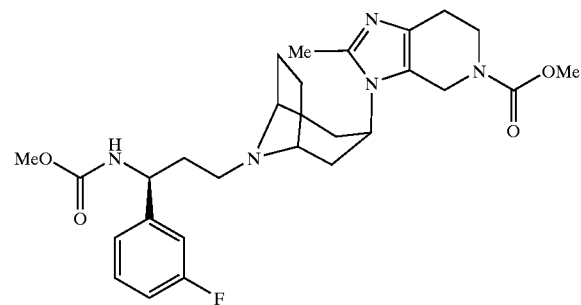

Methyl chloroformate (0.032 g, 0.34 mmol) was added to a solution of methyl 3-endo-{8-[(3S)-3-amino-3-(3-fluorophenyl)propyl]-8-azabicyclo[3.2.1]oct-3-yl}-2-methyl-4,5,6,7-tetrahydro-3H-imidazo[4,5-c]pyridine-5-carboxylate (Preparation 21) (0.14 g, 0.31 mmol) and N-ethyl-N,N-diisopropylamine (0.043 g, 0.34 mmol) dissolved in dichloromethane (16 ml) under nitrogen at room temperature. The reaction was stirred at room temperature for 18 hours and quenched with saturated aqueous sodium hydrogencarbonate solution (20 ml). The organic phase was removed and dried (MgSO$_4$). The solvent was removed under reduced pressure to afford the title compound as an off-white solid (0.125 g).

$^1$H NMR (400 MHz, CDCl$_3$): δ: 7.32–7.42 (1H, m), 7.23–7.32 (1H, m), 7.00–7.05 (1H, d), 6.95–7.00 (1H, d), 6.86–6.95 (1H, t), 4.82–4.92 (1H, m), 4.36–4.60 (3H, m), 3.58–3.73 (8H, m), 3.36–3.45 (1H, m), 3.23–3.32 (1H, m), 2.46–2.63 (4H, m), 2.39 (3H, s), 2.18–2.24 (2H, m), 1.92–2.18 (4H, m), 1.45–1.76 (4H, m) ppm.

LRMS (electrospray): m/z [M+H]$^+$ 514, [M−H]$^+$ 512.

Example 17

Methyl (1S)-3-[3-endo-(5-acetyl-2-methyl-4,5,6,7-tetrahydro-3H-imidazo[4,5-c]pyridin-3-yl)-8-azabicyclo[3.2.1]oct-8-yl]-1-(3-fluorophenyl)propylcarbamate

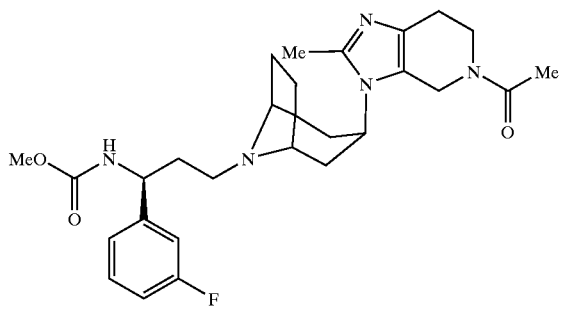

Methyl chloroformate (0.033 g, 0.35 mmol) was added to a solution of (1S)-3-[3-endo-(5-acetyl-2-methyl-4,5,6,7-tetrahydro-3H-imidazo[4,5-c]pyridin-3-yl)-8-azabicyclo[3.2.1]oct-8-yl]-1-(3-fluorophenyl)propylamine (Preparation 20) (0.14 g, 0.2 mmol) and N-ethyl-N,N-diisopropylamine (0.045 g, 0.35 mmol) dissolved in dichloromethane (16 ml) under nitrogen at room temperature. The reaction was stirred at room temperature for 18 hours and quenched with saturated aqueous sodium hydrogencarbonate solution (10 ml). The product was extracted from the organic phase with 2N HCl (3×3 ml) and the aqueous phase was basified to pH 10 using 2N NaOH. This was then extracted with dichloromethane (3×5 ml) and the combined organic extracts were dried (MgSO$_4$). The solvent was removed under reduced pressure to afford the title compound as an off-white solid (0.133 g).

$^1$H NMR (400 MHz, CDCl$_3$): δ: 7.33–7.43 (1H, m), 7.23–7.30 (1H, m), 7.01–7.05 (1H, d), 6.93–6.99 (1H, d), 6.86–6.91 (1H, t), 4.82–4.92 (1H, m), 4.65 (2H, s), 4.37–4.52 (1H, m), 3.56–3.66 (5H, m), 3.36–3.46 (1H, m), 3.25–3.36 (1H, m), 2.45–2.63 (2H, t), 2.40 (3H, s), 2.18–2.26 (2H, t), 2.15 (3H, s), 1.91–2.10 (2H, m), 1.49–1.77 (6H, m) ppm.

LRMS (electrospray): m/z [M+H]$^+$ 498, [M–H]$^+$ 496.

Example 18

N-[(1S)-3-[3-endo-(5-Acetyl-2-methyl-4,5,6,7-tetrahydro-3H-imidazo[4,5-c]pyridin-3-yl)-8-azabicyclo[3.2.1]oct-8-yl]-1-(3-fluorophenyl)propyl]cyclobutanecarboxamide

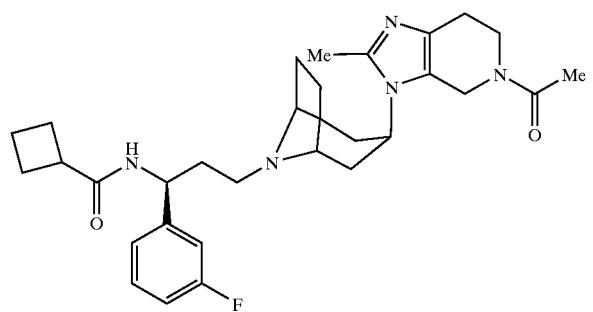

Cyclobutylcarbonyl chloride (0.041 g, 0.35 mmol) was added to a solution of (1S)-3-[3-endo-(5-acetyl-2-methyl-4,5,6,7-tetrahydro-3H-imidazo[4,5-c]pyridin-3-yl)-8-azabicyclo[3.2.1]oct-8-yl]-1-(3-fluorophenyl)propylamine (Preparation 20) (0.14 g, 0.2 mmol) and N-ethyl-N,N-diisopropylamine (0.045 g, 0.35 mmol) dissolved in dichloromethane (16 ml) under nitrogen at room temperature. The reaction was stirred at room temperature for 18 hours and quenched with saturated aqueous sodium hydrogencarbonate solution (10 ml). The product was extracted from the organic phase with 2N HCl (3×3 ml) and the aqueous phase was basified to pH 10 using 2N NaOH. This was then extracted with dichloromethane (3×5 ml) and the combined organic extracts were dried (MgSO$_4$). The solvent was removed under reduced pressure to afford the title compound as a white foam (0.124 g) which was a mixture of rotamers.

$^1$H NMR (400 MHz, CDCl$_3$): δ: 7.22–7.29 (1H, m), 7.02–7.07 (1H, d), 6.87–6.97 (2H, m), 6.09–6.13 (0.83H, d), 5.82–5.86 (0.17H, d), 5.15–5.22 (0.17H, m), 5.03–5.13 (0.83H, m), 4.62 (2H, s), 4.35–4.57 (1H, m), 3.73–3.87 (0.34H, m), 3.60–3.67 (1.66H, t), 3.25–3.34 (2H, m), 2.90–3.00 (1H, m), 2.55–2.68 (2H, m), 2.35–2.51 (5H, m), 2.00–2.25 (13H, m), 21.80–1.98 (2H, m), 1.56–1.67 (2H, m), 1.40–1.56 (2H, m) ppm.

LRMS (electrospray): m/z [M+H]$^+$ 522, [M–H]$^+$ 520.

Example 19

N-[(1S)-3-[3-endo-(5-Acetyl-2-methyl-4,5,6,7-tetrahydro-3H-imidazo[4,5-c]pyridin-3-yl)-8-azabicyclo[3.2.1]oct-8-yl]-1-(3-fluorophenyl)propyl]-3,3,3-trifluoropropanamide

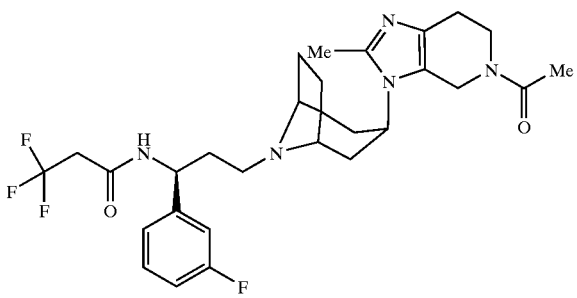

3,3,3-Trifluoropropanoic acid (0.045 g, 0.35 mmol), 1-hydroxybenzotriazole (0.058 g, 0.38 mmol), 1-(3-dimethylaminopropyl)-3-ethylcarbodiimide hydrochloride (0.079 g, 0.41 mmol) and (1S)-3-[3-endo-(5-acetyl-2-methyl-4,5,6,7-tetrahydro-3H-imidazo[4,5-c]pyridin-3-yl)-8-azabicyclo[3.2.1]oct-8-yl]-1-(3-fluorophenyl)propylamine (Preparation 20) (0.140 g, 0.31 mmol) were dissolved in dichloromethane (16 ml) under nitrogen at room temperature. The reaction was stirred at room temperature for 18 hours and quenched with saturated aqueous sodium hydrogencarbonate solution (20 ml). The organic phase was removed and dried (MgSO$_4$). The solvent was removed under reduced pressure to afford the title compound as an off-white solid (0.136 g) which was a mixture of rotamers.

$^1$H NMR (400 MHz, CDCl$_3$): δ: 7.22–7.33 (1H, m), 7.02–7.07 (1H, d), 6.92–6.98 (2H, m), 6.66–6.72 (0.85H, d), 6.36–6.42 (0.15H, d), 5.27–5.34 (0.15H, m), 5.13–5.19 (0.85H, m), 4.61 (2H, s), 4.35–4.53 (1H, m), 3.68–3.88 (0.3H, m), 3.60–3.66 (1.7H, t), 3.25–3.37 (2H, m), 2.62–2.67 (1.7H, m), 2.53–2.61 (0.3H, m), 2.35–2.50 (5H, m), 2.17–2.25 (2H, m), 2.13 (3H, s), 2.00–2.11 (2H, m), 1.82–1.99 (2H, m), 1.56–1.65 (2H, m), 1.40–1.57 (2H, m) ppm.

LRMS (electrospray): m/z [M+H]$^+$ 550, [M–H]$^+$ 548.

Example 20

N-[(1S)-3-[3-endo-(5-Acetyl-2-methyl-4,5,6,7-tetrahydro-3H-imidazo[4,5-c]pyridin-3-yl)-8-azabicyclo[3.2.1]oct-8-yl]-1-(3-fluorophenyl)propyl]tetrahydro-pyran-4-carboxamide

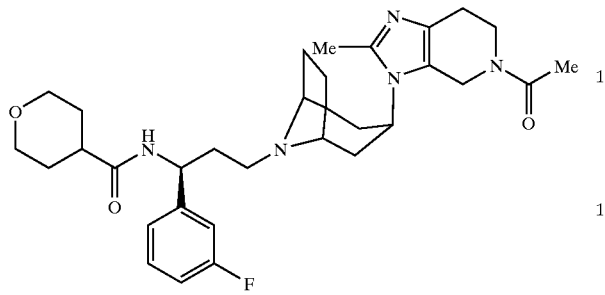

Tetrahydropyran-4-carboxylic acid (0.046 g, 0.35 mmol), 1-hydroxybenzotriazole (0.058 g, 0.38 mmol), 1-(3-dimethylaminopropyl)-3-ethylcarbodiimide hydrochloride (0.079 g, 0.41 mmol) and (1S)-3-[3-endo-(5-acetyl-2-methyl-4,5,6,7-tetrahydro-3H-imidazo[4,5-c]pyridin-3-yl)-8-azabicyclo[3.2.1]oct-8-yl]-1-(3-fluorophenyl)propylamine (Preparation 20) (0.14 g, 0.31 mmol) were dissolved in dichloromethane (16 ml) under nitrogen at room temperature. The reaction was stirred at room temperature for 18 hours and quenched with saturated aqueous sodium hydrogencarbonate solution (20 ml). The organic phase was removed and dried (MgSO₄). The solvent was removed under reduced pressure to afford the title compound as an off-white solid (0.145 g) which was a mixture of rotamers.

$^1$H NMR (400 MHz, CDCl$_3$): δ: 7.22–7.35 (1H, m), 7.02–7.08 (1H, m), 6.88–7.01 (2H, m), 5.93–6.04 (0.85H, d), 5.75–5.82 (0.15H, d), 5.16–5.25 (0.15H, m), 5.04–5.15 (0.85H, q), 4.62 (2H, s), 4.33–4.57 (1H, m), 3.92–4.02 (2H, m), 3.73–3.89 (0.3H, m), 3.60–3.71 (1.7H, m), 3.22–3.42 (4H, m), 2.36–2.48 (2H, m), 2.23–2.57 (7H, m), 2.12–2.23 (5H, m), 1.97–2.10 (2H, m), 1.84–1.96 (2H, m), 1.39–1.84 (7H, m) ppm.

LRMS (electrospray): m/z [M+H]⁺ 552, [M–H]⁺ 550.

Example 21

N-((1S)-3-{3-endo-[2-Methyl-5-(3,3,3-trifluoropropanoyl)-4,5,6,7-tetrahydro-3H-imidazo[4,5-c]pyridin-3-yl]-8-azabicyclo[3.2.1]oct-8-yl}-1-phenylpropyl)tetrahydro-pyran-4-carboxamide

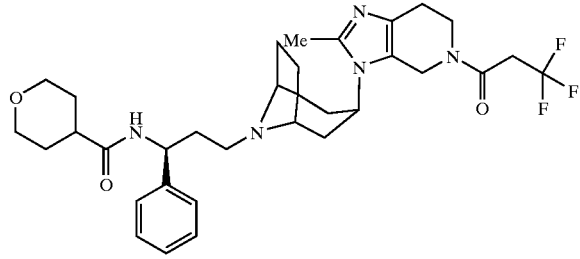

1-(3-Dimethylaminopropyl)-3-ethylcarbodiimide hydrochloride (0.035 g, 0.18 mmol) was added to a solution of tetrahydropyran-4-carboxylic acid (0.022 g, 0.17 mmol), (1S)-3-{3-endo-[2-methyl-5-(3,3,3-trifluoropropanoyl)-4,5,6,7-tetrahydro-3H-imidazo[4,5-c]pyridin-3-yl]-8-azabicyclo[3.2.1]oct-8-yl}-1-phenylpropylamine (Preparation 24) (0.075 g, 0.15 mmol), triethylamine (0.03 ml, 0.22 mmol) and 1-hydroxybenzotriazole (0.027 g, 0.18 mmol) dissolved in dichloromethane (3 ml) under nitrogen at room temperature and stirred for 18 hours. The solvent was removed under reduced pressure and the residue was purified by flash column chromatography on silica gel eluting with a solvent gradient of dichloromethane:methanol:concentrated aqueous ammonia (95:5:0.5, by volume, changing to 92:8:0.5). Product containing fractions were evaporated to afford the title compound as a white foam (0.075 g) which was a mixture of rotamers.

$^1$H NMR (400 MHz, CDCl$_3$): δ: 7.32–7.38 (2H, m), 7.23–7.32 (3H, m), 5.82–5.89 (0.85H, d), 5.66–5.72 (0.15H, d), 5.39–5.45 (0.15H, m), 5.11–5.17 (0.85H, q), 4.70 (1.7H, s), 4.67 (0.3H, s), 4.39–4.55 (1H, m), 3.93–4.04 (2H, m), 3.72–3.80 (0.3H, m), 3.65–3.71 (1.7H, m), 3.25–3.43 (6H, m), 2.62–2.74 (2H, m), 2.15–2.50 (8H, m), 2.00–2.13 (2H, m), 1.85–2.00 (2H, m), 1.64–1.84 (4H, m), 1.43–1.63 (4H, m) ppm.

LRMS (electrospray): m/z [M+H]⁺ 602, [M–H]⁺ 600.

Found C, 62.85; H, 7.10; N, 11.42. C$_{32}$H$_{42}$F$_3$N$_5$O$_3$. 0.5 mol H$_2$O requires C, 62.93; H, 7.10; N, 11.47%.

Example 22

3,3,3-Trifluoro-N-((1S)-3-{3-endo-[2-methyl-5-(3,3,3-trifluoropropanoyl)-4,5,6,7-tetrahydro-3H-imidazo[4,5-c]pyridin-3-yl]-8-azabicyclo[3.2.1]oct-8-yl}-1-phenylpropyl)propanamide

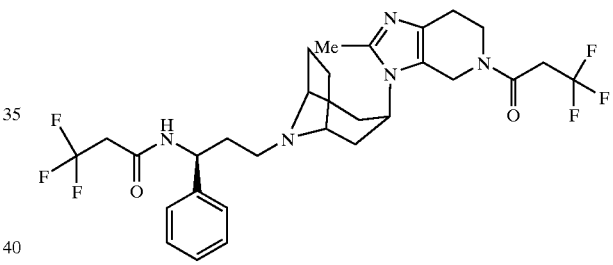

1-(3-Dimethylaminopropyl)-3-ethylcarbodiimide hydrochloride (0.035 g, 0.18 mmol) was added to a solution of 3,3,3-trifluoropropanoic acid (0.022 g, 0.17 mmol), (1S)-3-{3-endo-[2-methyl-5-(3,3,3-trifluoropropanoyl)-4,5,6,7-tetrahydro-3H-imidazo[4,5-c]pyridin-3-yl]-8-azabicyclo[3.2.1]oct-8-yl}-1-phenylpropylamine (Preparation 24) (0.075 g, 0.15 mmol), triethylamine (0.03 ml, 0.22 mmol) and 1-hydroxybenzotriazole (0.027 g, 0.18 mmol) dissolved in dichloromethane (3 ml) under nitrogen at room temperature and stirred for 18 hours. The solvent was removed under reduced pressure and the residue was purified by flash column chromatography on silica gel eluting with a solvent gradient of dichloromethane:methanol:concentrated aqueous ammonia (95:5:0.5, by volume, changing to 92:8:0.5). Product containing fractions were evaporated to afford the title compound as a white foam (0.075 g) which was a mixture of rotamers.

$^1$H NMR (400 MHz, CDCl$_3$): δ: 7.32–7.38 (2H, m), 7.22–7.31 (3H, m), 6.39–6.47 (0.8H, d), 6.08–6.18 (0.2H, d), 5.51–5.59 (0.2H, q), 5.18–5.25 (0.8H, q), 4.70 (1.6H, s), 4.66 (0.4H, s), 4.40–4.55 (1H, m), 4.06–4.16 (0.2H, m), 3.63–3.71 (1.8H, t), 3.25–3.36 (4H, m), 3.00–3.14 (2H, m), 2.58–2.72 (2H, m), 2.36–2.50 (5H, m), 2.18–2.35 (2H, m), 2.01–2.17 (2H, m), 1.94–2.01 (2H, m), 1.43–1.63 (4H, m) ppm.

LRMS (electrospray): m/z [M+H]⁺ 600, [M–H]⁺ 598.

Found C, 57.51; H, 5.91; N, 11.47. $C_{29}H_{35}F_6N_5O_2$. 0.25 mol $H_2O$ requires C, 57.66; H, 5.92; N, 11.59%.

Example 23

N-((1S)-3-{3-endo-[2-Methyl-5-(3,3,3-trifluoropropanoyl)-4,5,6,7-tetrahydro-3H-imidazo[4,5-c]pyridin-3-yl]-8-azabicyclo[3.2.1]oct-8-yl}-1-phenylpropyl)cyclobutanecarboxamide

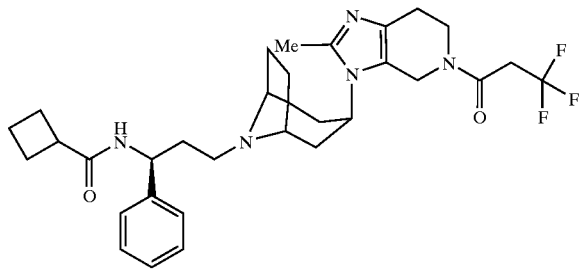

Cyclobutylcarbonyl chloride (0.02 ml, 0.17 mmol) was added to a solution of (1S)-3-{3-endo-[2-methyl-5-(3,3,3-trifluoropropanoyl)-4,5,6,7-tetrahydro-3H-imidazo[4,5-c]pyridin-3-yl]-8-azabicyclo[3.2.1]oct-8-yl}-1-phenylpropylamine (Preparation 24) (0.075 g, 0.15 mmol) and triethylamine (0.03 ml, 0.22 mmol) dissolved in dichloromethane (3 ml) under nitrogen at room temperature. The reaction was stirred at room temperature for 1.5 hours, and the solvent was removed under reduced pressure. The residue was purified by flash column chromatography on silica gel eluting with a solvent gradient of dichloromethane:methanol:concentrated aqueous ammonia (95:5:0.5, by volume, changing to 92:8:0.5). Product containing fractions were evaporated to afford the title compound as a white foam (0.068 g) which was a mixture of rotamers.

¹H NMR (400 MHz, CDCl₃): δ: 7.32–7.39 (2H, m), 7.22–7.31 (3H, m), 5.86–5.93 (0.87H, d), 5.60–5.64 (0.13H, d), 5.36–5.43 (0.13H, m), 5.09–5.16 (0.87H, q), 4.72 (1.8H, s), 4.69 (0.2H, s), 4.39–4.56 (1H, m), 3.64–3.71 (2H, t), 3.25–3.36 (4H, m), 2.93–3.03 (1H, m), 2.62–2.75 (2H, m), 2.34–2.52 (5H, m), 2.00–2.33 (8H, m), 1.82–2.00 (4H, m), 1.41–1.61 (4H, m) ppm.

LRMS (electrospray): m/z [M–H]⁺ 570.

Found C, 64.30; H, 7.11; N, 12.02. $C_{31}H_{40}F_3N_5O_2$. 0.5 mol $H_2O$ requires C, 64.12; H, 7.12; N, 12.06%.

Example 24

Methyl(1S)-3-{3-endo-[2-methyl-5-(3,3,3-trifluoropropanoyl)-4,5,6,7-tetrahydro-3H-imidazo[4,5-c]pyridin-3-yl]-8-azabicyclo[3.2.1]oct-8-yl}-1-phenylpropylcarbamate

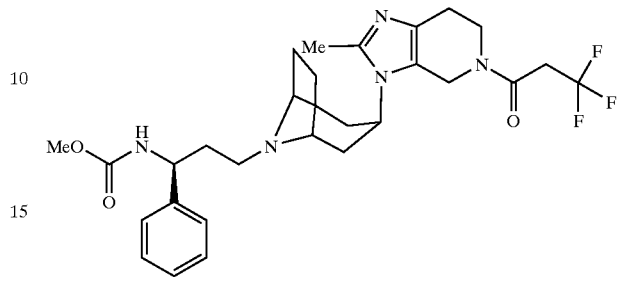

Methyl chloroformate (0.015 ml, 0.19 mmol) was added to a solution of (1S)-3-{3-endo-[2-methyl-5-(3,3,3-trifluoropropanoyl)-4,5,6,7-tetrahydro-3H-imidazo[4,5-c]pyridin-3-yl]-8-azabicyclo[3.2.1]oct-8-yl}-1-phenylpropylamine (Preparation 24) (0.075 g, 0.15 mmol) and triethylamine (0.03 ml, 0.22 mmol) dissolved in dichloromethane (3 ml) under nitrogen at room temperature. The reaction was stirred at room temperature for 1.5 hours, and the solvent was removed under reduced pressure. The residue was purified by flash column chromatography on silica gel eluting with a solvent gradient of dichloromethane:methanol:concentrated aqueous ammonia (95:5:0.5, by volume, changing to 92:8:0.5). Product containing fractions were evaporated to afford the title compound as a white foam (0.062 g).

¹H NMR (400 MHz, CDCl₃): δ: 7.33–7.40 (2H, m), 7.21–7.33 (3H, m), 7.04–7.18 (1H, m), 4.82–4.96 (1H, m), 4.73 (2H, s), 4.43–4.60 (1H, m), 3.64–3.73 (1H, t), 3.46–3.64 (4H, m), 3.39–3.47 (1H, m), 3.26–3.38 (3H, m), 2.62–2.77 (2H, m), 2.49–2.59 (2H, m), 2.43 (3H, s), 2.19–2.30 (2H, m), 1.92–2.08 (4H, m), 1.48–1.68 (4H, m) ppm.

LRMS (electrospray): m/z [M+H]⁺ 548, [M–H]⁺ 546.

Found C, 60.47; H, 6.68; N, 12.45. $C_{28}H_{36}F_3N_5O_3$. 0.5 mol $H_2O$ requires C, 60.42; H, 6.70; N, 12.58%.

Example 25

Methyl 3-endo-(8-{(3S)-3-[(methoxycarbonyl)amino]-3-phenylpropyl}-8-azabicyclo[3.2.1]oct-3-yl)-2-methyl-4,5,6,7-tetrahydro-3H-imidazo[4,5-c]pyridine-5-carboxylate

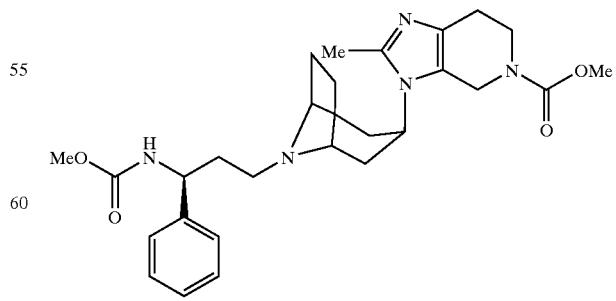

Methyl chloroformate (0.015 ml, 0.19 mmol) was added to a solution of methyl 3-endo-{8-[(3S)-3-amino-3- phenylpropyl]-8-azabicyclo[3.2.1]oct-3-yl}-2-methyl-4,5,6,7-tetrahydro-3H-imidazo[4,5-c]pyridine-5-carboxylate (Preparation 26) (0.06 g, 0.14 mmol) and triethylamine (0.03 ml, 0.22 mmol) dissolved in dichloromethane (3 ml) under nitrogen at room temperature. The reaction was stirred at room temperature for 18 hours and the solvent was removed under reduced pressure. The residue was purified by flash column chromatography on silica gel eluting with a solvent gradient of dichloromethane:methanol:concentrated aqueous ammonia (94:6:0.6, by volume, changing to 92:8:0.8). Product containing fractions were evaporated to afford the title compound as a white foam (0.058 g).

$^1$H NMR (400 MHz, CDCl$_3$): δ: 7.22–7.38 (6H, m), 4.87–4.94 (1H, m), 4.42–4.63 (3H, m), 3.65–3.75 (5H, m), 3.62 (3H, s), 3.41–3.47 (1H, t), 3.28–3.37 (1H, m), 2.60–2.66 (2H, m), 2.49–2.60 (2H, m), 2.43 (3H, s), 2.20–2.27 (2H, m), 1.96–2.20 (4H, m), 1.72–1.82 (1H, m), 1.48–1.69 (3H, m) ppm.

LRMS (electrospray): m/z [M+H]$^+$ 496, [M–H]$^+$ 494.

Found C, 64.34; H, 7.66; N, 13.79. C$_{27}$H$_{37}$N$_5$O$_4$. 0.5 mol H$_2$O requires C, 64.26; H, 7.59; N, 13.88%.

Example 26

Methyl 2-methyl-3-endo-(8-{(3S)-3-phenyl-3-[(3,3,3-trifluoropropanoyl)amino]propyl}-8-azabicyclo[3.2.1]oct-3-yl)-4,5,6,7-tetrahydro-3H-imidazo[4,5-c]pyridine-5-carboxylate

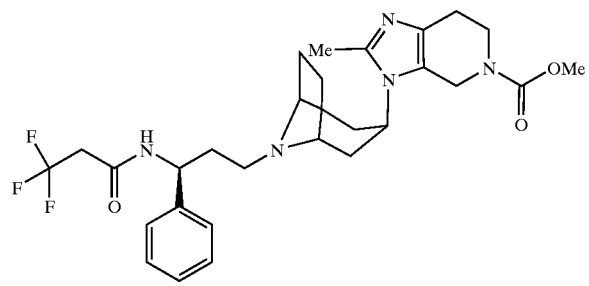

1-(3-Dimethylaminopropyl)-3-ethylcarbodiimide hydrochloride (0.04 g, 0.21 mmol) was added to a solution of 3,3,3-trifluoropropanoic acid (0.015 ml, 0.16 mmol), methyl 3-endo-{8-[(3S)-3-amino-3-phenylpropyl]-8-azabicyclo[3.2.1]oct-3-yl}-2-methyl-4,5,6,7-tetrahydro-3H-imidazo[4,5-c]pyridine-5-carboxylate (Preparation 26) (0.06 g, 0.14 mmol), triethylamine (0.03 ml, 0.22 mmol) and 1-hydroxybenzotriazole (0.03 g, 0.20 mmol) dissolved in dichloromethane (3 ml) under nitrogen at room temperature. The reaction was held at room temperature for 18 hours. The solvent was removed under reduced pressure and the residue was purified by flash column chromatography on silica gel eluting with a solvent gradient of dichloromethane:methanol:concentrated aqueous ammonia (94:6:0.6, by volume, changing to 92:8:0.6). Product containing fractions were evaporated to afford the title compound as a white foam (0.071 g).

$^1$H NMR (400 MHz, CDCl$_3$): δ: 7.28–7.36 (2H, m), 7.22–7.27 (3H, m), 6.37–6.50 (1H, d), 5.14–5.23 (1H, m), 4.51 (2H, s), 4.34–4.46 (1H, m), 3.60–3.68 (2H, m), 3.70 (3H, s), 3.27–3.33 (2H, m), 2.98–3.10 (2H, m), 2.57–2.64 (2H, m), 2.34–2.52 (5H, m), 2.18–2.27 (2H, m), 2.00–2.10 (2H, m), 1.91–2.00 (2H, m), 1.40–1.60 (4H, m) ppm.

LRMS (electrospray): m/z [M+H]$^+$ 548, [M–H]$^+$ 546.

Found C, 59.99; H, 6.69; N, 12.49. C$_{28}$H$_{36}$F$_3$N$_5$O$_3$. 0.75 mol H$_2$O requires C, 59.93; H, 6.74; N, 12.48%.

Example 27

Methyl(1S)-3-[3-endo-(5-acetyl-2-methyl-4,5,6,7-tetrahydro-3H-imidazo[4,5-c]pyridin-3-yl)-8-azabicyclo[3.2.1]oct-8-yl]-1-phenylpropylcarbamate

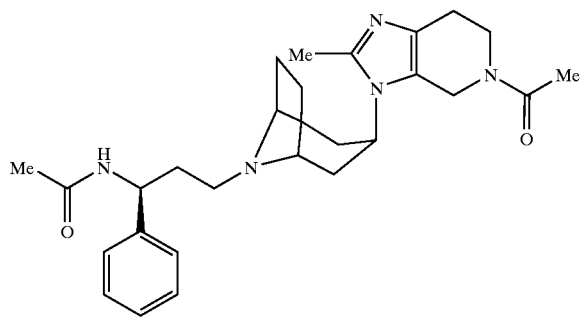

Methyl chloroformate (0.027 ml, 0.35 mmol) was added to a solution of (1S)-3-[3-endo-(5-acetyl-2-methyl-4,5,6,7-tetrahydro-3H-imidazo[4,5-c]pyridin-3-yl)-8-azabicyclo[3.2.1]oct-8-yl]-1-phenylpropylamine (Preparation 28) (0.125 g, 0.30 mmol) and triethylamine (0.06 ml, 0.43 mmol) dissolved in dichloromethane (5 ml) under nitrogen at room temperature. The reaction was stirred at room temperature for 1.5 hours and the solvent was removed under reduced pressure. The residue was purified by flash column chromatography on silica gel eluting with a solvent gradient of dichloromethane:methanol:concentrated aqueous ammonia (94:6:0.6, by volume, changing to 92:8:0.6). Product containing fractions were evaporated to afford the title compound as a white foam (0.125 g).

$^1$H NMR (400 MHz, CDCl$_3$): δ: 7.19–7.34 (5H, m), 7.10–7.18 (1H, m), 4.82–4.92 (1H, m), 4.63 (2H, s), 4.40–4.53 (1H, m), 3.57–3.68 (5H, m), 3.37–3.44 (1H, m), 3.24–3.35 (1H, m), 2.57–2.68 (2H, m), 2.44–2.56 (2H, m), 2.40 (3H, s), 2.17–2.25 (2H, m), 1.92–2.16 (7H, m), 1.43–1.66 (4H, m) ppm.

LRMS (electrospray): m/z [M+H]$^+$ 480.

Found C, 66.26; H, 7.87; N, 14.30. C$_{27}$H$_{37}$N$_5$O$_3$. 0.5 mol H$_2$O requires C, 66.37; H, 7.84; N, 14.33%.

Example 28

N-{(1S)-3-[3-endo-(5-Acetyl-2-methyl-4,5,6,7-tetrahydro-3H-imidazo[4,5-c]pyridin-3-yl)-8-azabicyclo[3.2.1]oct-8-yl]-1-phenylpropyl}-3,3,3-trifluoropropanamide

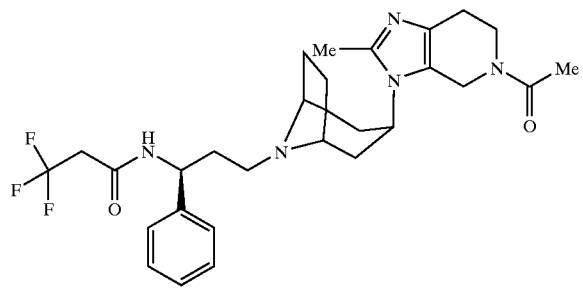

1-(3-Dimethylaminopropyl)-3-ethylcarbodiimide hydrochloride (0.077 g, 0.4 mmol) was added to a solution of 3,3,3-trifluoropropanoic acid (0.03 ml, 0.34 mmol), (1S)-3-

[3-endo-(5-acetyl-2-methyl-4,5,6,7-tetrahydro-3H-imidazo[4,5-c]pyridin-3-yl)-8-azabicyclo[3.2.1]oct-8-yl]-1-phenylpropylamine (Preparation 28) (0.125 g, 0.3 mmol), triethylamine (0.07 ml, 0.5 mmol) and 1-hydroxybenzotriazole (0.061 g, 0.40 mmol) dissolved in dichloromethane (5 ml) under nitrogen at room temperature. The reaction was held at room temperature for three hours. The solvent was removed under reduced pressure and the residue was purified by flash column chromatography on silica gel eluting with a solvent gradient of dichloromethane:methanol:concentrated aqueous ammonia (94:6:0.6, by volume, changing to 92:8:0.6 then 90:10:0.6). Product containing fractions were evaporated to afford the title compound as a white foam (0.14 g) which was a mixture of rotamers.

$^1$H NMR (400 MHz, CDCl$_3$): δ: 7.32–7.40 (2H, m), 7.27–7.31 (3H, m), 6.50–6.58 (0.85H, d), 6.27–6.32 (0.15H, d), 5.31–5.58 (0.15H, m), 5.17–5.24 (0.85H, q), 4.64 (2H, s), 4.38–4.60 (1H, m), 3.75–3.87 (0.3H, m), 3.63–3.71 (1.7H, t), 3.30–3.39 (2H, m), 3.01–3.13 (2H, m), 2.60–2.64 (0.3H, m), 2.64–2.70 (1.7H, t), 2.37–2.52 (5H, m), 2.20–2.30 (2H, t), 2.17 (3H, s), 2.01–2.13 (2H, m), 1.92–2.01 (2H, m), 1.45–1.65 (4H, m) ppm.

LRMS (electrospray): m/z [M+Na]$^+$ 554, [M+H]$^+$ 532, [M−H]$^+$ 530.

Found C, 62.24; H, 6.90; N, 13.12. C$_{28}$H$_{36}$F$_3$N$_5$O$_2$. 0.5 mol H$_2$O requires C, 62.21; H, 6.90; N, 12.95%.

Example 29

Methyl 1-endo-{8-[(3S)-3-(acetamido)-3-phenylpropyl]-8-azabicyclo[3.2.1]oct-3-yl}-2-methyl-4,5,6,7-tetrahydro-1H-imidazo[4,5-c]pyridine-5-carboxylate

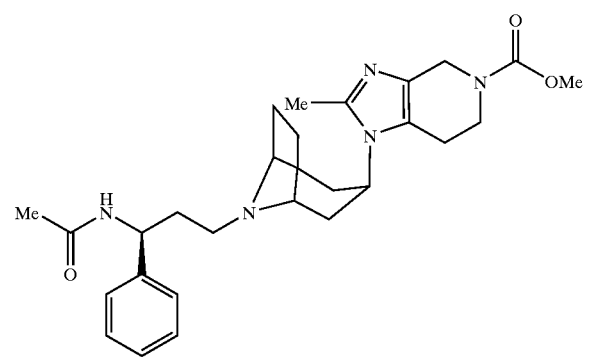

Acetyl chloride (0.02 g, 0.25 mmol) was added to a solution of methyl 1-endo-{8-[(3S)-3-amino-3-phenylpropyl]-8-azabicyclo[3.2.1]oct-3-yl}-2-methyl-4,5,6,7-tetrahydro-1H-imidazo[4,5-c]pyridine-5-carboxylate trihydrochloride (Preparation 36) (0.125 g, 0.23 mmol) and N-ethyl-N,N-diisopropylamine (0.103 g, 0.8 mmol) dissolved in dichloromethane (4 ml) under nitrogen at room temperature and the reaction mixture stirred for 18 hours. Dichloromethane (5 ml) was added and the solution washed with saturated aqueous sodium hydrogencarbonate solution (10 ml) and brine (10 ml). The organic phase was dried (MgSO$_4$) and solvent removed under reduced pressure. The residue was purified by flash column chromatography on silica gel eluting with a solvent gradient of dichloromethane:methanol:concentrated aqueous ammonia (98:2:0.2, by volume, changing to 97:3:0.3). Product containing fractions were evaporated to afford the title compound as a white foam (0.09 g).

$^1$H NMR (400 MHz, CDCl$_3$): δ: 7.40–7.25 (5H, m), 6.30–6.20 (1H, d), 5.20–5.10 (1H, q), 4.50–4.35 (3H, m), 3.80–3.60 (5H, m), 3.35 (2H, m), 2.80–2.60 (2H, m), 2.50–2.40 (5H, m), 2.30–1.90 (7H, m), 1.70–1.45 (6H, m) ppm.

LRMS (electrospray): m/z [M+H]$^+$ 480, [M−H]$^+$ 478.

Example 30

Methyl 1-endo-(8-{(3S)-3-[(methoxycarbonyl)amino]-3-phenylpropyl}-8-azabicyclo[3.2.1]oct-3-yl)-2-methyl-4,5,6,7-tetrahydro-1H-imidazo[4,5-c]pyridine-5-carboxylate

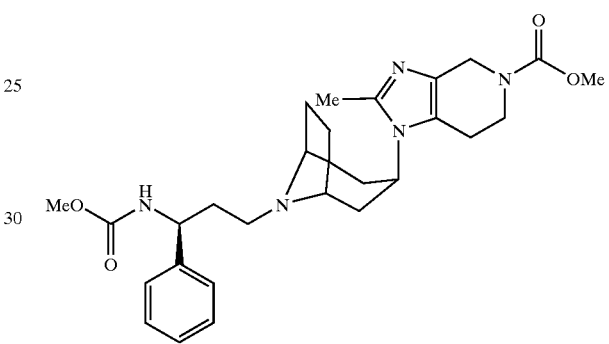

Methyl chloroformate (0.024 g, 0.25 mmol) was added to a solution of methyl 1-endo-{8-[(3S)-3-amino-3-phenylpropyl]-8-azabicyclo[3.2.1]oct-3-yl}-2-methyl-4,5,6,7-tetrahydro-1H-imidazo[4,5-c]pyridine-5-carboxylate trihydrochloride (Preparation 36) (0.125 g, 0.23 mmol) and N-ethyl-N,N-diisopropylamine (0.118 g, 0.91 mmol) dissolved in dichloromethane (4 ml) under nitrogen at room temperature and the reaction mixture stirred for 18 hours. Dichloromethane (5 ml) was added and the solution washed with saturated aqueous sodium hydrogencarbonate solution (10 ml) and brine (10 ml). The organic phase was dried (MgSO$_4$) and solvent removed under reduced pressure. The residue was purified by flash column chromatography on silica gel eluting with a solvent gradient of dichloromethane:methanol:concentrated aqueous ammonia (99:1:0.1, by volume, changing to 98:2:0.2). Product containing fractions were evaporated to afford the title compound as a white foam (0.07 g).

$^1$H NMR (400 MHz, CDCl$_3$): δ: 7.40–7.10 (6H, m), 5.00–4.80 (1H, m), 4.60–4.40 (3H, m), 3.80–3.60 (8H, m), 3.50–3.30 (2H, m), 2.80–2.65 (2H, m), 2.60–2.40 (5H, m), 2.30–1.95 (6H, m), 1.85–1.50 (4H, m) ppm.

LRMS (electrospray): m/z [M+H]$^+$ 496.

Example 31

Methyl 1-endo-(8-{(3S)-3-[(cyclobutylcarbonyl)amino]-3-phenylpropyl}-8-azabicyclo[3.2.1]oct-3-yl)-2-methyl-4,5,6,7-tetrahydro-1H-imidazo[4,5-c]pyridine-5-carboxylate

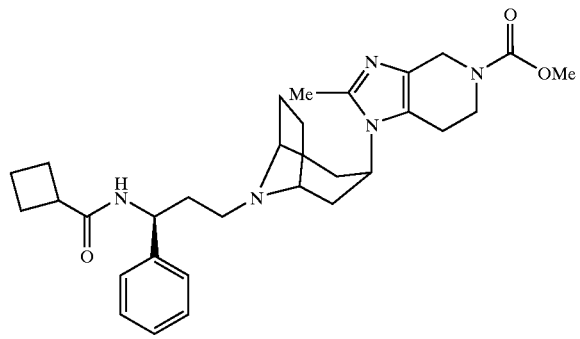

Cyclobutylcarbonyl chloride (0.03 g, 0.25 mmol) was added to a solution of methyl 1-endo-{8-[(3S)-3-amino-3-phenylpropyl]-8-azabicyclo[3.2.1]oct-3-yl}-2-methyl-4,5,6,7-tetrahydro-1H-imidazo[4,5-c]pyridine-5-carboxylate trihydrochloride (Preparation 36) (0.125 g, 0.23 mmol) and N-ethyl-N,N-diisopropylamine (0.118 g, 0.91 mmol) dissolved in dichloromethane (4 ml) under nitrogen at room temperature and the reaction mixture stirred for 18 hours. Dichloromethane (5 ml) was added and the solution washed with saturated aqueous sodium hydrogencarbonate solution (10 ml) and brine (10 ml). The organic phase was dried (MgSO$_4$) and solvent removed under reduced pressure. The residue was purified by flash column chromatography on silica gel eluting with a solvent gradient of dichloromethane:methanol:concentrated aqueous ammonia (99:1:0.1, by volume, changing to 98:2:0.2). Product containing fractions were evaporated to afford the title compound as a white foam (0.08 g).

$^1$NMR (400 MHz, CDCl$_3$): δ: 7.40–7.20 (5H, m), 6.10–6.00 (1H, d), 5.20–5.10 (1H, q), 4.50–4.35 (3H, m), 3.80–3.60 (5H, m), 3.40–3.30 (2H, m), 3.00 (1H, qu), 2.80–2.65 (2H, m), 2.50–1.50 (21H, m) ppm.

LRMS (electrospray): m/z [M+H]$^+$ 520.

Example 32

Methyl 2-methyl-1-endo-(8-{(3S)-3-phenyl-3-[(3,3,3-trifluoropropanoyl)amino]propyl}-8-azabicyclo[3.2.1]oct-3-yl)-4,5,6,7-tetrahydro-1H-imidazo[4,5-c]pyridine-5-carboxylate

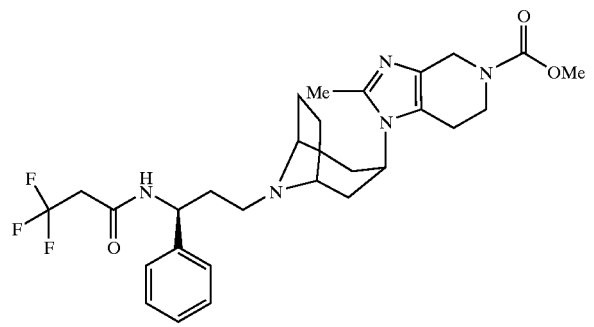

1-(3-Dimethylaminopropyl)-3-ethylcarbodiimide hydrochloride (0.056 g, 0.3 mmol) was added to a solution of 3,3,3-trifluoropropanoic acid (0.022 ml, 0.25 mmol), methyl 1-endo-{8-[(3S)-3-amino-3-phenylpropyl]-8-azabicyclo[3.2.1]oct-3-yl}-2-methyl-4,5,6,7-tetrahydro-1H-imidazo[4,5-c]pyridine-5-carboxylate trihydrochloride (Preparation 36) (0.125 g, 0.23 mmol), N-ethyl-N,N-diisopropylamine (0.16 ml, 0.91 mmol) and 1-hydroxybenzotriazole (0.042 g, 0.27 mmol) dissolved in dichloromethane (4 ml) under nitrogen at room temperature. The reaction was held at room temperature for two hours. Dichloromethane (5 ml) was added and the solution washed with saturated aqueous sodium hydrogencarbonate solution (10 ml) and brine (10 ml). The organic phase was dried (MgSO$_4$) and solvent removed under reduced pressure. The residue was purified by flash column chromatography on silica gel eluting with a solvent gradient of dichloromethane:methanol:concentrated aqueous ammonia (99:1:0.1, by volume, changing to 98:2:0.2). Product containing fractions were evaporated to afford the title compound as a white foam (0.077 g).

$^1$H NMR (400 MHz, CDCl$_3$): δ: 7.40–7.25 (5H, m), 6.60 (1H, d), 5.20 (1H, q), 4.50–4.35 (3H, m), 3.80–3.70 (5H, m), 3.35 (2H, m), 3.15–3.00 (2H, q), 2.80–2.60 (2H, m), 2.50–2.40 (5H, m), 2.30–1.90 (6H, m), 1.65–1.50 (4H, m) ppm.

LRMS (electrospray): m/z [M+Na]$^+$ 570, [M+H]$^+$ 548, [M–H]$^+$ 546.

Example 33

Methyl 1-endo-{8-[(3S)-3-(acetylamino)-3-(3-fluorophenyl)propyl]-8-azabicyclo[3.2.1]oct-3-yl}-2-methyl-4,5,6,7-tetrahydro-1H-imidazo[4,5-c]pyridine-5-carboxylate

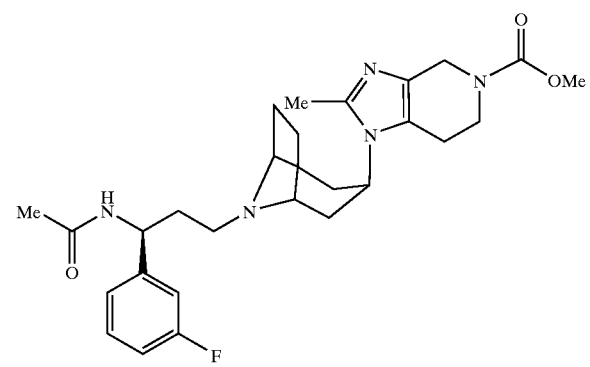

Acetyl chloride (0.062 g, 0.79 mmol) was added to a solution of methyl 1-endo-{8-[(3S)-3-amino-3-(3-fluorophenyl)propyl]-8-azabicyclo[3.2.1]oct-3-yl}-2-methyl-4,5,6,7-tetrahydro-1H-imidazo[4,5-c]pyridine-5-carboxylate trihydrochloride (Preparation 40) (0.409 g, 0.72 mmol) and triethylamine (0.33 g, 3.25 mmol) dissolved in dichloromethane (10 ml) under nitrogen at room temperature and the reaction mixture stirred for 2 hours. The solution was then washed with water (10 ml), 1 N sodium hydroxide solution (10 ml) and brine (10 ml). The organic phase was separated, dried (MgSO$_4$) and solvent removed under reduced pressure. The residue was purified by flash column chromatography on silica gel eluting with a solvent gradient of dichloromethane:methanol:concentrated aqueous ammonia (99:1:0.1, by volume, changing to 97:3:0.3). Product containing fractions were evaporated to afford the title compound as a white foam (0.24 g).

$^1$H NMR (400 MHz, CDCl$_3$): δ: 7.30–7.25 (1H, m), 7.10–6.90 (3H, m), 6.80–6.50 (1H, m), 5.20–5.10 (1H, q), 4.65–4.38 (3H, m), 3.80–3.60 (5H, m), 3.50–3.30 (2H, m), 2.80–1.90 (16H, m), 1.70–1.40 (4H, m) ppm.

LRMS (electrospray): m/z [M+H]$^+$ 498.

Examples 34–43 were prepared by analogous methods to those described above. LRMS was by electro-spray.

| Example No. and structure | ¹H NMR (400 MHz, CDCl₃) | LRMS m/z |
|---|---|---|
| Example 34 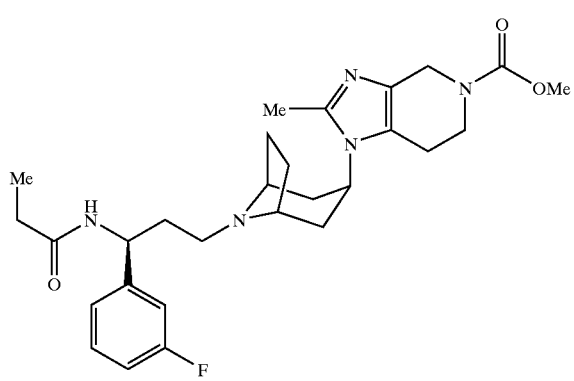 | 7.30–7.25 (1H, m), 7.10–6.90 (3H, m), 6.60–6.40 (1H, m), 5.20–5.10 (1H, q), 4.65–4.38 (3H, m), 3.80–3.60 (5H, m), 3.50–3.30 (2H, m), 2.80–1.90 (15H, m), 1.70–1.50 (4H, m), 1.2 (3H, t) | 512 [M + H]⁺ |
| Example 35 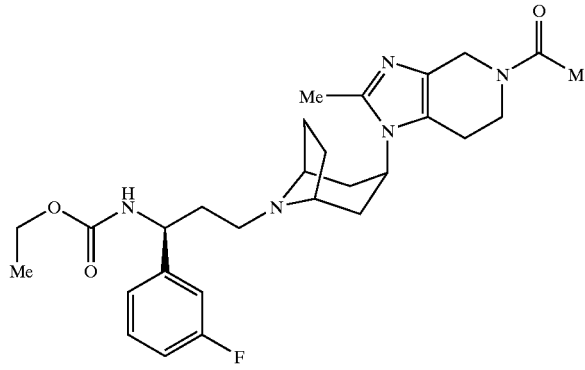 | 7.40–7.25 (1H, m), 7.10–6.90 (4H, m), 5.00–4.80 (1H, m), 4.65–4.40 (3H, m), 4.20–3.65 (4H, m), 3.55–3.30 (2H, m), 2.85–1.50 (20H, m), 1.40–1.00 (3H, m) | 512 [M + H]⁺ |
| Example 36 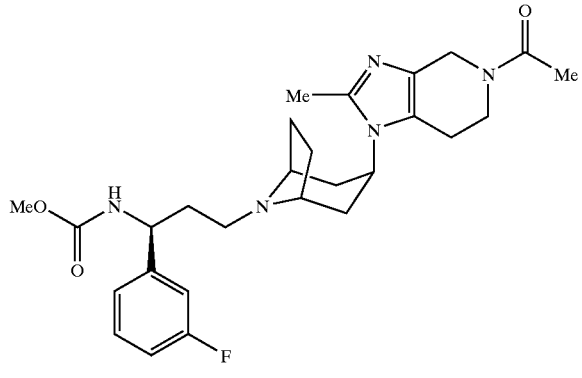 | 7.35–7.25 (1H, m), 7.10–6.90 (3H, m), 5.00–4.80 (1H, m), 4.65–4.40 (3H, m), 3.95–3.85 (2H, t), 3.75–3.62 (5H, m), 3.55–3.30 (2H, m), 2.85–1.55 (20H, m) | 498 [M + H]⁺ |
| Example 37  | 7.40–7.30 (1H, m), | 513 |

-continued
| Example No. and structure | $^1$H NMR (400 MHz, CDCl$_3$) | LRMS m/z |
|---|---|---|
| 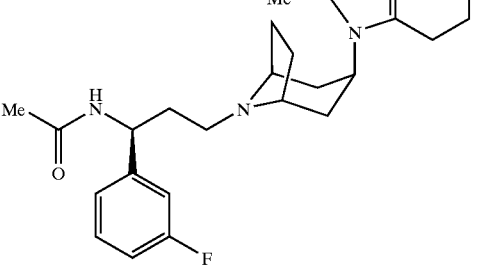 Example 38 | 7.10–6.90 (3H, m), 6.65–6.45 (1H, m), 4.65–4.40 (3H, m), 4.17 (2H, q), 3.80–3.70 (2H, m), 3.45–3.35 (2H, m), 2.80–1.90 (16H, m), 1.70–1.55 (4H, m), 1.25 (3H, t) | [M + H]$^+$ 512 |
| 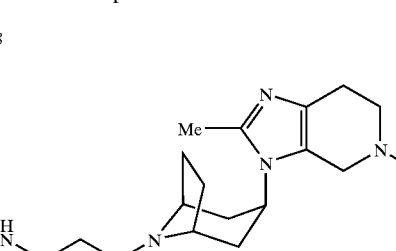 Example 39 | 7.40–7.30 (1H, m), 7.05 (1H, d), 7.05–6.90 (2H, m), 6.70–6.50 (1H, m), 5.20–5.05 (1H, m), 4.95 (1H, m), 4.65–4.30 (3H, m), 3.80–3.60 (2H, m), 3.45–3.25 (2H, m), 2.75–2.60 (2H, m), 2.60–2.35 (5H, m), 2.35–2.20 (2H, m), 2.20–2.00 (5H, m), 2.00–1.85 (2H, m), 1.75–1.45 (4H, m), 1.25 (6H, d) | [M + H]$^+$ 526 |
| 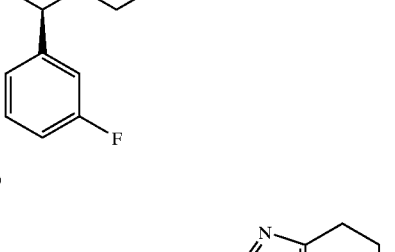 Example 40 | 7.40–7.30 (1H, m), 7.05 (1H, d), 7.05–6.90 (2H, m), 6.75–6.50 (1H, m), 5.20–5.05 (1H, m), 4.65–4.40 (3H, m), 4.20 (2H, q), 3.80–3.60 (2H, m), 3.50–3.30 (2H, m), 2.75–2.60 (2H, m), 2.60–2.45 (2H, m), 2.40 (3H, s), 2.35–2.20 (2H, m), 2.20–1.85 (7H, m), 1.75–1.45 (4H, m), 1.25 (3H, t) | [M + H]$^+$ 526 |
| 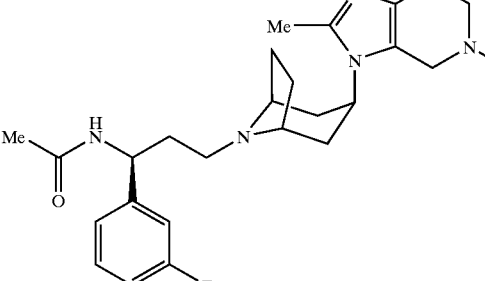 Example 41 | 7.40–7.30 (1H, m), 7.05 (1H, d), 7.05–6.90 (2H, m), 6.65–6.40 (1H, br s), 5.15–5.05 (1H, m), 4.65–4.35 (3H, m), 4.16 (2H, q), 3.80–3.60 (2H, m), 3.50–3.30 (2H, m), 2.75–1.80 (15H, m), 1.80–1.40 (4H, m), 1.25 (3H, t), 1.15 (3H, t) | [M + H]$^+$ 512 |

-continued
| Example No. and structure | ¹H NMR (400 MHz, CDCl₃) | LRMS m/z |
|---|---|---|
| 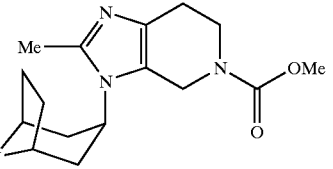 | 7.05 (1H, d), 7.00–6.90 (2H, m), 6.60–6.40 (1H, br s), 5.15–5.05 (1H, m), 4.65–4.40 (3H, m), 3.80–3.60 (5H, m), 3.50–3.30 (2H, m), 2.75–2.60 (2H, m), 2.60–2.40 (2H, m), 2.40–2.20 (4H, m), 2.20–2.05 (2H, m), 2.05–1.90 (2H, m), 1.80–1.50 (4H, m), 1.20 (3H, t) | [M + H]⁺ |
| Example 42 | 7.35–7.30 (1H, m), | 526 |
| 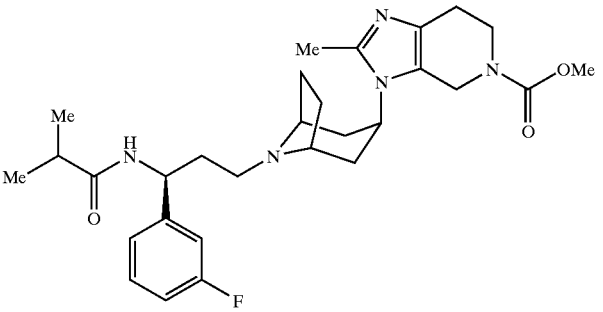 | 7.05 (1H, d), 7.00–6.90 (2H, m), 6.55–6.35 (1H, br s), 5.15–5.05 (1H, m), 4.60–4.35 (3H, m), 3.80–3.60 (5H, m), 3.45–3.30 (2H, m), 2.75–2.60 (2H, m), 2.60–2.20 (8H, m), 2.20–2.05 (2H, m), 2.05–1.85 (2H, m), 1.75–1.45 (4H, m), 1.25–1.10 (6H, m) | [M + H]⁺ |
| Example 43 | 7.35–7.30 (1H, m), | 524 |
| 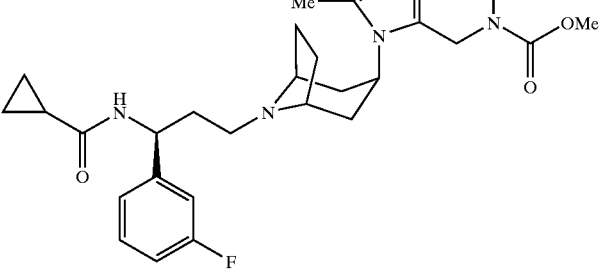 | 7.05 (1H, d), 7.05–6.90 (2H, m), 6.90–6.60 (1H, br s), 5.20–5.10 (1H, m), 4.60–4.35 (3H, m), 3.80–3.60 (5H, m), 3.50–3.30 (2H, m), 2.75–2.60 (2H, m), 2.60–2.20 (7H, m), 2.20–1.90 (4H, m), 1.75–1.50 (4H, m), 1.45–1.30 (1H, m), 1.05–0.90 (2H, m), 0.85–0.70 (2H, m) | [M + H]⁺ |

Example 44

Methyl 1-endo-{8-[(3S)-3-(acetamido)-3-(3-fluorophenyl)propyl]-8-azabicyclo[3.2.1]oct-3-yl}-2-methyl-4,5,6,7-tetrahydro-1H-imidazo[4,5-c]pyridine-5-carboxylate monohydrate

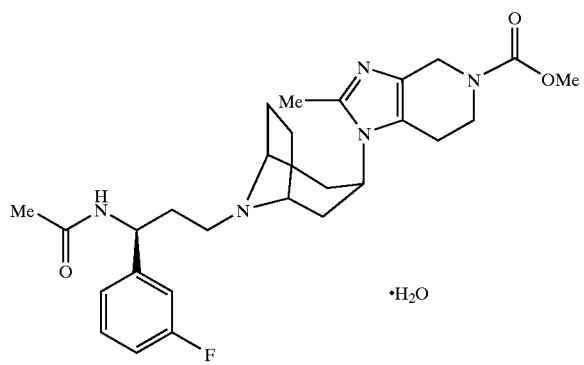

Sodium triacetoxyborohydride (11.0 g, 51.9 mmol) was added portionwise to a solution of N-[(1S)-1-(3-fluorophenyl)-3-oxopropyl]acetamide (Preparation 43) (11.32 g, 54.1 mmol) and methyl 1-(8-azabicyclo[3.2.1]oct-3-yl)-2-methyl-4,5,6,7-tetrahydro-1H-imidazo[4,5-c]pyridine-5-carboxylate (Preparation 48) (13.73 g, 45.1 mmol) in dichloromethane (150 ml) and the mixture stirred for one hour at room temperature. The solution was then washed with water (100 ml), brine (50 ml) and dried (MgSO4). Solvent was evaporated under reduced pressure and the resulting white solid dissolved in ethyl acetate (100 ml). Slight cooling induced crystallisation which was allowed to complete at room temperature overnight. The resulting white solid was filtered off and recrystalised from acetone (4 ml/g) to give the title compound as a white crystalline solid (15 g).

Found C, 62.80; H, 7.48; N, 13.55%; C27H37FN5O3.H2O requires C, 62.89; H, 7.43; N, 13.58%

1H NMR (400 MHz, CDCl3): δ: 7.30–7.25 (1H, m), 7.10–6.90 (3H, m), 6.80–6.50 (1H, m), 5.20–5.10 (1H, q), 4.65–4.38 (3H, m), 3.80–3.60 (5H, m), 3.50–3.30 (2H, m), 2.80–1.90 (16H, m), 1.70–1.40 (4H, m) ppm.

LRMS (electrospray): m/z [M+H]+ 498.

The compound of Example 44 exhibits a weight loss of 3.58% between 33° C. and 172° C. under Thermogravimetric Analysis (TGA). Evolved Gas Analysis (EGA) revealed this weight loss to be attributed to the evolution of water. This water is retained upon drying at 30° C./0% RH using Dynamic Vapour Sorption (DVS). Thus, the compound of Example 44 exists as a monohydrate (1.03 moles H2O). TGA was determined using a TA Instruments Q50 from ambient to 300° C. at a heating rate of 20° C./min with helium purge gas. EGA was carried out by mass spectroscopy using a Pfeiffer Thermostar GSD 300T with helium carrier gas. DVS was carried out using a SMS Ltd DVS-1.

Example 45

Methyl 1-{endo-8-[(3S)-3-acetamido-3-(3-fluorophenyl)propyl]-8-azabicyclo[3.2.1]oct-3-yl}-2-methyl-4,5,6,7-tetrahydro-1H-imidazo[4,5-c]pyridine-5-carboxylate monohydrate

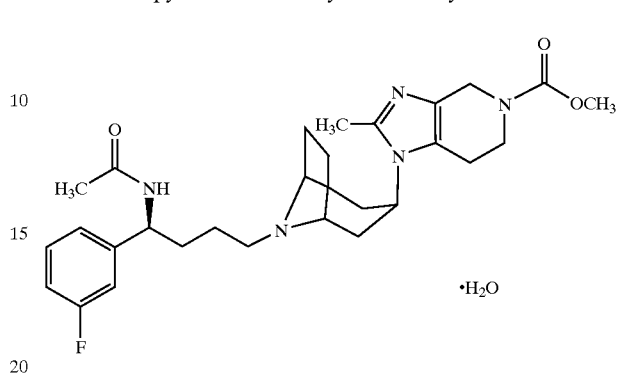

The title compound from Preparation 54 (184.8 g, 0.406 mol) was slurried in ethyl acetate (930 ml), saturated sodium carbonate solution (930 ml) and water (930 ml). To the resultant two-phase solution was added acetyl chloride (35 ml, 0.490 mol) over 30 minutes, resulting in a 9° C. exotherm. A sample was taken and analysis by HPLC showed that the reaction was complete. Dichloromethane (1.5 L) was added and the two-phase solution separated. The organic layer was washed with water (560 ml). The organic layer was evaporated under reduced pressure to a volume of 370 ml ethyl acetate. To the resultant solution was added ethyl acetate saturated with water (530 ml). The mixture was stirred at ambient temperature for 30 minutes. A white solid formed and was collected by filtration and dried in an oven under reduced pressure at 50° C. overnight, to give the title compound as a monohydrate, 142.7 g, 59%.

LRMS (Electrospray): m/z=498.5 (MH+)

Example 46

Methyl 1-{endo-8-[(3S)-3-acetamido-3-(3-fluorophenyl)propyl]-8-azabicyclo[3.2.1]oct-3-yl}-2-methyl-4,5,6,7-tetrahydro-1H-imidazo[4,5-c]pyridine-5-carboxylate (R,R)-tartrate

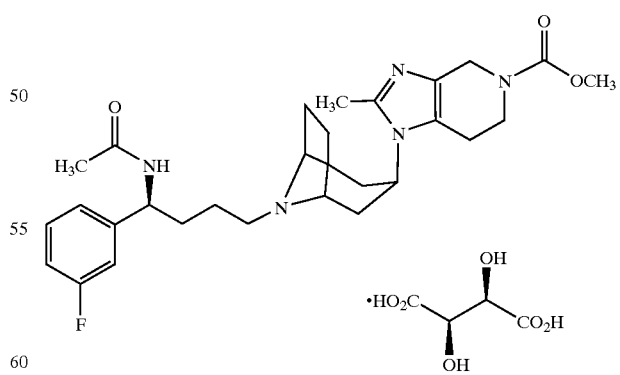

L-Tartaric acid (46.4 g, 0.31 mol) was slurried in propan-2-ol (700 ml). To the resultant solution was added the title compound of Example 45 (140 g, 0.28 mol) as a slurry in propan-2-ol (700 ml) over 1.5 hours. The mixture was heated to reflux for 30 minutes. The reaction was cooled to ambient temperature, then to 5° C. over 1 hour. The slurry was stirred at 5° C. for 1.5 hours. The solid was collected by filtration and dried in an oven under reduced pressure at 50° C. overnight to yield the title compound as a white solid, 177.9 g, 98%.

LRMS (Electrospray): m/z=498.5 (MH⁺)

Examples 47–49

Examples 47–49, respectively the (D)-tartrate, succinate and fumarate salts of methyl 1-{endo-8-[(3S)-3-acetamido-3-(3-fluorophenyl)propyl]-8-azabicyclo[3.2.1]oct-3-yl}-2-methyl-4,5,6,7-tetrahydro-1H-imidazo[4,5-c]pyridine-5-carboxylate, were prepared in the manner described for Example 46, employing the corresponding acid.

Preparation 1

8-Benzyl-8-azabicyclo[3.2.1]octan-3-one

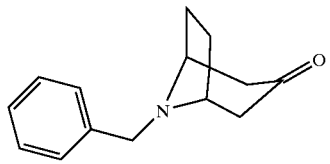

A solution of 2,5-dimethoxytetrahydrofuran (50 g, 378 mmol) in hydrochloric acid (0.025 N, 160 ml) was cooled to 0° C. for 16 hours. Benzylamine hydrochloride (65 g, 453 mmol), ketomalonic acid (55 g, 377 mmol) and an aqueous solution of sodium acetate (300 ml, 0.69 M) were added and the reaction stirred at room temperature for one hour. The mixture was heated to 50° C. for further 90 minutes, then cooled in an ice bath and basified to pH12 with 2N sodium hydroxide solution. The layers were separated and the aqueous phase extracted with ethyl acetate (3×300 ml). The combined organic extracts were washed with water, dried (MgSO₄), filtered and evaporated under reduced pressure. The residual brown oil was distilled under reduced pressure (126°/3 mmHg) to afford the title compound as an off-white solid (37.81 g).

¹H NMR (400 MHz, CDCl₃): δ: 1.64 (2H, m), 2.06–2.14 (2H, m), 2.18 (1H, s), 2.23 (1H, s), 2.68 (1H, m), 2.72 (1H, m), 3.48 (2H, s), 3.73 (2H, s), 7.20–7.29 (1H, m), 7.32 (2H, m), 7.42 (2H, d) ppm.

LRMS: m/z 216.3 (MH⁺).

Preparation 2 tert-Butyl 3-oxo-8-azabicyclo[3.2.1]octan-8-carboxylate

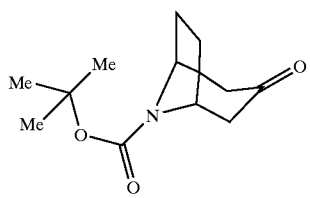

A mixture of 8-benzyl-8-azabicyclo[3.2.1]octan-3-one (Preparation 1) (15.0 g, 69.7 mmol), di-tert-butyl dicarbonate (18.2 g, 83.4 mmol) and 20% w/w palladium hydroxide on carbon (3.0 g) in ethyl acetate (165 ml) was stirred for 4 hours at room temperature under an atmosphere of hydrogen at 269 kPa. The mixture was filtered through Arbocel® and the solvent removed under reduced pressure. The residue was purified by column chromatography on silica gel using an elution gradient of hexane:ether (100:0 to 50:50) to afford the title compound as a colourless oil which crystallized on standing (16.2 g).

¹H NMR (400 MHz, CDCl₃): δ:1.48 (9H, s), 1.60–1.68 (2H, m), 2.00–2.11 (2H, m), 2.26–2.34 (2H, m), 2.48–2.82 (2H, m), 4.35–4.58 (2H, m) ppm.

Preparation 3 tert-Butyl 3-(benzylamino)-endo-8-azabicyclo[3.2.1]octane-8-carboxylate

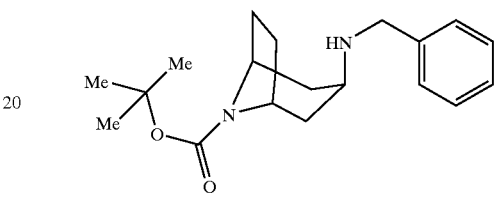

A solution of tert-butyl 3-oxo-8-azabicyclo[3.2.1]octan-8-carboxylate (Preparation 2) (10.0 g, 44.4 mmol), benzylamine (4.85 ml, 49.7 mmol) and sodium triacetoxyborohydride (14.11 g, 66.6 mmol) was stirred for 16 hours at room temperature in a mixture of glacial acetic acid:dichloromethane (1:9 v/v, 290 ml). The solvents were evaporated under reduced pressure and the residue dissolved in ethyl acetate (200 ml), then washed with saturated aqueous sodium carbonate solution (50 ml) and water (50 ml). The organic solution was dried (MgSO₄), filtered and evaporated under reduced pressure. The residue was purified by column chromatography on silica gel using an eluent of dichloromethane:methanol:concentrated aqueous ammonia (98:2:0.25) to afford the title compound as a white solid (7.00 g).

¹H NMR (400 MHz, CDCl₃): δ: 1.42–1.48 (11H, m), 1.52–1.61 (2H, m), 1.85–2.19 (5H, m), 2.95–3.03 (1H, m), 3.74 (2H, s), 4.03–4.23 (2H, m), 7.20–7.26 (1H, m), 7.26–7.32 (4H, m) ppm.

Preparation 4 tert-Butyl 3-endo-amino-8-azabicyclo[3.2.1]octane-8-carboxylate

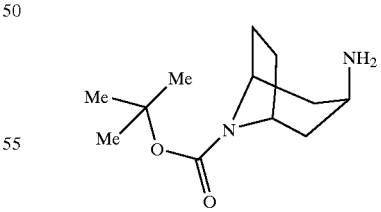

A mixture of tert-butyl 3-(benzylamino)-endo-8-azabicyclo[3.2.1]octane-8-carboxylate (Preparation 3) (7.00 g, 22.1 mmol), ammonium formate (7.00 g, 111 mmol) and 20% w/w palladium hydroxide on carbon (0.70 g) in ethanol (200 ml) was heated to 50° C., until gas evolution ceased. The cooled mixture was filtered through Arbocel® and the filtrate evaporated under reduced pressure. The residue was purified by column chromatography on silica gel using an elution gradient of dichloromethane:methanol:concentrated aqueous ammonia (98:2:0.25 to 95:5:0.5) to afford the title compound as a colourless oil (4.70 g).

LRMS: m/z 227.2 (MH$^+$).

Preparation 5

3-Fluoropyridine-N-oxide

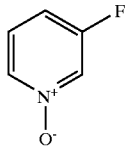

3-Fluoropyridine (20 g, 0.20 mol) was dissolved in glacial acetic acid (120 ml) and slowly heated to 85° C. under a nitrogen atmosphere. Concentrated sulfuric acid (1 ml) was then added, followed by portion-wise addition of 30 wt. % hydrogen peroxide (52 ml, 0.41 mol). The mixture was refluxed for 1 day. The solvent was evaporated under reduced pressure and the residue taken up in dichloromethane (400 ml). Potassium hydrogen carbonate (30 g) was added to the solution and the mixture was stirred for one hour. The solution was filtered and evaporated under reduced pressure to afford the title compound as a yellow oil which solidified on standing (26 g).

$^1$H-NMR (400 MHz, CDCl$_3$): δ: 7.05 (1H, m), 7.22 (1H, m), 8.10 (1H, m), 8.20 (1H, m) ppm.

Preparation 6

3-Fluoro-4-nitropyridine N-oxide

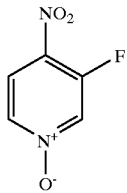

Concentrated H$_2$SO$_4$ (75 ml) was carefully added to 3-fluoropyridine N-oxide (Preparation 5) (50 g, 0.44 mol), cooled at room temperature by using a water bath. Fuming nitric acid (55 ml) was dissolved in concentrated sulfuric acid (75 ml) and the colourless solution was added dropwise to the substrate over 15 minutes at room temperature. The yellow mixture was heated for 1.5 hours at 90° C. The mixture was allowed to reach room temperature and slowly poured onto ice (900 g). The aqueous layer was extracted with dichloromethane (3×500 ml) and the solvent evaporated under reduced pressure to yield a yellow solid. This was washed with pentane (200 ml). The residue was dissolved in dichloromethane (50 ml). A yellow precipitate formed which was filtered off to yield the title compound (10 g).

$^1$H-NMR (400 MHz, d$_6$-DMSO): δ: 8.20 (2H, m), 8.90 (1H, m) ppm.

Preparation 7 tert-Butyl 3-endo-[(4-nitro-1-oxido-3-pyridinyl) amino]-8-azabicyclo[3.2.1]octane-8-carboxylate

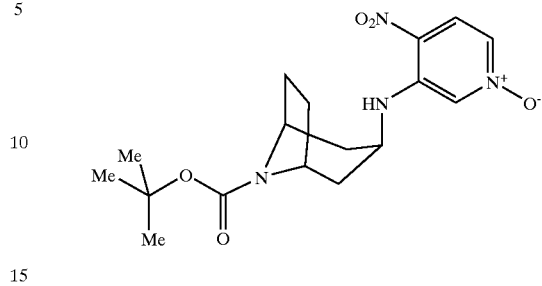

tert-Butyl 3-amino-endo-8-azabicyclo[3.2.1]octane-8-carboxylate (Preparation 4) (19 g, 0.084 mol) and 3-fluoro-4-nitropyridine N-oxide (Preparation 6) (13 g, 0.084 mol) were dissolved in acetonitrile (750 ml). Anhydrous potassium carbonate (13.6 g, 0.098 mol) was then added in one portion and then the mixture was heated to reflux and stirred for 16 hours under a nitrogen atmosphere. The solvent was evaporated under reduced pressure and the residue taken up into ethyl acetate (750 ml), washed with water (100 ml), then brine (100 ml). The organic layer was dried (MgSO$_4$) and the solvent removed by evaporated under reduced pressure. This residue was washed with diethyl ether (100 ml) and filtered to afford the title compound as a yellow solid (16 g).

$^1$H-NMR (400 MHz, CDCl$_3$): δ: 1.42 (9H, s), 1.62 (3H, m), 1.8 (2H, d), 1.97 (2H, m), 2.10 (2H, m), 2.30 (2H, m), 3.80 (1H, m), 7.42 (1H, m), 7.80 (1H, m) 8.10 (1H, m), 8.60 (1H, m) ppm.

LRMS: m/z 387 (MH$^+$).

Preparation 8

3-endo-(8-Acetyl-8-azabicyclo[3.2.1]oct-3-yl)-2-methyl-3H-imidazo[4,5-c]pyridine

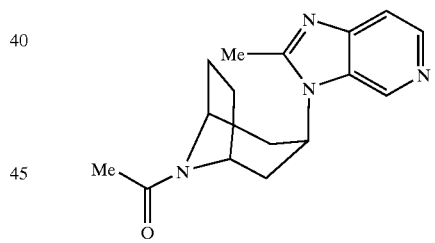

tert-Butyl 3-endo-[(4-nitro-1-oxido-3-pyridinyl)amino]-8-azabicyclo[3.2.1]-octane-8-carboxylate (Preparation 7) (15 g, 0.04 mol) was dissolved in glacial acetic acid (100 ml) at room temperature. Iron powder (8.0 g, 0.144 mol) was added and the mixture heated to 130° C. for 4 hours. Acetic anhydride (100 ml) was added and the mixture heated to 140° C. for 3 days. The solvent was removed under reduced pressure, and water (200 ml) was added. Sodium hydroxide pellets were added to the mixture until pH 10. The mixture was extracted with dichloromethane (1000 ml) and the organic extract dried (Na$_2$SO$_4$). The solvent was evaporated under reduced pressure to afford the title compound as a pale-yellow solid (7.4 g).

$^1$H-NMR (400 MHz, CDCl$_3$): δ: 1.90–2.10 (3H, m), 2.18 (3H, s), 2.20–2.30 (3H, m), 2.50–2.70 (5H, m), 4.22 (1H, m), 4.40 (1H, m), 4.90 (1H, m), 7.60 (1H, d), 8.40 (1H, d), 8.82 (1H, s) ppm.

LRMS: m/z 285 (MH$^+$).

Preparation 9

3-endo-(8-Acetyl-8-azabicyclo[3.2.1]oct-3-yl)-2-methyl-4,5,6,7-tetrahydro-3H-imidazo[4,5-c]pyridine

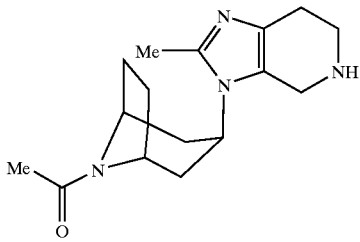

3-endo-(8-Acetyl-8-azabicyclo[3.2.1]oct-3-yl)-2-methyl-3H-imidazo[4,5-c]pyridine (Preparation 8) (2.69 g, 9.5 mmol) was dissolved in glacial acetic acid (50 ml) and hydrogenated at 400 kPa and 60° C. for 18 hours. The cool reaction mixture was filtered through a pad of Arbocel® and the filtrate evaporated under reduced pressure. The residue was dissolved in water (70 ml) and solvent evaporated under reduced pressure. The residue was again dissolved in water (70 ml) and the solution adjusted to pH10 by the addition of 2N aqueous sodium hydroxide solution. The aqueous solution was extracted with dichloromethane (4×100 ml), the combined organic extracts dried (Na$_2$SO$_4$) and solvent evaporated under reduced pressure. The residue was purified by flash column chromatography on silica gel eluting with a solvent gradient of dichloromethane:methanol:concentrated aqueous ammonia (90:10:1, by volume, changing to 85:15:1). Product containing fractions were evaporated to afford the title compound as a white foam (2.6 g).

$^1$H NMR (400 MHz, CDCl$_3$): δ: 4.85–4.80 (1H, m), 4.25–4.20 (1H, m), 3.95 (2H, s), 3.90–3.80 (1H, m), 3.10 (2H, m), 2.70–2.45 (5H, m), 2.35 (3H, s), 2.20–2.00 (5H, m), 1.80–1.60 (4H, m) ppm.

LRMS (electrospray): m/z [M+Na]$^+$ 311, [M+H]$^+$ 289.

Preparation 10

3-endo-(8-Acetyl-8-azabicyclo[3.2.1]oct-3-yl)-5-benzyl-2-methyl-4,5,6,7-tetrahydro-3H-imidazo[4,5-c]pyridine

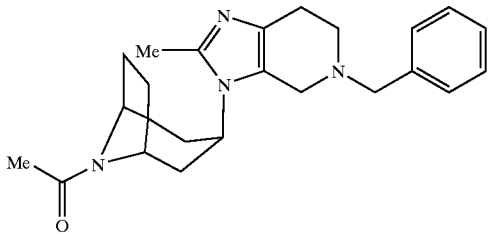

Acetic acid (0.9 ml, 15.6 mmol) was added to a stirred solution of 3-endo-(8-acetyl-8-azabicyclo[3.2.1]oct-3-yl)-2-methyl-4,5,6,7-tetrahydro-3H-imidazo[4,5-c]pyridine (Preparation 9) (2.6 g, 9 mmol) and benzaldehyde (1.2 ml, 11.8 mmol) dissolved in dichloromethane (50 ml) under nitrogen at room temperature. Sodium triacetoxyborohydride (3.1 g, 14.6 mmol) was then added and the reaction was held at room temperature for 18 hours. The reaction mixture was partitioned between saturated aqueous sodium hydrogencarbonate solution (50 ml) and dichloromethane (50 ml). The organic phase was removed and the aqueous phase was washed with dichloromethane (50 ml). The combined organic phases were dried (MgSO$_4$) and the solvent was evaporated under reduced pressure. The residue was purified by flash column chromatography on silica gel eluting with a solvent gradient of dichloromethane:methanol:concentrated aqueous ammonia (94:6:0.6, by volume, changing to 92:8:0.8). Product containing fractions were evaporated to afford the title compound as a white solid (1.6 g).

$^1$H NMR (400 MHz, CDCl$_3$): δ: 7.40–7.25 (5H, m), 4.75 (1H, m), 4.15 (1H, m), 3.85 (1H, m), 3.70 (2H, s), 3.45 (2H, s), 2.85 (2H, m), 2.65 (2H, m), 2.50–2.35 (2H, m), 2.30 (3H, s), 2.10 (3H, s), 2.05–1.90 (2H, m), 1.60–1.35 (4H, m) ppm.

LRMS (electrospray): m/z [M+Na]$^+$ 401, [M+H]$^+$ 379.

Preparation 11

3-endo-(8-Azabicyclo[3.2.1]oct-3-yl)-5-benzyl-2-methyl-4,5,6,7-tetrahydro-3H-imidazo[4,5-c]pyridine

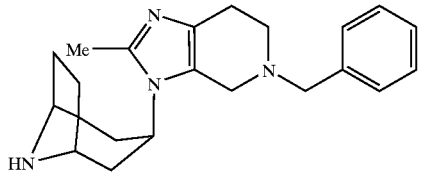

3-endo-(8-Acetyl-8-azabicyclo[3.2.1]oct-3-yl)-5-benzyl-2-methyl-4,5,6,7-tetrahydro-3H-imidazo[4,5-c]pyridine (Preparation 10) (2.6 g, 7 mmol) was dissolved in 6N aqueous hydrochloric acid (25 ml) and heated under reflux for 42 hours. The cooled reaction mixture was diluted with water (25 ml) and washed with diethyl ether (50 ml). The aqueous layer was adjusted to pH10 by the addition of 2N aqueous sodium hydroxide solution and extracted with dichloromethane (3×100 ml). The combined organic extracts were dried (Na$_2$SO$_4$) and solvent evaporated under reduced pressure to afford the title compound as a colourless gum, (2.05 g).

$^1$H-NMR (400 MHz, CDCl$_3$): δ 7.40–7.20 (5H, m), 4.25 (1H, m), 3.70 (2H, s), 3.60 (2H, m), 3.45 (2H, s), 2.85 (2H, m), 2.65 (2H, m), 2.40–2.30 (5H, m), 1.70 (2H, m), 1.40–1.30 (4H, m) ppm.

LRMS (electrospray): m/z [M+Na]$^+$ 359, [M+H]$^+$ 337.

Preparation 12 tert-Butyl (1S)-3-[3-endo-(5-benzyl-2-methyl-4,5,6,7-tetrahydro-3H-imidazo[4,5-c]pyridin-3-yl)-8-azabicyclo[3.2.1]oct-8-yl]-1-phenylpropylcarbamate

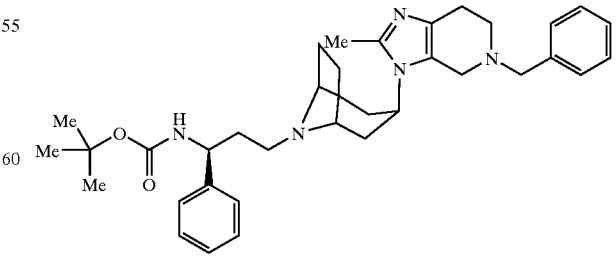

Acetic acid (0.6 ml, 10.4 mmol) was added to a stirred solution of 3-(8-azabicyclo[3.2.1]oct-3-yl)-5-benzyl-2- methyl-4,5,6,7-tetrahydro-3H-imidazo[4,5-c]pyridine (Preparation 11) (2.0 g, 6 mmol) and tert-butyl (1S)-3-oxo-1-phenylpropylcarbamate (WO0039125) (1.7 g, 6.8 mmol) dissolved in dichloromethane (40 ml) under nitrogen at room temperature. Sodium triacetoxyborohydride (2.0 g, 9.4 mmol) was then added and the reaction was held at room temperature for 18 hours. The reaction mixture was partitioned between saturated aqueous sodium hydrogencarbonate solution (50 ml) and dichloromethane (50 ml). The organic phase was removed and the aqueous phase was washed with dichloromethane (50 ml). The combined organic phases were dried (MgSO$_4$) and the solvent was evaporated under reduced pressure. The residue was purified by flash column chromatography on silica gel eluting with a solvent gradient of dichloromethane:methanol:concentrated aqueous ammonia (96:4:0.4, by volume, changing to 94:6:0.6). Product containing fractions were evaporated to afford the title compound as a white foam (2.53 g).

$^1$H NMR (400 MHz, CDCl$_3$): δ: 7.40–7.20 (10H, m), 5.90 (1H, br s), 4.80 (1H, br s), 4.40 (1H, m), 3.70 (2H, s), 3.50 (2H, s), 3.30 (1H, m), 3.20 (1H, m), 2.85 (2H, m), 2.65 (2H, m), 2.45–2.30 (5H, m), 2.20 (2H, m), 2.00–1.70 (4H, m), 1.45–1.20 (13H, m) ppm.

LRMS (electrospray): m/z [M+Na]$^+$ 592, [M+H]$^+$ 570.

Preparation 13

(1S)-3-[3-endo-(5-Benzyl-2-methyl-4,5,6,7-tetrahydro-3H-imidazo[4,5-c]pyridin-3-yl)-8-azabicyclo[3.2.1]oct-8-yl]-1-phenylpropylamine

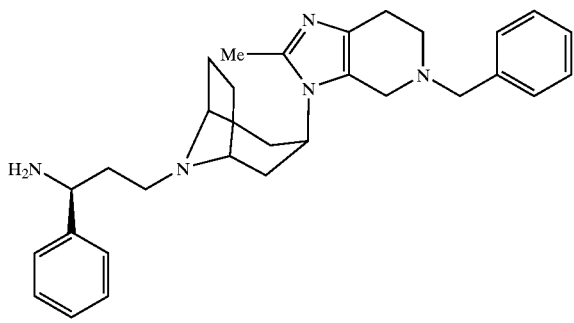

A solution of tert-butyl (1S)-3-[3-endo-(5-benzyl-2-methyl-4,5,6,7-tetrahydro-3H-imidazo[4,5-c]pyridin-3-yl)-8-azabicyclo[3.2.1]oct-8-yl]-1-phenylpropylcarbamate (Preparation 12) (2.4 g, 4.2 mmol) in 2.25 N HCl solution in methanol (20 ml) was stirred under nitrogen at room temperature for 18 hours. Solvent was evaporated under reduced pressure and the residue partitioned between ethyl acetate (100 ml) and 1N aqueous sodium hydroxide solution (50 ml). The organic layer was washed with water (50 ml), dried (Na$_2$SO$_4$) and solvent evaporated under reduced pressure to give the title compound as a colourless gum (1.8 g).

$^1$H NMR (400 MHz, CDCl$_3$): δ: 7.40–7.20 (10H, m), 4.30 (1H, m), 4.00 (1H, m), 3.70 (2H, s), 3.50 (2H, s), 3.35 (2H, m), 2.85 (2H, m), 2.65 (2H, m), 2.40–2.30 (5H, m), 2.20 (2H, m), 1.90 (2H, m), 1.80 (2H, m), 1.65 (2H, br s), 1.35–1.15 (4H, m) ppm.

LRMS (electrospray): m/z [M+H]$^+$ 470.

Preparation 14

(1S)-3-[3-endo-(2,5-Dimethyl-4,5,6,7-tetrahydro-3H-imidazo[4,5-c]pyridin-3-yl)-8-azabicyclo[3.2.1]oct-8-yl]-1-phenylpropylamine

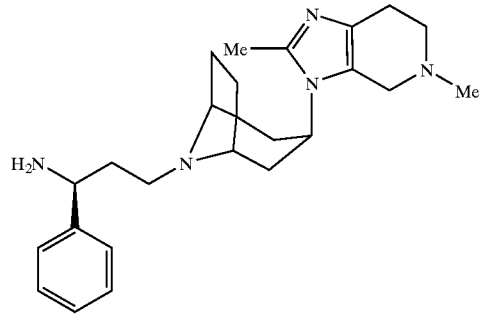

A solution of the title compound of Example 5 (0.26 g, 0.6 mmol) was dissolved in 6N aqueous hydrochloric acid (4 ml) and heated under reflux for 42 hours. The cooled reaction mixture was adjusted to pH10 by the addition of 2N aqueous sodium hydroxide solution and extracted with dichloromethane (3×30 ml). The combined organic phases were dried (MgSO$_4$) and the solvent was evaporated under reduced pressure. The residue was purified by flash column chromatography on silica gel eluting with a solvent gradient of dichloromethane:methanol:concentrated aqueous ammonia (90:10:0.5, by volume, changing to 90:10:1). Product containing fractions were evaporated to afford the title compound as a colourless gum (0.18 g).

$^1$H-NMR (400 MHz, CDCl$_3$): δ 7.40–7.20 (5H, m), 4.25 (1H, m), 3.70 (2H, s), 3.60 (2H, m), 3.45 (2H, s), 2.85 (2H, m), 2.65 (2H, m), 2.40–2.30 (5H, m), 1.70 (2H, m), 1.40–1.30 (4H, m) ppm.

LRMS (electrospray): m/z [M+Na]$^+$ 359, [M+H]$^+$ 337.

Preparation 15 tert-Butyl (1S)-1-(3-fluorophenyl)-3-oxopropylcarbamate

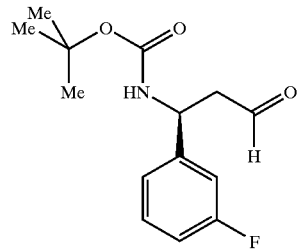

Diisobutylaluminium hydride (1 M in dichloromethane, 39 ml, 39 mmol) was cooled to −78° C. and added dropwise to a solution of methyl (3S)-3-[(tert-butoxycarbonyl)amino]-3-(3-fluorophenyl)propanoate (WO 0039125) (5.4 g, 18.2 mmol) in dichloromethane (100 ml) at −78° C. The reaction was stirred for 30 minutes at −78° C., then methanol (50 ml, pre-cooled to −78° C.) was added. The reaction was stirred for 30 minutes, then 2 N hydrochloric acid (250 ml)

added. The bi-phasic mixture was allowed to warm up to room temperature, the layers were separated, and the organic layer was dried (MgSO₄), filtered and evaporated under reduced pressure to afford the title compound as a clear, colourless oil, 4.8 g.

¹H-NMR (400 MHz, CDCl₃): δ: 1.40 (9H, bs), 2.92 (2H, m), 5.14 (2H, m), 6.90–7.02 (2H, m), 7.03 (1H, d), 7.30 (1H, m), 9.76 (1H, s) ppm.

LRMS: m/z 268.1 (MH⁺).

Preparation 16 tert-Butyl (1S)-3-[3-endo-(5-benzyl-2-methyl-4,5,6,7-tetrahydro-3H-imidazo[4,5-c]pyridin-3-yl)-8-azabicyclo[3.2.1]oct-8-yl]-1-(3-fluorophenyl)propylcarbamate

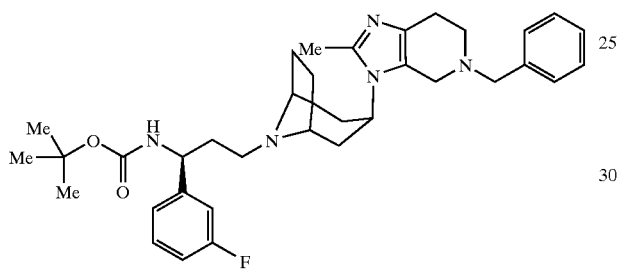

Acetic acid (0.3 ml, 5.2 mmol) was added to a stirred solution of 3-(8-azabicyclo[3.2.1]oct-3-yl)-5-benzyl-2-methyl-4,5,6,7-tetrahydro-3H-imidazo[4,5-c]pyridine (Preparation 11) (1.74 g, 5.2 mmol) and tert-butyl (1S)-1-(3-fluorophenyl)-3-oxopropylcarbamate (Preparation 15) (1.52 g, 5.7 mmol) dissolved in dichloromethane (25 ml) under nitrogen at room temperature. Sodium triacetoxyborohydride (1.31 g, 6.2 mmol) was then added and the reaction was held at room temperature for two hours. The reaction mixture was partitioned between saturated aqueous sodium hydrogencarbonate solution (50 ml) and dichloromethane (50 ml). The organic phase was removed and the aqueous phase was washed with dichloromethane (50 ml). The combined organic phases were dried (MgSO₄) and the solvent was evaporated under reduced pressure. The residue was purified by flash column chromatography on silica gel eluting with a solvent gradient of dichloromethane:methanol:concentrated aqueous ammonia (100:0:0.5, by volume, changing to 97:3:0.5). Product containing fractions were evaporated to afford the title compound as a white foam (1.8 g).

¹H NMR (400 MHz, CDCl₃): δ: 7.40–7.20 (6H, m), 7.05–6.85 (3H, m), 6.10–5.80 (1H, br s), 4.85–4.65 (1H, m), 4.40–4.25 (1H, m), 3.70 (2H, s), 3.45 (2H, s), 3.30–3.10 (2H, m), 2.90–2.80 (2H, m), 2.70–2.60 (2H, m), 2.50–2.30 (5H, m), 2.25–2.15 (2H, m), 2.10–1.65 (5H, m), 1.60–1.10 (12H, m) ppm.

LRMS (electrospray): m/z [M+H]⁺ 588.

Preparation 17 tert-Butyl (1S)-1-(3-fluorophenyl)-3-[3-endo-(2-methyl-4,5,6,7-tetrahydro-3H-imidazo[4,5-c]pyridin-3-yl)-8-azabicyclo[3.2.1]oct-8-yl]propylcarbamate

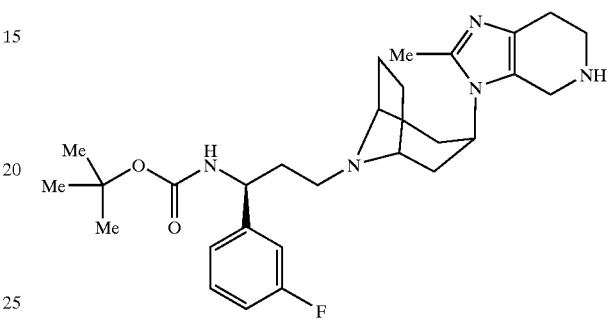

A mixture of tert-butyl (1S)-3-[3-endo-(5-benzyl-2-methyl-4,5,6,7-tetrahydro-3H-imidazo[4,5-c]pyridin-3-yl)-8-azabicyclo[3.2.1]oct-8-yl]-1-(3-fluorophenyl)propylcarbamate (Preparation 16) (2.00 g, 3.4 mmol), ammonium formate (1.07 g, 17 mmol) and 10% w/w palladium on carbon (0.15 g) in ethanol (30 ml) was heated to 60° C. After one hour additional ammonium formate (1.07 g, 17 mmol) was added and heating continued at 60 ° C. This process was repeated after a further hour. One hour after the second addition heating was removed and the cooled reaction mixture filtered through Arbocel® and the filtrate evaporated under reduced pressure. The residue was partitioned between dichloromethane (100 ml) and saturated aqueous sodium hydrogencarbonate solution (50 ml), the organic phase separated and washed with water (30 ml). The organic layer was dried (MgSO₄) and solvent evaporated under reduced pressure. The residue was purified by flash column chromatography on silica gel eluting with a solvent gradient of dichloromethane:methanol:concentrated aqueous ammonia (90:10:1). Product containing fractions were evaporated to afford the title compound as a white foam (1.45 g).

¹H NMR (400 MHz, CDCl₃): δ: 7.30–7.20 (1H, m), 7.10–6.85 (3H, m), 5.85–5.65 (1H, m), 4.90–4.65 (1H, m), 4.50–4.35 (1H, m), 3.95 (2H, s), 3.40–3.20 (2H, m), 3.10 (2H, t), 2.65–2.20 (10H, m), 2.15–1.65 (4H, m), 1.60–1.20 (13H, m) ppm.

LRMS (electrospray): m/z [M+H]⁺ 498.

Preparation 18 tert-Butyl (1S)-3-[3-endo-(5-acetyl-2-methyl-4,5,6,7-tetrahydro-3H-imidazo[4,5-c]pyridin-3-yl)-8-azabicyclo[3.2.1]oct-8-yl]-1-(3-fluorophenyl)propylcarbamate

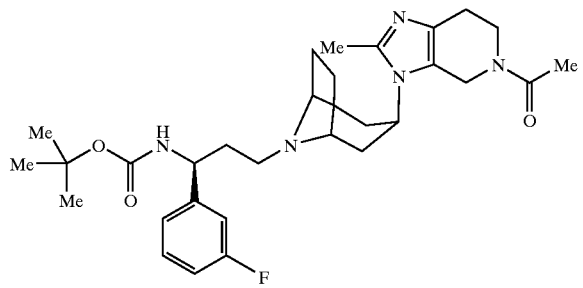

Acetyl chloride (0.13 g, 1.65 mmol) was added to a solution of tert-butyl (1S)-1-(3-fluorophenyl)-3-[3-endo-(2-methyl-4,5,6,7-tetrahydro-3H-imidazo[4,5-c]pyridin-3-yl)-8-azabicyclo[3.2.1]oct-8-yl]propylcarbamate (Preparation 17) (0.75 g, 1.5 mmol) in dichloromethane (5 ml) at 0° C. After 30 minutes the reaction mixture was diluted with dichloromethane (10 ml) and washed with saturated aqueous sodium hydrogencarbonate solution (10 ml). The organic layer was separated and the aqueous phase washed with dichloromethane (2×5 ml). The combined organic extracts were dried (MgSO₄) and solvent evaporated under reduced pressure to afford the title compound as a white foam (0.8 g).

$^1$H NMR (400 MHz, CDCl$_3$): δ: 7.30–7.20 (1H, m), 7.05–6.85 (3H, m), 5.90–5.70 (1H, m), 4.85–4.35 (4H, m), 3.65–3.60 (2H, t), 3.40–3.20 (2H, m), 2.70–1.00 (29H, m) ppm.

LRMS (electrospray): m/z [M+H]$^+$ 540.

Preparation 19

Methyl 3-endo-{8-[(3S)-3-[(tert-butoxycarbonyl)amino]-3-(3-fluorophenyl)propyl]-8-azabicyclo[3.2.1]oct-3-yl}-2-methyl-4,5,6,7-tetrahydro-3H-imidazo[4,5-c]pyridine-5-carboxylate

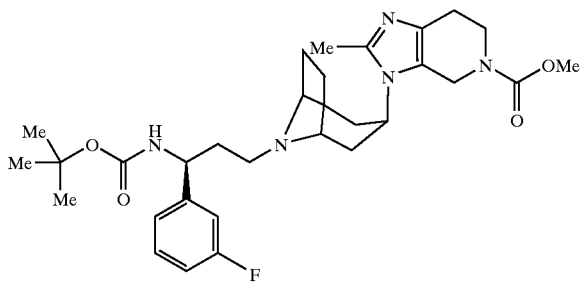

Methyl chloroformate (0.156 g, 1.65 mmol) was added to a solution of tert-butyl (1S)-1-(3-fluorophenyl)-3-[3-endo-(2-methyl-4,5,6,7-tetrahydro-3H-imidazo[4,5-c]pyridin-3-yl)-8-azabicyclo[3.2.1]oct-8-yl]propylcarbamate (Preparation 17) (0.75 g, 1.5 mmol) in dichloromethane (5 ml) at 0° C. After 30 minutes the reaction mixture was diluted with dichloromethane (10 ml) and washed with saturated aqueous sodium hydrogencarbonate solution (10 ml). The organic layer was separated and the aqueous phase washed with dichloromethane (2×5 ml). The combined organic extracts were dried (MgSO₄) and solvent evaporated under reduced pressure to afford the title compound as a white foam (0.77 g).

$^1$H NMR (400 MHz, CDCl$_3$): δ: 7.30–7.20 (1H, m), 7.05–6.85 (3H, m), 5.90–5.70 (1H, m), 4.90–4.70 (1H, m), 4.60–4.40 (3H, m), 3.75–3.60 (5H, m), 3.40–3.25 (2H, m), 2.65–2.38 (7H, m), 2.25–2.20 (2H, m), 2.15–1.20 (17H, m) ppm.

LRMS (electrospray): m/z [M+H]$^+$ 556.

Preparation 20

(1S)-3-[3-endo-(5-Acetyl-2-methyl-4,5,6,7-tetrahydro-3H-imidazo[4,5-c]pyridin-3-yl)-8-azabicyclo[3.2.1]oct-8-yl]-1-(3-fluorophenyl)propylamine

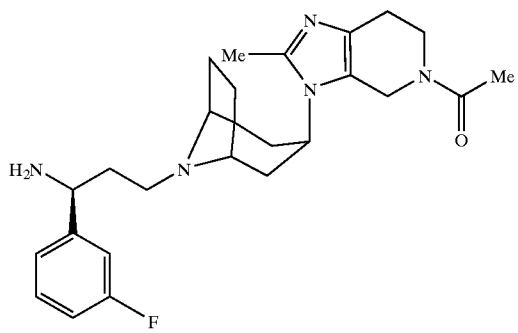

Hydrogen chloride gas was bubbled through a solution of tert-butyl (1S)-3-[3-endo-(5-acetyl-2-methyl-4,5,6,7-tetrahydro-3H-imidazo[4,5-c]pyridin-3-yl)-8-azabicyclo[3.2.1]oct-8-yl]-1-(3-fluorophenyl)propylcarbamate (Preparation 18) (0.77 g, 1.43 mmol) in dichloromethane (10 ml) and methanol (3 ml) at 0° C. until the solution was saturated. The reaction mixture was then allowed to warm to room temperature and after 20 minutes solvent was evaporated under reduced pressure. The residue was partitioned between dichloromethane (30 ml) and saturated aqueous sodium hydrogencarbonate solution (20 ml). The organic layer was separated and the aqueous phase extracted with dichloromethane (2×15 ml). The combined organic extracts were dried (MgSO₄) and solvent evaporated under reduced pressure to afford the title compound as a white foam (0.565 g).

$^1$H NMR (400 MHz, CDCl$_3$): δ: 7.30–7.20 (1H, m), 7.10–6.90 (3H, m), 4.60 (2H, s), 4.45–4.30 (1H, m), 4.05 (1H, t), 3.62 (2H, t), 3.40–3.25 (2H, m), 2.70–1.95 (14H, m), 1.85–1.40 (8H, m) ppm.

LRMS (electrospray): m/z [M+H]$^+$ 440.

Preparation 21

Methyl 3-endo-{8-[(3S)-3-amino-3-(3-fluorophenyl)propyl]-8-azabicyclo[3.2.1]oct-3-yl}-2-methyl-4,5,6,7-tetrahydro-3H-imidazo[4,5-c]pyridine-5-carboxylate

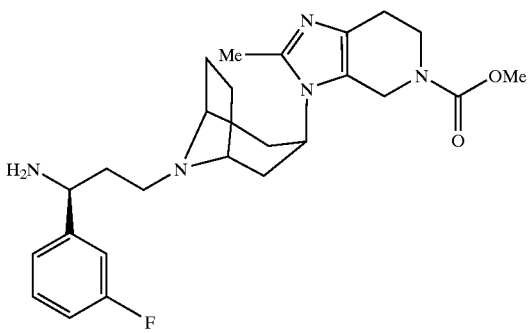

Hydrogen chloride gas was bubbled through a solution of methyl 3-endo-{8-[(3S)-3-[(tert-butoxycarbonyl)amino]-3-(3-fluorophenyl)propyl]-8-azabicyclo[3.2.1]oct-3-yl}-2-methyl-4,5,6,7-tetrahydro-3H-imidazo[4,5-c]pyridine-5-carboxylate (Preparation 19) (0.75 g, 1.35 mmol) in dichloromethane (10 ml) and methanol (3 ml) at 0° C. until the solution was saturated. The reaction mixture was then allowed to warm to room temperature and after 20 minutes solvent was evaporated under reduced pressure. The residue was partitioned between dichloromethane (30 ml) and saturated aqueous sodium hydrogencarbonate solution (20 ml). The organic layer was separated and the aqueous phase extracted with dichloromethane (2×15 ml). The combined organic extracts were dried (MgSO$_4$) and solvent evaporated under reduced pressure to afford the title compound as a white foam (0.566 g).

$^1$H NMR (400 MHz, CDCl$_3$): δ: 7.30–7.20 (1H, m), 7.10–7.00 (2H, m), 6.95–6.85 (1H, t), 4.60–4.30 (3H, m), 4.05 (1H, t), 3.75–3.60 (5H, m), 3.40–3.25 (2H, m), 2.65–2.55 (2H, m), 2.50–2.35 (5H, m), 2.30–2.15 (2H, m), 2.10–1.95 (2H, m), 1.85–1.35 (8H, m) ppm.

LRMS (electrospray): m/z [M+H]$^+$ 456.

Preparation 22 tert-Butyl (1S)-3-[3-endo-(2-methyl-4,5,6,7-tetrahydro-3H-imidazo[4,5-c]pyridin-3-yl)-8-azabicyclo[3.2.1]oct-8-yl]-1-phenylpropylcarbamate

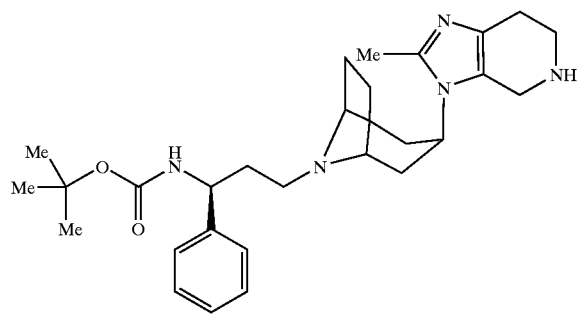

A mixture of tert-butyl (1S)-3-[3-endo-(5-benzyl-2-methyl-4,5,6,7-tetrahydro-3H-imidazo[4,5-c]pyridin-3-yl)-8-azabicyclo[3.2.1]oct-8-yl]-1-phenylpropylcarbamate (Preparation 12) (5.65 g, 9.93 mmol), ammonium formate (3.7 g, 58.7 mmol) and 20% w/w palladium hydroxide on carbon (0.50 g) in ethanol (100 ml) was heated to 85° C. After one hour additional ammonium formate (2.0 g, 17 mmol) was added and heating continued at 60° C. for a further hour. The cooled reaction mixture was then filtered through Arbocel® and the filtrate evaporated under reduced pressure. The residue was purified by flash column chromatography on silica gel eluting with a solvent gradient of dichloromethane:methanol:concentrated aqueous ammonia (94:6:0.6, by volume, changing to 92:8:0.8). Product containing fractions were evaporated to afford the title compound as a white foam (4.95 g).

$^1$H NMR (400 MHz, CDCl$_3$): δ: 7.35–7.20 (5H, m), 5.70 (1H, m), 4.80 (1H, m), 4.45 (1H, m), 3.90 (2H, s), 3.40–3.25 (2H, m), 3.10 (2H, t), 2.60 (2H, m), 2.55–2.40 (5H, m), 2.20 (2H, t), 2.10–1.75 (4H, m), 1.55–1.20 (14H, m) ppm.

LRMS (electrospray): m/z [M+H]$^+$ 480.

Preparation 23 tert-Butyl (1S)-3-{3-endo-[2-methyl-5-(3,3,3-trifluoropropanoyl)-4,5,6,7-tetrahydro-3H-imidazo[4,5-c]pyridin-3-yl]-8-azabicyclo[3.2.1]oct-8-yl}-1-phenylpropylcarbamate

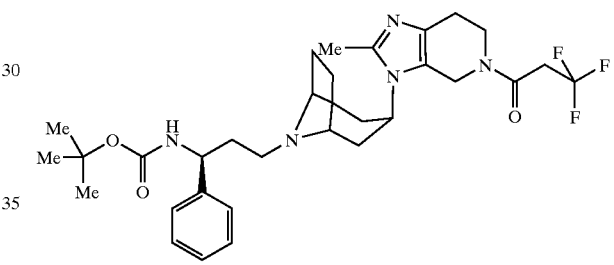

1-(3-Dimethylaminopropyl)-3-ethylcarbodiimide hydrochloride (0.54 g, 2.82 mmol) was added to a solution of 3,3,3-trifluoropropanoic acid (0.29 g, 2.26 mmol), tert-butyl (1S)-3-[3-endo-(2-methyl-4,5,6,7-tetrahydro-3H-imidazo[4,5-c]pyridin-3-yl)-8-azabicyclo[3.2.1]oct-8-yl]-1-phenylpropylcarbamate (Preparation 22) (0.96 g, 2.0 mmol), triethylamine (0.6 ml, 4.31 mmol) and 1-hydroxybenzotriazole (0.43 g, 2.81 mmol) dissolved in dichloromethane (50 ml) under nitrogen at room temperature. The reaction was stirred at room temperature for 18 hours, and then washed with saturated aqueous sodium hydrogencarbonate solution (30 ml). The organic phase was removed and the aqueous layer extracted with dichloromethane (2×30 ml). The combined dichloromethane extracts were dried (MgSO$_4$) and the solvent was removed under reduced pressure. The residue was purified by flash column chromatography on silica gel eluting with a solvent mixture of dichloromethane:methanol:concentrated aqueous ammonia (94:6:0.6, by volume). Product containing fractions were evaporated to afford the title compound as a white foam (1.09 g).

$^1$H NMR (400 MHz, CDCl$_3$): δ: 7.35–7.20 (5H, m), 5.65 (1H, m), 4.80 (1H, m), 4.70 (2H, s), 4.60–4.45 (2H, m), 3.70 (2H, m), 3.40–3.25 (4H, m), 2.70–2.60 (2H, m), 2.55–2.40 (5H, m), 2.25 (2H, m), 2.10–1.70 (4H, m), 1.55–1.20 (12H, m) ppm.

LRMS (electrospray): m/z [M+H]$^+$ 590.

Preparation 24

(1S)-3-{3-endo-[2-Methyl-5-(3,3,3-trifluoropropanoyl)-4,5,6,7-tetrahydro-3H-imidazo[4,5-c]pyridin-3-yl]-8-azabicyclo[3.2.1]oct-8-yl}-1-phenylpropylamine

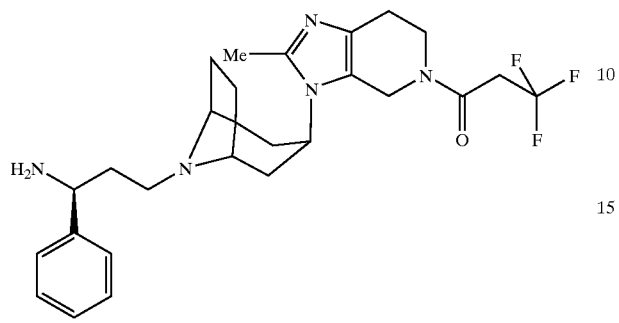

Hydrogen chloride gas was bubbled through a solution of tert-butyl (1S)-3-{3-endo-[2-methyl-5-(3,3,3-trifluoropropanoyl)-4,5,6,7-tetrahydro-3H-imidazo[4,5-c]pyridin-3-yl]-8-azabicyclo[3.2.1]oct-8-yl}-1-phenylpropylcarbamate (Preparation 23) (1.05 g, 1.78 mmol) in dichloromethane (20 ml) and methanol (3 ml) at 0° C. until the solution was saturated. The reaction mixture was then allowed to warm to room temperature and after one hour washed with 2N aqueous sodium hydroxide solution (2×20 ml). The organic layer was separated, dried (MgSO$_4$) and solvent evaporated under reduced pressure to afford the title compound as a white foam (0.80 g).

$^1$H NMR (400 MHz, CDCl$_3$): δ: 7.40–7.30 (5H, m), 4.70 (2H, m), 4.40 (1H, m), 4.05 (1H, t), 3.65 (2H, m), 3.40–3.25 (4H, m), 2.70–2.60 (2H, m), 2.50–2.30 (5H, m), 2.25 (2H, m), 2.05 (2H, m), 1.85–1.40 (8H, m) ppm.

LRMS (electrospray): m/z [M+H]$^+$ 490.

Preparation 25

Methyl 3-endo-(8-{(3S)-3-[(tert-butoxycarbonyl)amino]-3-phenylpropyl}-8-azabicyclo[3.2.1]oct-3-yl)-2-methyl-4,5,6,7-tetrahydro-3H-imidazo[4,5-c]pyridine-5-carboxylate

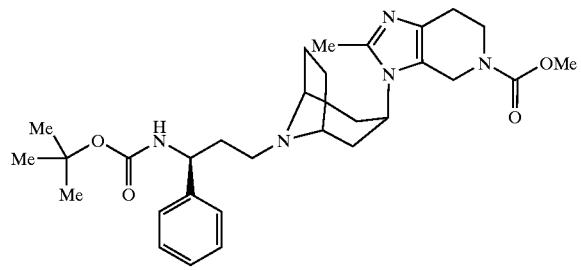

Methyl chloroformate (0.18 ml, 2.32 mmol) was added to a solution of tert-butyl (1S)-3-[3-endo-(2-methyl-4,5,6,7-tetrahydro-3H-imidazo[4,5-c]pyridin-3-yl)-8-azabicyclo[3.2.1]oct-8-yl]-1-phenylpropylcarbamate (Preparation 22) (0.96 g, 2.0 mmol) and triethylamine (0.36 ml, 2.59 mmol) in dichloromethane (20 ml) under nitrogen at room temperature. The reaction was stirred at room temperature for 1.5 hours and then washed with saturated aqueous sodium hydrogencarbonate solution (20 ml). The organic phase was removed and the aqueous layer extracted with more dichloromethane (2×20 ml). The combined dichloromethane extracts were dried (MgSO$_4$) and the solvent was removed under reduced pressure. The residue was purified by flash column chromatography on silica gel eluting with a solvent mixture of ethyl acetate:diethylamine (99:1, by volume, changing to 98:2 then 97:3). Product containing fractions were evaporated to afford the title compound as a white foam (0.96 g).

$^1$H NMR (400 MHz, CDCl$_3$): δ: 7.40–7.25 (5H, m), 5.65 (1H, m), 4.80 (1H, m), 4.60–4.40 (3H, m), 3.75–3.65 (5H, m), 3.40–3.25 (2H, m), 2.65 (2H, m), 2.55–2.40 (5H, m), 2.25 (2H, m), 2.15–2.05 (2H, m), 2.00–1.8 (2H, m), 1.65–1.30 (13H, m) ppm.

LRMS (electrospray): m/z [M+H]$^+$ 538.

Preparation 26

Methyl 3-endo-{8-[(3S)-3-amino-3-phenylpropyl]-8-azabicyclo[3.2.1]oct-3-yl}-2-methyl-4,5,6,7-tetrahydro-3H-imidazo[4,5-c]pyridine-5-carboxylate

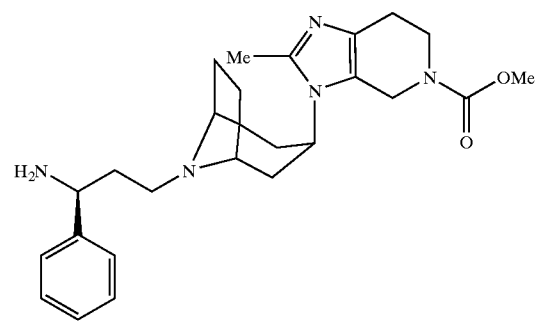

Hydrogen chloride gas was bubbled through a solution of methyl 3-endo-(8-{(3S)-3-[(tert-butoxycarbonyl)amino]-3-phenylpropyl}-8-azabicyclo[3.2.1]oct-3-yl)-2-methyl-4,5,6,7-tetrahydro-3H-imidazo[4,5-c]pyridine-5-carboxylate (Preparation 25) (0.95 g, 1.77 mmol) in dichloromethane (20 ml) and methanol (1 ml) at 0° C. until the solution was saturated. The reaction mixture was then allowed to warm to room temperature and after one hour washed with 2N aqueous sodium hydroxide solution (2×20 ml). The organic layer was separated, dried (MgSO$_4$) and solvent evaporated under reduced pressure to afford the title compound as a white foam (0.75 g).

$^1$H NMR (400 MHz, CDCl$_3$): δ: 7.40–7.30 (5H, m), 4.55 (2H, br s), 4.40 (1H, m), 4.05 (1H, t), 3.75–3.65 (5H, m), 3.35 (2H, m), 2.60 (2H, m), 2.45 (2H, m), 2.35 (3H, s), 2.25 (2H, m), 2.10 (2H, m), 1.80 (2H, m), 1.65–1.40 (6H, m) ppm.

LRMS (electrospray): m/z [M+H]$^+$ 439.

Preparation 27 tert-Butyl (1S)-3-[3-endo-(5-acetyl-2-methyl-4,5,6,7-tetrahydro-3H-imidazo[4,5-c]pyridin-3-yl)-8-azabicyclo[3.2.1]oct-8-yl]-1-phenylpropylcarbamate

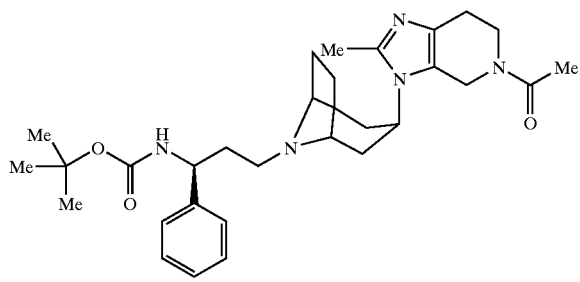

Acetyl chloride (0.09 ml, 1.26 mmol) was added to a solution of tert-butyl (1S)-3-[3-endo-(2-methyl-4,5,6,7-tetrahydro-3H-imidazo[4,5-c]pyridin-3-yl)-8-azabicyclo[3.2.1]oct-8-yl]-1-phenylpropylcarbamate (Preparation 22) (0.5 g, 1.09 mmol) and triethylamine (0.19 ml, 1.36 mmol) in dichloromethane (5 ml) under nitrogen at room temperature. The reaction was stirred at room temperature for 18 hours and then solvent was evaporated under reduced pressure. The residue was purified by flash column chromatography on silica gel eluting with a solvent gradient of dichloromethane:methanol:concentrated aqueous ammonia (94:6:0.6, by volume, changing to 92:8:0.8 then 90:10:0.6). Product containing fractions were evaporated to afford the title compound as a white foam (0.51 g).

$^1$H NMR (400 MHz, CDCl$_3$): δ: 7.40–7.20 (5H, m), 5.65 (1H, m), 4.80 (1H, m), 4.65 (2H, s), 4.55–4.40 (2H, m), 3.85 (1H, m), 3.65 (2H, m), 3.40–3.25 (2H, m), 2.70 (2H, m), 2.55–2.40 (5H, m), 2.25 (2H, m), 2.15 (3H, s), 2.10–2.00 (2H, m), 1.95–1.75 (2H, m), 1.65–1.30 (13H, m) ppm.

LRMS (electrospray): m/z [M+H]$^+$ 522.

Preparation 28

(1S)-3-[3-endo-(5-Acetyl-2-methyl-4,5,6,7-tetrahydro-3H-imidazo[4,5-c]pyridin-3-yl)-8-azabicyclo[3.2.1]oct-8-yl]-1-phenylpropylamine

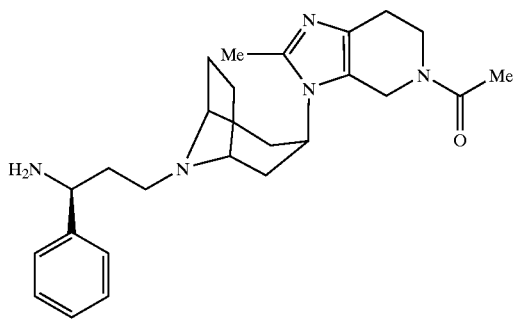

Hydrogen chloride gas was bubbled through a solution of tert-butyl (1S)-3-[3-endo-(5-acetyl-2-methyl-4,5,6,7-tetrahydro-3H-imidazo[4,5-c]pyridin-3-yl)-8-azabicyclo[3.2.1]oct-8-yl]-1-phenylpropylcarbamate (Preparation 27) (0.50 g, 0.96 mmol) in dichloromethane (5 ml) and methanol (0.5 ml) at 0° C. until the solution was saturated. The reaction mixture was then allowed to warm to room temperature and after one hour washed with 2N aqueous sodium hydroxide solution (2×5 ml). The organic layer was separated, dried (MgSO$_4$) and solvent evaporated under reduced pressure to afford the title compound as a white foam (0.265 g).

$^1$H NMR (400 MHz, CDCl$_3$): δ: 7.35–7.20 (5H, m), 4.60 (2H, br s), 4.45–4.30 (1H, m), 4.00 (1H, t), 3.60 (2H, m), 3.40–3.30 (2H, m), 2.50–2.30 (2H, m), 2.30–2.15 (2H, m), 2.13 (3H, s), 2.10–2.00 (2H, m), 1.80 (2H, m), 1.70–1.40 (6H, m) ppm.

LRMS (electrospray): m/z [M+H]$^+$ 422.

Preparation 29 tert-Butyl 3-endo-[(3-nitro-4-pyridinyl)amino]-8-azabicyclo[3.2.1]octane-8-carboxylate

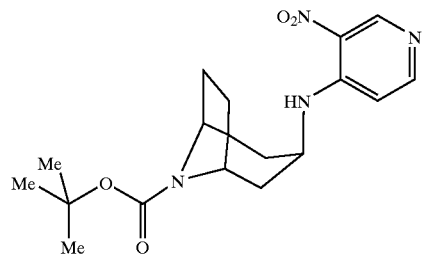

tert-Butyl 3-amino-endo-8-azabicyclo[3.2.1]octane-8-carboxylate (Preparation 4) (3.0 g, 13.2 mmol), 4-ethoxy-3-nitropyridine hydrochloride (2.7 g, 13.2 mmol) and N-ethyl-N,N-diisopropylamine (1.89 g, 14.6 mmol) were dissolved in 1-methyl-2-pyrrolidinone (5 ml) and heated at 120° C. for 18 hours. The cooled reaction mixture was diluted with ethyl acetate (150 ml) and washed with water (3×50 ml), saturated aqueous sodium hydrogen carbonate solution (50 ml) and brine (30 ml). The organic layer was dried (MgSO$_4$) and the solvent removed by evaporation under reduced pressure. This residue was triturated with diethyl ether and filtered to afford the title compound as a yellow solid (1.5 g).

$^1$H-NMR (300 MHz, CDCl$_3$): δ: 1.40–2.50 (17H, m), 3.90–4.05 (1H, q), 4.15–4.50 (2H, m), 6.60 (1H, d), 8.35 (1H, d), 8.75–9.00 (1H, d), 9.25 (1H, s) ppm.

LRMS: m/z 349 (MH$^+$).

Preparation 30

1-endo-(8-Acetyl-8-azabicyclo[3.2.1]oct-3-yl)-2-methyl-1H-imidazo[4,5-c]pyridine

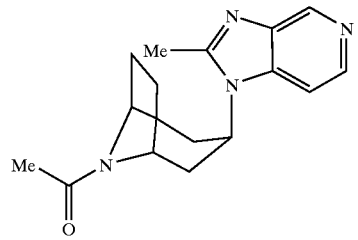

tert-Butyl 3-endo-[(3-nitro-4-pyridinyl)amino]-8-azabicyclo[3.2.1]octane-8-carboxylate (Preparation 29) (4.40 g, 12.6 mmol) and iron powder (2.11 g, 37.8 mmol) were dissolved in glacial acetic acid (50 ml) and the mixture heated to 60° C. for two hours. Acetic anhydride (8 ml) was then added and the mixture heated to 140° C. for 18 hours. The cooled reaction mixture was filtered through a pad of Arbocel® and solvent was removed under reduced pressure The residue was partitioned between dichloromethane (200 ml) and water (200 ml) and the mixture adjusted to pH 9 with 2 N aqueous sodium hydroxide solution. The mixture was again filtered through a pad of Arbocel® and the organic phase separated. The aqueous layer was extracted with dichloromethane (100 ml) and the combined organic extracts dried (MgSO$_4$). Solvent was evaporated under reduced pressure and the residue triturated with ethyl acetate, filtered and dried (MgSO$_4$) to give the title compound as a white solid (3.27 g).

$^1$H-NMR (400 MHz, CDCl$_3$): δ: 1.80–2.35 (9H, m), 2.45–2.70 (5H, m), 4.10–4.25 (1H, m), 4.35 (1H, t), 4.90 (1H, t), 7.22 (1H, d), 8.35 (1H, d), 8.95 (1H, s) ppm.

LRMS: m/z 285 (MH$^+$).

Preparation 31

1-endo-(8-Acetyl-8-azabicyclo[3.2.1]oct-3-yl)-5-benzyl-2-methyl-4,5,6,7-tetrahydro-1H-imidazo[4.5-c]pyridine

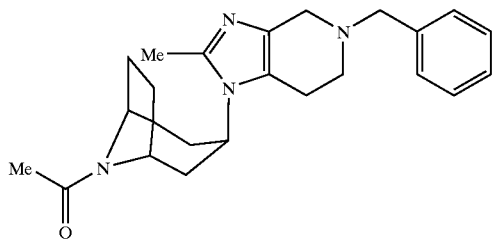

Benzyl bromide (1.78 g, 10.4 mmol) was added to a solution of 1-endo-(8-acetyl-8-azabicyclo[3.2.1]oct-3-yl)-2-methyl-1H-imidazo[4,5-c]pyridine (Preparation 30) (2.47 g, 8.7 mmol) in ethanol (20 ml) and the mixture stirred at room temperature for 48 hours. The reaction mixture was then cooled to −70° C. and sodium borohydride (0.33 g, 8.7 mmol) added portionwise over ten minutes. After one hour at −70° C. the reaction mixture was allowed to warm to −40° C. then re-cooled to −70° C. and further sodium borohydride (0.33 g, 8.7 mmol) added. After an additional hour at −70° C. water (10 ml) was added and the reaction mixture allowed to warm to room temperature. The ethanol was evaporated under reduced pressure and the aqueous residue extracted with dichloromethane (3×25 ml). The combined organic extracts were dried (MgSO$_4$) and solvent evaporated under reduced pressure. The residue was purified by flash column chromatography on silica gel eluting with a solvent gradient of ethyl acetate:methanol:diethylamine (100:0:2, by volume, changing to 98:2:2 then 95:5:2). Product containing fractions were evaporated to afford the title compound as a white foam (2.23 g).

$^1$H-NMR (400 MHz, CDCl$_3$): δ: 1.60–1.85 (4H, m), 1.95–2.20 (5H, m), 2.30 (3H, s), 2.35–2.75 (6H, m), 3.45 (2H, s), 3.65 (2H, s), 3.90 (1H, m), 4.20 (1H, t), 4.80 (1H, t), 7.15–7.35 (5H, m) ppm.

LRMS: m/z 379 (MH$^+$).

Preparation 32

1-endo-(8-Azabicyclo[3.2.1]oct-3-yl)-5-benzyl-2-methyl-4,5,6,7-tetrahydro-1H-imidazo[4,5-c]pyridine

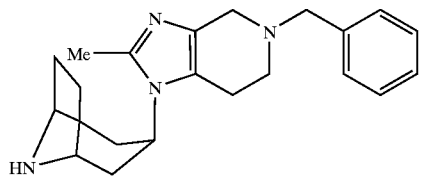

1-endo-(8-Acetyl-8-azabicyclo[3.2.1]oct-3-yl)-5-benzyl-2-methyl-4,5,6,7-tetrahydro-1H-imidazo[4,5-c]pyridine (Preparation 31) (2.23 g, 5.89 mmol) was dissolved in 6N aqueous hydrochloric acid (30 ml) and heated under reflux for 18 hours. The cooled reaction mixture was adjusted to pH10 by the addition of 2N aqueous sodium hydroxide solution and extracted with dichloromethane (2×50 ml). The combined organic extracts were dried (MgSO$_4$) and solvent evaporated under reduced pressure. The residue was purified by flash column chromatography on silica gel eluting with a solvent gradient of dichloromethane:methanol:diethylamine (100:0:0.5, by volume, changing to 93:7:1). Product containing fractions were evaporated to afford the title compound as a white foam (1.47 g).

$^1$H-NMR (400 MHz, CDCl$_3$): δ: 1.40–1.85 (7H, m), 2.30–2.40 (5H, m), 2.60–2.75 (4H, m), 3.45 (2H, s), 3.60–3.70 (4H, m), 4.30 (1H, m), 7.20–7.35 (5H, m) ppm.

LRMS (electrospray): m/z [M+H]$^+$ 337.

Preparation 33 tert-Butyl (1S)-3-[3-endo-(5-benzyl-2-methyl-4,5,6,7-tetrahydro-1H-imidazo[4,5-c]pyridin-1-yl)-8-azabicyclo[3.2.1]oct-8-yl]-1-phenylpropylcarbamate

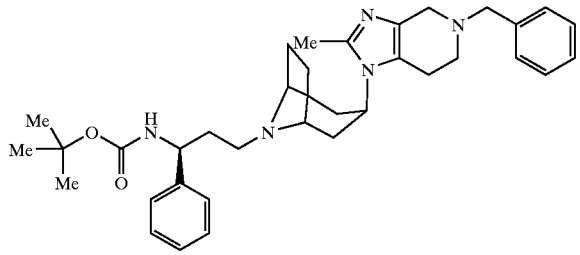

Acetic acid (0.14 g, 2.37 mmol) was added to a stirred solution of 1-endo-(8-azabicyclo[3.2.1]oct-3-yl)-5-benzyl-2-methyl-4,5,6,7-tetrahydro-1H-imidazo[4,5-c]pyridine (Preparation 32) (0.8 g, 2.37 mmol) and tert-butyl (1S)-3-oxo-1-phenylpropylcarbamate (WO0039125) (0.711 g, 2.85 mmol) dissolved in dichloromethane (12 ml) under nitrogen at room temperature. Sodium triacetoxyborohydride (0.60 g, 2.85 mmol) was then added and the reaction was held at room temperature for 18 hours. The reaction mixture was partitioned between saturated aqueous sodium hydrogencarbonate solution (50 ml) and dichloromethane (50 ml). The organic phase was removed and the aqueous phase was washed with dichloromethane (50 ml). The combined organic phases were dried (MgSO$_4$) and the solvent was evaporated under reduced pressure. The residue was purified by flash column chromatography on silica gel eluting with a solvent gradient of dichloromethane:methanol:concentrated aqueous ammonia (99:1:0.1, by volume, changing to 90:10:1). Product containing fractions were evaporated to afford the title compound as a white foam (1.17 g).

¹H NMR (400 MHz, CDCl₃): δ: 7.40–7.20 (10H, m), 5.80 (1H, m), 4.80 (1H, m), 4.40 (1H, m), 3.65 (2H, s), 3.50 (2H, m), 3.40–3.20 (2H, m), 2.70–2.60 (4H, m), 2.55–2.35 (5H, m), 2.20 (2H, t), 2.10–1.10 (17H, m) ppm.

LRMS (electrospray): m/z [M+H]⁺ 570.

Preparation 34 tert-Butyl (1S)-3-[3-endo-(2-methyl-4,5,6,7-tetrahydro-1H-imidazo[4,5-c]pyridin-1-yl)-8-azabicyclo[3.2.1]oct-8-yl]-1-phenylpropylcarbamate

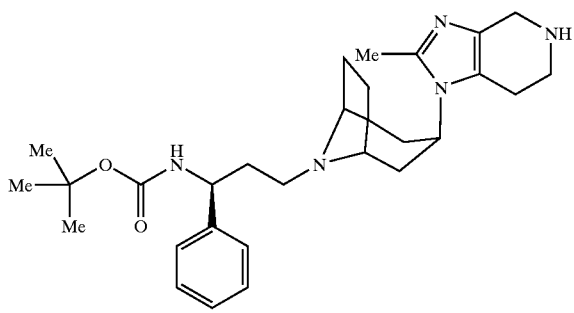

A mixture of tert-butyl (1S)-3-[3-endo-(5-benzyl-2-methyl-4,5,6,7-tetrahydro-1H-imidazo[4,5-c]pyridin-1-yl)-8-azabicyclo[3.2.1]oct-8-yl]-1-phenylpropylcarbamate (Preparation 33) (1.15 g, 2.02 mmol), ammonium formate (0.63 g, 10.1 mmol) and 20% w/w palladium hydroxide on carbon (0.15 g) in ethanol (25 ml) was heated to 60° C. After one hour additional ammonium formate (0.63 g, 10.1 mmol) was added and heating continued at 60° C. for a further hour. This process was repeated three times. The cooled reaction mixture was then filtered through Arbocel® and the filtrate evaporated under reduced pressure. The residue was partitioned between dichloromethane (100 ml) and saturated aqueous sodium hydrogencarbonate solution (50 ml), the organic phase separated and washed with water (30 ml). The organic layer was dried (MgSO₄) and solvent evaporated under reduced pressure. The residue was purified by flash column chromatography on silica gel eluting with a solvent gradient of dichloromethane:methanol:concentrated aqueous ammonia (99:1:0.1 changing to 93:7:1). Product containing fractions were evaporated to afford the title compound as a white foam (0.85 g).

¹H NMR (400 MHz, CDCl₃): δ: 7.35–7.15 (5H, m), 5.75 (1H, m), 4.90–4.70 (1H, m), 4.45 (1H, m), 3.80 (2H, s), 3.40–3.20 (2H, m), 3.15–3.00 (2H, m), 2.70–2.60 (2H, m), 2.50–2.35 (5H, m), 2.30–1.70 (7H, m), 1.65–1.10 (13H, m) ppm.

LRMS (electrospray): m/z [M+H]⁺ 480.

Preparation 35

Methyl 1-endo-(8-{(3S)-3-[(tert-butoxycarbonyl)amino]-3-phenylpropyl}-8-azabicyclo[3.2.1]oct-3-yl)-2-methyl-4,5,6,7-tetrahydro-1H-imidazo[4,5-c]pyridine-5-carboxylate

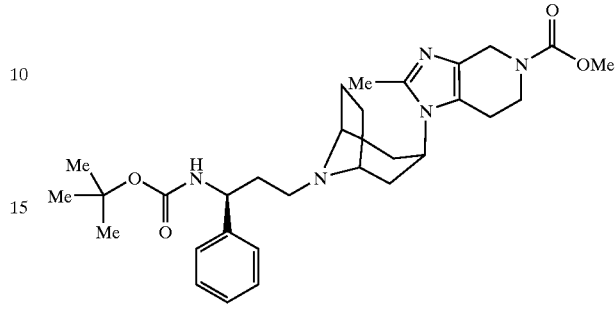

Methyl chloroformate (0.078 ml, 1.02 mmol) was added to a solution of tert-butyl (1S)-3-[3-endo-(2-methyl-4,5,6,7-tetrahydro-1H-imidazo[4,5-c]pyridin-1-yl)-8-azabicyclo[3.2.1]oct-8-yl]-1-phenylpropylcarbamate (Preparation 34) (0.44 g, 0.92 mmol) in dichloromethane (4 ml) under nitrogen. The reaction was stirred at room temperature for 1.5 hours and then washed with saturated aqueous sodium hydrogencarbonate solution (10 ml). The organic phase was removed and the aqueous layer extracted with more dichloromethane (2×10 ml). The combined dichloromethane extracts were dried (MgSO₄) and the solvent was removed under reduced pressure. The residue was purified by flash column chromatography on silica gel eluting with a solvent mixture of dichloromethane:methanol:concentrated aqueous ammonia (99:1:0.1 changing to 93:7:1). Product containing fractions were evaporated to afford the title compound as a white foam (0.51 g).

¹H NMR (400 MHz, CDCl₃): δ: 7.30–7.20 (5H, m), 5.65 (1H, m), 4.90–4.70 (1H, m), 4.50–4.30 (3H, m), 3.80–3.60 (5H, m), 3.40–3.20 (2H, m), 2.65 (2H, m), 2.50–2.35 (5H, m), 2.25 (2H, m), 2.15–1.10 (17H, m) ppm.

LRMS (electrospray): m/z [M+H]⁺ 538.

Preparation 36

Methyl 1-endo-{8-[(3S)-3-amino-3-phenylpropyl]-8-azabicyclo[3.2.1]oct-3-yl}-2-methyl-4,5,6,7-tetrahydro-1H-imidazo[4,5-c]pyridine-5-carboxylate trihydrochloride

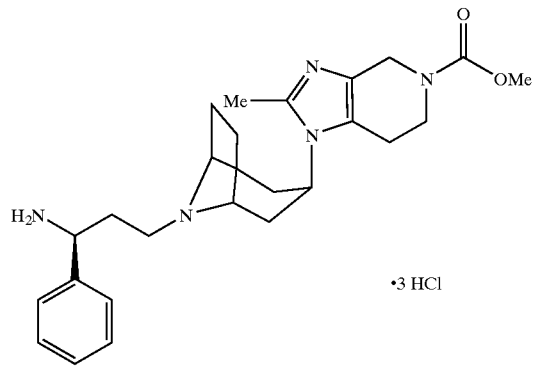

Hydrogen chloride gas was bubbled through a solution of methyl 1-endo-(8-{(3S)-3-[(tert-butoxycarbonyl)amino]-3- phenylpropyl}-8-azabicyclo[3.2.1]oct-3-yl)-2-methyl-4,5,6,7-tetrahydro-1H-imidazo[4,5-c]pyridine-5-carboxylate (Preparation 35) (0.5 g, 0.93 mmol) in dichloromethane (10 ml) and methanol (1 ml) at 0° C. until the solution was saturated. The reaction mixture was then allowed to warm to room temperature and stirred for one hour. Solvent was evaporated under reduced pressure and the residue suspended in dichloromethane (10 ml). This process was repeated three times to give the title compound as a white solid (0.512 g).

$^1$H NMR (400 MHz, d$_6$-DMSO): δ: 11.30–11.10 (1H, br s), 8.90–8.60 (3H, br s), 7.60 (2H, m), 7.50–7.35 (3H, m), 5.80–5.60 (1H, m), 4.50–4.35 (3H, m), 4.20–4.00 (2H, m), 3.80–3.30 (9H, m), 3.25–3.10 (1H, m), 3.00–1.90 (13H, m) ppm.

LRMS (electrospray): m/z [M+H]$^+$ 438.

Preparation 37 tert-Butyl (1S)-3-[3-endo-(5-benzyl-2-methyl-4,5,6,7-tetrahydro-1H-imidazo[4,5-c]pyridin-1-yl)-8-azabicyclo[3.2.1]oct-8-yl]-1-(3-fluorophenyl)propylcarbamate

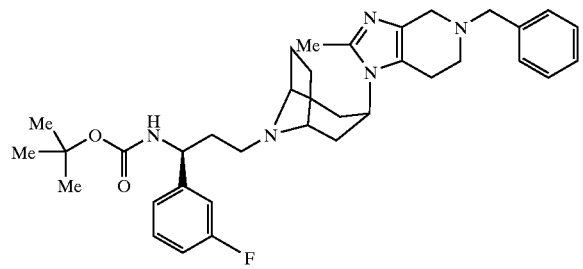

Acetic acid (0.39 g, 6.4 mmol) was added to a stirred solution of 1-endo-(8-azabicyclo[3.2.1]oct-3-yl)-5-benzyl-2-methyl-4,5,6,7-tetrahydro-1H-imidazo[4,5-c]pyridine (Preparation 32) (2.16 g, 6.4 mmol) and tert-butyl (1S)-1-(3-fluorophenyl)-3-oxopropylcarbamate (Preparation 15) (2.06 g, 7.7 mmol) dissolved in dichloromethane (25 ml) under nitrogen at room temperature. Sodium triacetoxyborohydride (1.63 g, 7.7 mmol) was then added and the reaction was held at room temperature for 2 hours. The reaction mixture was partitioned between saturated aqueous sodium hydrogencarbonate solution (50 ml) and dichloromethane (50 ml). The organic phase was removed and the aqueous phase was washed with dichloromethane (50 ml). The combined organic phases were dried (MgSO$_4$) and the solvent was evaporated under reduced pressure. The residue was purified by flash column chromatography on silica gel eluting with a solvent gradient of dichloromethane:methanol:concentrated aqueous ammonia (99:1:0.1, by volume, changing to 96:4:0.4). Product containing fractions were evaporated to afford the title compound as a white foam (2.56 g).

$^1$H NMR (400 MHz, CDCl$_3$): δ: 7.40–7.20 (6H, m), 7.10–6.90 (3H, m), 6.20–5.95 (1H, m), 5.00–4.70 (1H, m), 4.55–4.40 (1H, m), 3.70 (2H, s), 3.60–3.47 (2H, m), 3.45–3.25 (2H, m), 2.85–2.67 (4H, m), 2.65–2.40 (5H, m), 2.38–2.20 (2H, t), 2.18–1.20 (17H, m) ppm.

LRMS (electrospray): m/z [M+H]$^+$ 588.

Preparation 38 tert-Butyl (1S)-3-[3-endo-(2-methyl-4,5,6,7-tetrahydro-1H-imidazo[4,5-c]pyridin-1-yl)-8-azabicyclo[3.2.1]oct-8-yl]-1-(3-fluorophenyl)propylcarbamate

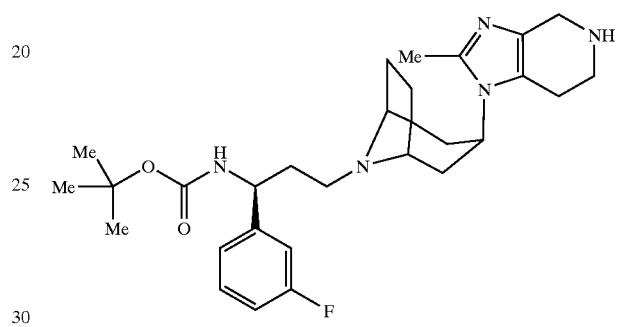

A mixture of tert-butyl (1S)-3-[3-endo-(5-benzyl-2-methyl-4,5,6,7-tetrahydro-1H-imidazo[4,5-c]pyridin-1-yl)-8-azabicyclo[3.2.1]oct-8-yl]-1-(3-fluorophenyl)propylcarbamate (Preparation 37) (2.55 g, 4.34 mmol), ammonium formate (2.73 g, 43.4 mmol) and 20% w/w palladium hydroxide on carbon (0.25 g) in ethanol (35 ml) was heated to 60° C. After one hour additional ammonium formate (0.63 g, 10.1 mmol) was added and heating continued at 60° C. for a further two hours. The cooled reaction mixture was then filtered through Arbocel® and the filtrate evaporated under reduced pressure. The residue was partitioned between dichloromethane (100 ml) and saturated aqueous sodium hydrogencarbonate solution (50 ml), the organic phase separated and washed with water (30 ml). The organic layer was dried (MgSO$_4$) and solvent evaporated under reduced pressure. The residue was purified by flash column chromatography on silica gel eluting with a solvent gradient of dichloromethane:methanol:concentrated aqueous ammonia (99:1:0.1 changing to 93:7:1). Product containing fractions were evaporated to afford the title compound as a white foam (1.50 g).

$^1$H NMR (400 MHz, CDCl$_3$): δ: 7.35–7.25 (1H, m), 7.10–6.90 3H, m( ), 6.20–5.80 (1H, m), 4.95–4.65 (1H, m), 4.60–4.40 (1H, m), 3.85 (2H, s), 3.45–3.30 (2H, m), 3.20–3.10 (2H, m), 2.75–2.65 (2H, m), 2.60–2.40 (5H, m), 2.35–1.20 (20H, m) ppm.

LRMS (electrospray): m/z [M+H]$^+$ 498.

Preparation 39

Methyl 1-endo-(8-{(3S)-3-[(tert-butoxycarbonyl)amino]-3-(3-fluorophenyl)propyl}-8-azabicyclo[3.2.1]oct-3-yl)-2-methyl-4,5,6,7-tetrahydro-1H-imidazo[4,5-c]pyridine-5-carboxylate

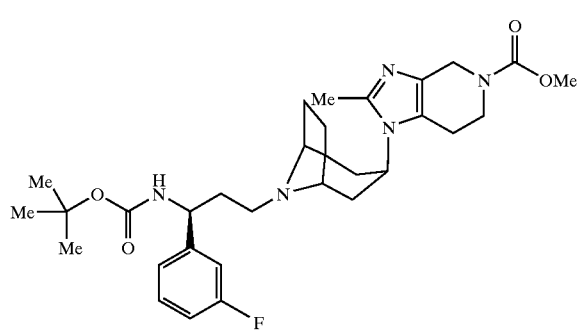

Methyl chloroformate (0.167 g, 1.76 mmol) was added to a solution of tert-butyl (1S)-3-[3-endo-(2-methyl-4,5,6,7-tetrahydro-1H-imidazo[4,5-c]pyridin-1-yl)-8-azabicyclo[3.2.1]oct-8-yl]-1-(3-fluorophenyl)propylcarbamate (Preparation 38) (0.80 g, 1.60 mmol) in dichloromethane (10 ml) under nitrogen at room temperature. The reaction was stirred at room temperature for 1.5 hours and then washed with saturated aqueous sodium hydrogencarbonate solution (10 ml). The organic phase was removed and the aqueous layer extracted with more dichloromethane (2×10 ml). The combined dichloromethane extracts were dried (MgSO$_4$) and the solvent was removed under reduced pressure. The residue was purified by flash column chromatography on silica gel eluting with a solvent mixture of dichloromethane:methanol:concentrated aqueous ammonia (99:1:0.1 changing to 93:7:1). Product containing fractions were evaporated to afford the title compound as a white foam (0.84 g).

$^1$H NMR (400 MHz, CDCl$_3$): δ: 7.35–7.25 (1H, m), 7.10–6.90 (3H, m), 6.10–5.80 (1H, m), 4.95–4.75 (1H, m), 4.60–4.35 (3H, m), 3.85–3.60 (5H, m), 3.45–3.25 (2H, m), 2.75–2.65 (2H, m), 2.60–1.05 (24H, m) ppm.

LRMS (electrospray): m/z [M+H]$^+$ 556.

Preparation 40

Methyl 1-endo-{8-[(3S)-3-amino-3-(3-fluorophenyl)propyl]-8-azabicyclo[3.2.1]oct-3-yl}-2-methyl-4,5,6,7-tetrahydro-1H-imidazo[4,5-c]pyridine-5-carboxylate trihydrochloride

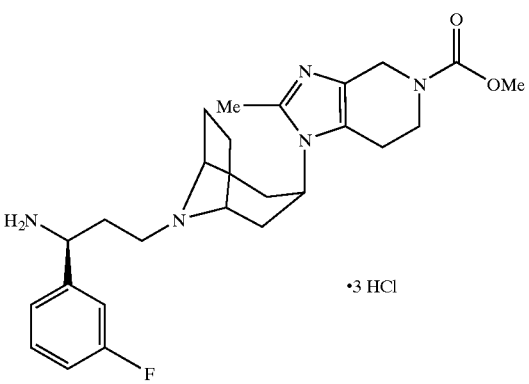

Hydrogen chloride gas was bubbled through a solution of methyl 1-endo-(8-{(3S)-3-[(tert-butoxycarbonyl)amino]-3-(3-fluorophenyl)propyl}-8-azabicyclo[3.2.1]oct-3-yl)-2-methyl-4,5,6,7-tetrahydro-1H-imidazo[4,5-c]pyridine-5-carboxylate (Preparation 39) (0.83 g, 1.50 mmol) in dichloromethane (15 ml) at 0° C. until the solution was saturated. The reaction mixture was then allowed to warm to room temperature and stirred for one hour. Solvent was evaporated under reduced pressure and the residue suspended in dichloromethane (10 ml). This process was repeated three times to give the title compound as a white solid (0.82 g).

$^1$H NMR (400 MHz, d$_6$-DMSO): δ: 11.30–11.10 (1H, br s), 9.10–8.80 (3H, br s), 7.55–7.40 (3H, m), 7.25–7.20 (1H, t), 5.80–5.60 (1H, m), 4.55–4.40 (3H, m), 4.20–4.00 (2H, m), 3.80–3.05 (10H, m), 3.00–1.90 (13H, m) ppm.

LRMS (electrospray): m/z [M+H]$^+$ 456.

Preparation 41

Ethyl (3S)-3-(acetamido)-3-(3-fluorophenyl)propanoate

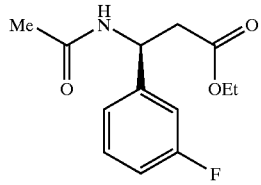

Acetyl chloride (7.9 ml, 111 mmol) in dichloromethane (50 ml) was added dropwise to a cold (0° C.) solution of ethyl (3S)-3-amino-3-(3-fluorophenyl)propanoate (WO99/31099, Scheme 3 page 97) (25.2 g, 102 mmol) in dichloromethane (200 ml). The reaction was stirred for 2 hours at 0° C., then water (100 ml) was added. The reaction mixture was adjusted to pH 1 with 2 N hydrochloric acid and the organic layer separated. The dichloromethane layer was washed with saturated sodium hydrogencarbonate solution (50 ml), water (50 ml) and then dried (MgSO4). Solvent was evaporated under reduced pressure to afford a thick oil which was purified by column chromatography (silica gel, eluting with diethyl ether) to give the title compound as a clear, colourless oil, 25.1 g.

LRMS: m/z 254 (MH+).

Preparation 42

N-[(1S)-1-(3-Fluorophenyl)-3-hydroxypropyl]acetamide

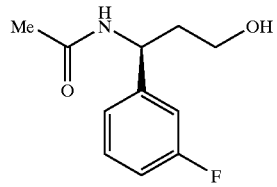

A stirred suspension of ethyl (3S)-3-(acetylamino)-3-(3-fluorophenyl)propanoate (2.5 g, 9.9 mmol) and sodium borohydride (0.76 g, 20 mmol) in THF (20 ml) was heated at 50° C. under a nitrogen atmosphere. Methanol (1.8 ml) was then carefully added dropwise and the reaction mixture heated under reflux for one hour. The reaction was allowed to cool to room temperature then water (10 ml) and aqueous sodium hydroxide solution (1.5 g NaOH in 4 ml water) carefully added dropwise. The solution was extracted with ethyl acetate (3×30 ml) and the combined organic extracts dried (MgSO4) and evaporated to give the title compound as a white solid (2.08 g).

LRMS (electrospray): m/z [M+H]+ 212.

Preparation 43

N-[(1S)-1-(3-Fluorophenyl)-3-oxopropyl]acetamide

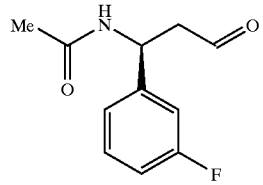

Pyridine sulfur trioxide complex (37.7 g, 237 mmol) was added portionwise over 20 minutes to a stirred cold (0° C.) solution of N-[(1S)-1-(3-fluorophenyl)-3-hydroxypropyl]acetamide (25 g, 118 mmol), DMSO (16.5 ml, 233 mmol) and triethylamine (33 ml, 237 mmol) in dichloromethane (240 ml). After two hours stirring at room temperature, solvent was evaporated under reduced pressure and the residue applied directly to a silica gel column. Eluting with a gradient system starting with ethyl acetate:dichloromethane (50:50 by volume) then ethyl acetate:dichloromethane (80:20 by volume) and finally ethyl acetate gave the title compound as a colourless oil which solidified on standing (13.9 g).

1H NMR (400 MHz, CDCl3): δ: 9.75 (1H, s), 7.30 (1H, m), 7.10–6.90 (3H, m), 6.40 (1H, br s), 5.50 (1H, m), 3.05 (1H, dd), 2.90 (1H, dd), 2.00 (3H, s) ppm.

LRMS (electrospray): m/z [M+H]+ 210.

Preparation 44

Endo-8-Benzyl-8-azabicyclo[3.2.1]oct-3-ylamine

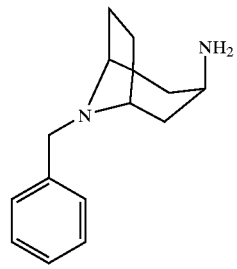

Endo-8-Benzyl-8-azabicyclo[3.2.1]oct-3-ylamine dihydrochloride hemihydrate (100 g, 0.34 mol) was dissolved in water (300 ml) and ethyl acetate (500 ml). The aqueous layer was adjusted to pH 10 by the addition of 10M sodium hydroxide (70 ml), resulting in a 5° C. exotherm. The reaction was stirred at ambient temperature for 15 minutes and the layers separated. The aqueous layer was washed with ethyl acetate (500 ml). The organic layers were combined and washed with water (300 ml), and concentrated under reduced pressure to a pale yellow oil containing traces of ethyl acetate, 64.9 g, 90% yield.

LRMS (Electrospray): m/z=217.2 (MH+)

Preparation 45

Endo-8-Benzyl-N-(3-nitro-4-pyridyl)-8-azabicyclo[3.2.1]oct-3-ylamine

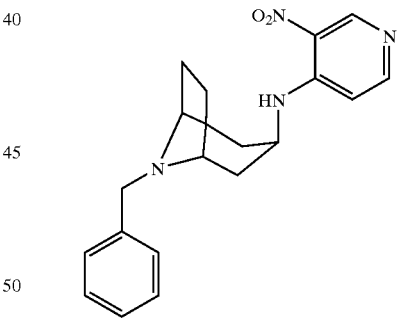

4-Ethoxy-3-nitropyridine.hydrochloride salt (135.3 g, 0.661 mol) was slurried in tert-amyl alcohol (390 ml) at ambient temperature under a nitrogen blanket. 1,8-Diazabicylco[5.4.0]undec-7-ene (192.1 g, 1.26 mol) was added to the reaction mixture, followed by a solution of the title compound from preparation 44 (130 g, 0.601 mol) in tert-amyl alcohol (260 ml). The resultant solution was heated to reflux for 4.5 hours. The solution was cooled to ambient temperature and the resultant thick yellow slurry stirred at ambient temperature for 12 hours and further at 5° C. for 2 hours. The solid was filtered off and dried in an oven under reduced pressure at 50° C. overnight, to give the title compound, 132.8 g, 91% yield.

LRMS (Electrospray): m/z=339.3 (MH+)

Preparation 46

N4-(endo-8-Benzyl-8-azabicyclo[3.2.1]oct-3-yl)pyridine-3,4-diamine

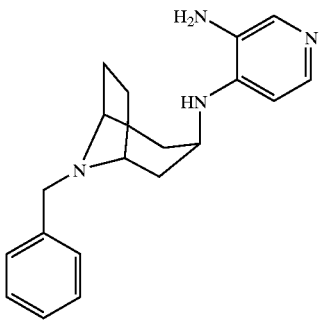

The title compound from Preparation 45 (150.0 g, 0.123 mol) was slurried in methanol (750 ml). 10 wt % of 5% Palladium on carbon (15.0 g) was added. The mixture was stirred under an atmosphere of hydrogen at 50 psi, 25° C. for 2.5 hours. A sample was taken and analysis by tlc showed that the reaction was complete. The reaction was filtered through ArbocelTM (filtration aid) and the filter pad washed with methanol (750 ml). The methanol was evaporated under reduced pressure and replaced with ethyl acetate (1.5 L) to leave a total volume of 300 ml ethyl acetate. The mixture was granulated at ambient temperature for 2 hours and further at 0° C. for 1 hour. The solid was filtered off and washed with ethyl acetate (75 ml) and dried in an oven under reduced pressure, at 50° C. overnight, to give the title compound as a white solid, 105.6 g, 78%.

LRMS (Electrospray): m/z=309.3 (MH$^+$)

Preparation 47

1-(endo-8-Benzyl-8azabicyclo[3.2.1]oct-3-yl)-2-methyl-1H-imidazo[4,5-c]pyridine

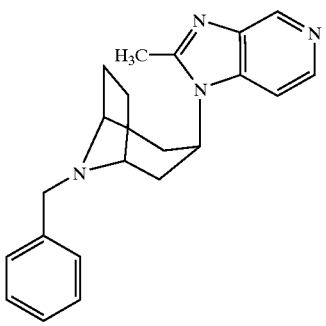

The title compound from Preparation 46 (32.0 g, 0.103 mol) was slurried in toluene (96 ml) at ambient temperature under a nitrogen blanket. Acetic anhydride (64 ml) and acetic acid (160 ml) were added resulting in a 10° C. exotherm. The mixture was heated to reflux overnight. A sample was taken for analysis by tlc, which showed the reaction was complete. The reaction solution was allowed to cool to ambient temperature. The acetic acid and toluene were removed under reduced pressure to give a brown oil. The oil was dissolved in dichloromethane (320 ml) and water (160 ml) to give a two-phase solution. The aqueous layer was adjusted to pH 10 by the addition of 10M sodium hydroxide. The layers were separated and the aqueous layer washed with dichloromethane (160 ml). The organics were combined, washed with water (240 ml) and concentrated under reduced pressure, replacing with ethyl acetate (320 ml) to leave approximately 96 ml ethyl acetate. The resultant slurry was granulated at 0° C. for 15 minutes. Heptane (96 ml) was added, and the mixture was granulated at 0° C. for 2 hours. The beige solid was collected by filtration, washed with 1:1 ethyl acetate/heptane (32 ml) and dried in an oven under reduced pressure, at 50° C. overnight, to give the title compound, 30 g, 88%.

LRMS (Electrospray): m/z=333.3 (MH$^+$)

Preparation 48

Methyl 1-(endo-8-benzyl-8-azabicyclo[3.2.1]oct-3-yl)-2-methyl-4,5,6,7-tetrahydro-1H-imidazo[4,5-c]pyridine-5-carboxylate

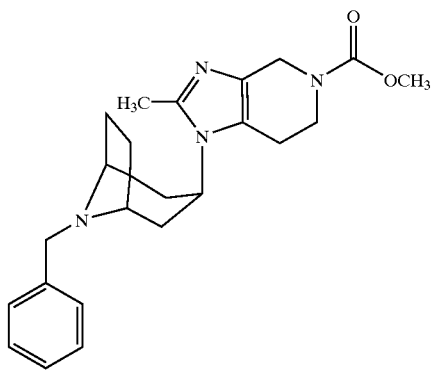

The title compound from Preparation 47 (59.0 g, 0.177 mol) was slurried in ethanol (280 ml) and water (15 ml) at ambient temperature under a nitrogen blanket. The mixture was cooled to −70° C. Methyl chloroformate (16.5 ml, 0.213 mol) was added over 10 minutes maintaining the temperature below −50° C. The reaction was cooled to −70° C. and stirred for 45 minutes. Lithium borohydride was added as a 2M solution in tetrahydrofuran (107 ml, 0.213 mol) over 15 minutes, maintaining the temperature below −40° C. A sample was taken for analysis by tlc, which showed the reaction wad complete. The mixture was allowed to warm to −20° C. During this time gas evolution was observed. Water (295 ml) was added allowing the mixture to warm to ambient temperature and stir for 15 minutes. Dichloromethane (590 ml) was added and the resultant two-phase solution separated. The aqueous layer was re-extracted with dichloromethane (295 ml). The organics were combined and washed with saturated sodium chloride solution (148 ml). The dichloromethane was removed under reduced pressure, replacing with ethyl acetate (590 ml) to leave a total volume of 118 ml ethyl acetate. The resultant slurry was granulated at ambient temperature for 1.5 hours, then further at 0° C. for 1 hour. The solid was collected by filtration, washed with ethyl acetate (30 ml) and dried in an oven under reduced pressure at 50° C. overnight, to give the title compound as an off white solid, 61.6 g, 89%.

LRMS (Electrospray): m/z=393.4 (MH$^+$)

Preparation 49

Methyl 1-(endo-8-azabicyclo[3.2.1]oct-3yl)2-methyl-4,5,6,7-tetrahydro-1H-imidazo[4,5-c]pyridine-5-carboxylate

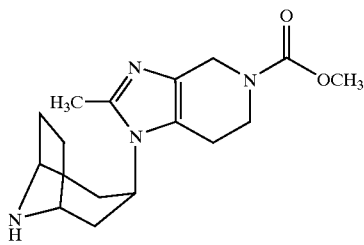

The title compound from Preparation 48 (161.7 g, 0.412 mol) was slurried in methanol (1.62 L) at ambient temperature. 10 wt % of 5% Palladium on carbon (16.2 g) was added. The mixture was stirred under an atmosphere of hydrogen at 50 psi, 50° C., overnight. A sample was taken for analysis by tlc, which showed that the reaction was complete. The reaction mixture was filtered through Arbocel™ (filtration aid) and the filter pad washed with methanol (1.0 L). The methanol was removed under reduced pressure, replacing with ethyl acetate (1.62 L) then concentrated to dryness, to give the title compound as a pale yellow oil, 118.6 g, 95%.

LRMS (Electrospray): m/z=305.3 (MH+)

Preparation 50

Ethyl (S)-3-[benzyloxycarbonyl)amino]-3-(3-fluorophenyl)propanoate

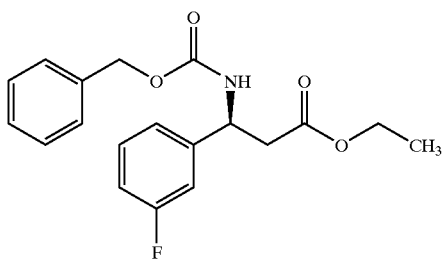

Ethyl (S)-3-amino-3-(3-fluorophenyl)propanoate hydrochloride (1.0 kg, 4.04 mol) was slurried in ethyl acetate (5.0 L) at ambient temperature. Saturated sodium carbonate solution (5.0 L) and water (5.0 L) were added. The resultant two-phase solution was cooled to 10° C. Benzyl chloroformate (605 ml, 1.05 mol) was added to the mixture maintaining the temperature below 20° C. The mixture was stirred at 20° C. for 20 minutes. A sample was taken and analysed by HPLC, which showed the reaction was complete. The aqueous layer was adjusted to pH 9 by the addition of saturated sodium carbonate. The phases were separated. The aqueous layer was extracted further with ethyl acetate (5.0 L). The organics were combined and washed with water (5.0 L). The ethyl acetate was removed under reduced pressure to give the title compound as a waxy white solid, 1.39 kg, 100%.

LRMS (Electrospray): m/z=346.3 (MH+)

Preparation 51

Benzyl (S)-1-(3-fluorophenyl)-3-hydroxypropylcarbamate

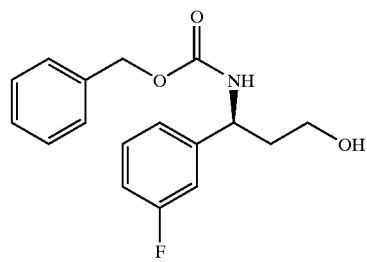

The title compound from Preparation 50 (13.95 g, 0.404 mol) was dissolved in tetrahydrofuran (98 ml) at ambient temperature under a nitrogen blanket. Sodium borohydride was added, resulting in a 10° C. exotherm. The reaction was heated to 50° C. and methanol added (3.3 ml, 0.0808 mol) over 5 minutes maintaining the temperature at 50° C. Some off gassing and frothing was observed. The reaction was heated to reflux for 1.5 hours. A sample was taken and analysed by HPLC, which showed that the reaction was complete. The mixture was cooled to ambient temperature. 2M sodium hydroxide (98 ml) was added and the resultant two-phase solution stirred for 15 minutes. The phases were separated. The aqueous layer was further extracted with tetrahydrofuran (50 ml). The organics were combined and washed with saturated sodium chloride solution (70 ml). The tetrahydrofuran was removed under reduced pressure and replaced with ethyl acetate (70 ml). The ethyl acetate solution was concentrated to dryness under reduced pressure to azeotropically remove any remaining water. The title compound was isolated as a white waxy solid, LRMS (Electrospray): m/z=304.2 (MH+)

Preparation 52

Benzyl (S)-1-(3-fluorophenyl)-3-hydroxypropylcarbamate

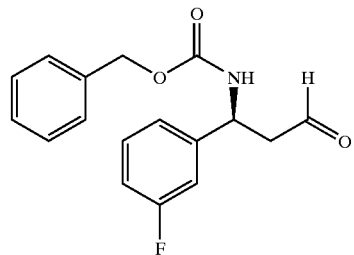

The title compound from Preparation 51, (165.0 g, 0.72 mol) was dissolved in ethyl acetate (1.65 L) at ambient temperature under a nitrogen blanket. Water (803 ml), sodium bicarbonate (175 g, 2.10 mol), TEMPO (1.13 g, 0.0072 mol) and sodium bromide (76.1 g, 0.74 mol) were added. The mixture was cooled to 5° C. Sodium hypochlorite solution (1.62M, 469 ml, 0.76 mol) was added over 1 hour maintaining the temperature below 10° C. The two-phase mixture was stirred for 20 minutes. A sample was taken for analysis by tlc, which showed the reaction was complete. The phases were separated. The aqueous layer was extracted further with ethyl acetate (401 ml). The organics were combined and washed with 10 wt % potassium hydrogen sulfate solution (803 ml), followed by 10 wt % sodium thiosulfate solution (401 ml) and saturated sodium chloride solution (401 ml). Frothing and off gassing observed during the potassium hydrogen sulfate wash. The ethyl acetate was removed under reduced pressure to yield the title compound as a yellow oil, 139.3 g, 89%.

LRMS (Electrospray): m/z=302.2 (MH$^+$)

Preparation 53

Methyl 1-(endo-8-{(3S)-3-[benzyloxycarbonyl)amino]-3-(3-fluorophenyl)propyl}-8-azabicyclo[3.2.1]oct-3-yl)-2-methyl-4,5,6,7-tetrahydro-1H-imidazo[4,5-c]pyridine-5-carboxylate

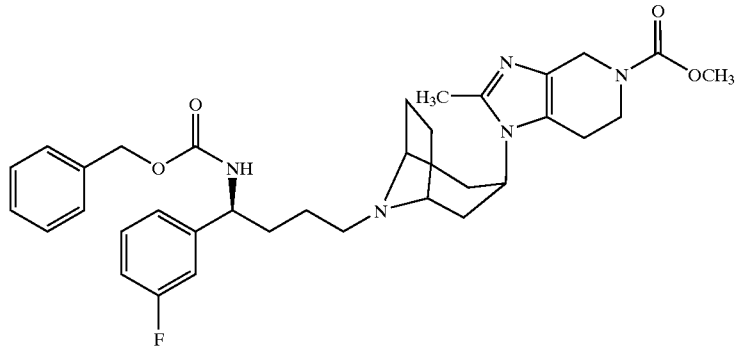

The title compound from Preparation 49 (3.20 g, 0.0105 mol) and sodium triacetoxyborohydride (3.35 g, 0.0158 mol) were slurried in ethyl acetate (35 ml) at ambient temperature under a nitrogen blanket. The title compound from Preparation 52 (3.48 g, 0.0116 mol) was added as a solution in tetrahydrofuran (7 ml) over 15 minutes. The mixture was stirred overnight. A sample was taken for analysis by tlc, which showed that the reaction was complete. 2M sodium hydroxide (14 ml) was added over 5 minutes. The aqueous layer of the resultant two-phase solution was adjusted to pH 10, by the addition of 10M sodium hydroxide (7.5 ml). The phases were separated. The organic layer was washed with water (17.5 ml). The ethyl acetate was removed under reduced pressure to give the title compound as a yellow oil, 5.3 g, 77%.

LRMS (Electrospray): m/z=590.5 (MH$^+$)

Preparation 54

Methyl 1-{endo-8-[(3S)-3-amino-3-(3-fluorophenyl)propyl]-8-azabicyclo[3.2.1]oct-3-yl}-2-methyl-4,5,6,7-tetrahydro-1H-imidazo-[4,5-c]pyridine-5-carboxylate

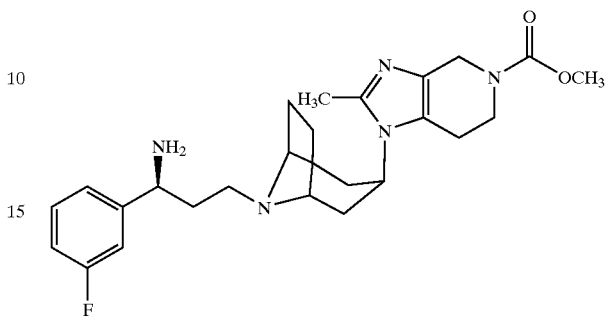

The title compound from Preparation 53 was dissolved in methanol (26.5 ml). 10 wt % Palladium hydroxide (0.53 g) was added. The mixture was stirred under an atmosphere of hydrogen at 50 psi, at ambient temperature for 4 hours. A sample was taken and tlc analysis showed that the reaction was complete. The reaction mixture was filtered through Arbocel™ (filtration aid) and the filter pad washed with methanol (26.5 ml). The methanol was evaporated under reduced pressure to give the title compound as a yellow oil, 3.81 g, 93%.

LRMS (Electrospray): m/z=456.4 (MH$^+$)

Biological Activity

The ability of the compounds of formula (I) to inhibit binding of HIV envelope protein (gp120) to CCR5 receptors was determined by the procedure described in Example 1 of EP 1 118 858 A2. The compounds of formula (I) exhibited potent activity (nanomolar (nM) IC$_{50}$ values) in this assay.

In particular, in this assay the compounds of Examples 9 and 30 both had an IC$_{50}$ of 7 nM; the compound of Example 17 had an IC$_{50}$ of 15 nM; the compound of Example 33 had an IC$_{50}$ of 23 nM; and the compound of Example 44 had an IC$_{50}$ of 14 nM.

Powder X-Ray Diffraction (PXRD) Data

Methyl 1-{endo-8-[(3S)-3-acetamido-3-(3-fluorophenyl)propyl]-8-azabicyclo[3.2.1]oct-3-yl}-2-methyl-4,5,6,7-tetrahydro-1H-imidazo[4,5-c]pyridine-5-carboxylate monohydrate The PXRD pattern for the title compound, prepared in the same manner as the compound of Example 44, was obtained using a Siemens D5000 diffractometer (λ=1.54178 Å) over the 2θ angular range 2–55° with a 0.02° step size. Data was collected at each step for 5 seconds. Peak positions were determined by use of silicon powder (15% wt.) as an internal reference standard (Table 1).

TABLE 1

PXRD Peak Data for the title compound

| 2-Theta ° | Intensity % |
|---|---|
| 7.141 | 3.0 |
| 9.087 | 11.3 |
| 11.666 | 5.2 |
| 12.719 | 25.4 |
| 13.027 | 23.4 |
| 14.107 | 11.9 |
| 14.475 | 29.4 |
| 15.530 | 15.4 |
| 15.935 | 20.7 |
| 17.191 | 7.7 |
| 17.522 | 11.6 |
| 17.923 | 41.2 |
| 18.137 | 21.9 |
| 19.096 | 40.9 |
| 19.589 | 10.2 |
| 20.624 | 100.0 |
| 21.516 | 47.6 |
| 22.208 | 21.6 |
| 23.210 | 36.1 |
| 23.419 | 27.5 |
| 24.310 | 12.3 |
| 24.968 | 13.6 |
| 26.241 | 25.7 |
| 26.674 | 13.9 |
| 26.959 | 12.9 |
| 27.505 | 5.4 |
| 27.937 | 7.4 |
| 28.397 | 11.4 |
| 28.737 | 15.0 |
| 29.179 | 24.3 |
| 30.007 | 21.1 |
| 30.947 | 5.4 |
| 31.941 | 11.0 |
| 32.631 | 17.7 |
| 33.402 | 5.6 |
| 34.808 | 9.0 |
| 36.010 | 8.3 |
| 36.910 | 10.6 |
| 37.746 | 9.6 |
| 38.454 | 6.4 |
| 39.117 | 12.5 |
| 41.619 | 10.4 |
| 41.857 | 11.3 |
| 43.324 | 8.0 |
| 44.002 | 8.8 |
| 45.309 | 10.8 |
| 47.667 | 7.1 |
| 49.618 | 8.4 |
| 51.032 | 7.0 |
| 52.670 | 7.2 |

The PXRD patterns for the compounds of both Examples 44 and 45 were consistent with the above PXRD data.

Examples 46–49

The PXRD pattern simulations involving 2-theta angles and relative intensities were calculated from single crystal structures using the Cerius$^2$ Diffraction-Crystal Module. The simulation parameters were:
Wavelength=1.54178 Å
Polarisation Factor=0.5
Crystallite Size=500×500×500 Å
Lorentzian Peak Shape The main peaks (in degrees 2-theta) of the simulated PXRD patterns are listed in tables (2–5).

TABLE 2

Simulated PXRD Peak Data for the compound of Example 46

| 2-Theta ° | Intensity % |
|---|---|
| 6.768 | 76.1 |
| 10.076 | 21.7 |
| 10.671 | 36.9 |
| 11.054 | 17.3 |
| 13.079 | 8.7 |
| 13.801 | 6.4 |
| 15.807 | 5.6 |
| 16.552 | 21.4 |
| 16.975 | 80.7 |
| 17.331 | 25.5 |
| 17.848 | 38.9 |
| 18.422 | 55.2 |
| 18.880 | 100.0 |
| 19.424 | 24.7 |
| 20.070 | 98.8 |
| 20.799 | 39.1 |
| 21.100 | 21.9 |
| 21.581 | 58.5 |
| 22.527 | 23.0 |
| 22.894 | 30.2 |
| 23.341 | 45.6 |
| 23.740 | 6.0 |
| 24.723 | 8.2 |
| 25.225 | 18.4 |
| 25.498 | 17.2 |
| 25.966 | 22.2 |
| 26.312 | 8.6 |
| 26.782 | 13.3 |
| 26.976 | 16.9 |
| 27.494 | 7.3 |
| 27.941 | 16.5 |
| 28.641 | 20.3 |
| 28.944 | 7.8 |
| 29.302 | 8.3 |
| 29.950 | 6.7 |
| 30.460 | 17.5 |
| 31.088 | 9.6 |
| 31.695 | 5.6 |
| 32.905 | 8.1 |
| 33.362 | 10.1 |
| 33.520 | 9.7 |
| 35.040 | 9.1 |
| 35.551 | 8.4 |
| 37.152 | 5.8 |
| 37.380 | 5.9 |
| 38.287 | 9.4 |
| 38.457 | 8.2 |
| 38.937 | 12.3 |
| 39.495 | 7.0 |
| 39.929 | 5.7 |
| 40.793 | 5.0 |
| 42.526 | 5.2 |
| 42.986 | 7.5 |
| 44.638 | 5.2 |
| 47.791 | 6.5 |

TABLE 3

Simulated PXRD Peak Data for the compound of Example 47

| 2-Theta ° | Intensity % |
|---|---|
| 6.859 | 22.5 |
| 8.823 | 8.9 |
| 10.277 | 16.1 |
| 10.516 | 14.9 |
| 11.541 | 22.6 |
| 12.802 | 8.5 |
| 13.851 | 4.3 |
| 14.260 | 7.8 |

TABLE 3-continued

Simulated PXRD Peak Data for the compound of Example 47

| 2-Theta ° | Intensity % |
|---|---|
| 16.418 | 27.4 |
| 16.950 | 74.0 |
| 17.688 | 6.5 |
| 18.377 | 11.3 |
| 18.881 | 34.0 |
| 19.342 | 100.0 |
| 19.860 | 16.4 |
| 20.644 | 19.4 |
| 21.281 | 23.6 |
| 21.586 | 14.9 |
| 21.860 | 5.7 |
| 22.672 | 29.7 |
| 23.179 | 5.4 |
| 23.522 | 16.1 |
| 24.906 | 12.7 |
| 25.259 | 5.1 |
| 25.602 | 4.0 |
| 27.245 | 4.7 |
| 28.000 | 4.8 |
| 28.431 | 23.0 |
| 28.913 | 12.3 |
| 29.552 | 13.4 |
| 31.333 | 8.5 |
| 32.057 | 4.3 |
| 32.221 | 4.4 |
| 32.685 | 7.8 |
| 33.593 | 8.4 |
| 33.792 | 6.7 |
| 34.511 | 6.6 |
| 36.022 | 6.5 |
| 36.456 | 7.1 |
| 39.229 | 5.7 |
| 45.114 | 5.2 |
| 51.277 | 4.2 |

TABLE 4

Simulated PXRD Peak Data for the compound of Example 48

| 2-Theta ° | Intensity % |
|---|---|
| 6.870 | 33.0 |
| 8.908 | 6.4 |
| 10.463 | 14.8 |
| 10.761 | 9.0 |
| 11.656 | 5.3 |
| 12.966 | 4.1 |
| 14.787 | 5.9 |
| 16.422 | 6.5 |
| 16.720 | 21.0 |
| 17.026 | 60.7 |
| 18.400 | 6.9 |
| 18.893 | 100.0 |
| 19.591 | 26.1 |
| 20.103 | 31.3 |
| 20.790 | 18.3 |
| 21.570 | 32.3 |
| 22.094 | 4.3 |
| 22.823 | 15.3 |
| 23.207 | 23.7 |
| 23.849 | 6.9 |
| 24.909 | 12.4 |
| 25.531 | 5.1 |
| 25.720 | 4.0 |
| 26.301 | 7.1 |
| 26.571 | 8.6 |
| 27.922 | 4.7 |
| 28.174 | 6.2 |
| 28.612 | 6.1 |
| 29.016 | 6.6 |

TABLE 4-continued

Simulated PXRD Peak Data for the compound of Example 48

| 2-Theta ° | Intensity % |
|---|---|
| 29.494 | 6.9 |
| 30.387 | 13.3 |
| 30.642 | 9.6 |
| 31.231 | 4.4 |
| 31.551 | 7.2 |
| 32.016 | 6.8 |
| 32.824 | 4.4 |
| 33.478 | 6.4 |
| 34.280 | 4.7 |
| 34.483 | 7.2 |
| 34.750 | 5.6 |
| 37.504 | 6.1 |
| 39.705 | 5.2 |
| 42.797 | 5.2 |
| 43.416 | 4.5 |

TABLE 5

Simulated PXRD Peak Data for the compound of Example 49

| 2-Theta ° | Intensity % |
|---|---|
| 6.842 | 41.9 |
| 10.061 | 32.0 |
| 10.637 | 41.0 |
| 11.082 | 23.9 |
| 13.212 | 9.4 |
| 13.772 | 10.3 |
| 15.818 | 11.1 |
| 16.640 | 14.3 |
| 17.233 | 74.4 |
| 17.583 | 44.5 |
| 17.812 | 42.4 |
| 18.426 | 42.3 |
| 18.824 | 100.0 |
| 19.352 | 15.7 |
| 19.648 | 24.3 |
| 20.053 | 87.5 |
| 20.736 | 38.1 |
| 21.016 | 20.3 |
| 21.233 | 19.4 |
| 21.616 | 47.3 |
| 22.707 | 24.8 |
| 23.300 | 29.6 |
| 23.500 | 20.9 |
| 23.920 | 9.3 |
| 24.060 | 12.5 |
| 24.680 | 10.6 |
| 25.651 | 16.6 |
| 25.990 | 17.8 |
| 26.613 | 8.9 |
| 27.052 | 19.3 |
| 27.171 | 16.9 |
| 27.442 | 6.3 |
| 28.073 | 13.4 |
| 28.661 | 27.1 |
| 29.231 | 10.5 |
| 29.941 | 7.2 |
| 30.155 | 5.8 |
| 30.568 | 11.8 |
| 30.740 | 7.3 |
| 31.177 | 7.6 |
| 31.761 | 7.1 |
| 33.104 | 6.3 |
| 33.450 | 9.7 |
| 33.894 | 6.7 |
| 35.038 | 5.6 |
| 35.373 | 5.7 |
| 35.603 | 10.1 |
| 37.352 | 7.1 |

TABLE 5-continued

Simulated PXRD Peak Data for the compound of Example 49

| 2-Theta ° | Intensity % |
|---|---|
| 38.531 | 5.9 |
| 38.843 | 8.6 |
| 39.387 | 5.1 |
| 39.766 | 7.4 |
| 39.971 | 7.3 |
| 40.734 | 5.5 |
| 43.118 | 7.1 |
| 45.533 | 5.3 |
| 46.554 | 6.6 |
| 51.453 | 5.3 |

What is claimed is:

1. A compound of formula (I)

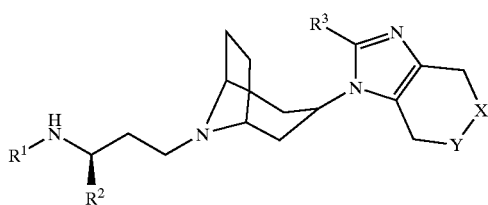

(I)

or a pharmaceutically acceptable salt or solvate thereof wherein:

X and Y are selected from $CH_2$ and $NR^4$ such that one of X and Y is $CH_2$ and the other is $NR^4$;

$R^1$ and $R^4$ are independently $R^5$; $COR^5$; $CO_2R^5$; $CONR^6R^7$; $SO_2R^5$; or ($C_{1-6}$ alkylene)phenyl, wherein phenyl is substituted by 0 to 3 atoms or groups selected from $C_{1-6}$ alkyl, $C_{1-6}$ alkylcarbonyl, $C_{1-6}$ alkoxy, $C_{1-6}$ alkoxycarbonyl, halogen, $CF_3$, OH, CN, $NR^6R^7$, $COR^7$, $CO_2R^7$ or $CONR^6R^7$;

$R^2$ is phenyl substituted by 0 to 3 atoms or groups selected from $C_{1-6}$ alkyl, $C_{1-6}$ alkylcarbonyl, $C_{1-6}$ alkoxy, $C_{1-6}$ alkoxycarbonyl, halogen, $CF_3$, OH, CN, $NR^6R^7$, $CO_2R^7$ or $CONR^6R^7$;

$R^3$ is $C_{1-4}$ alkyl substituted by 0 to 3 fluorine atoms;

$R^5$ is $C_{1-6}$ alkyl; $C_{2-6}$ alkenyl; $C_{2-6}$ alkynyl; $C_{3-7}$ cycloalkyl; a 5 or 6-membered aromatic heterocycle; or a 4 to 7-membered saturated heterocycle; wherein said alkyl, alkenyl, alkynyl and cycloalkyl are substituted by 0 to 3 atoms or groups selected from oxo, halogen, $CF_3$, $OR^7$, CN, $NR^6R^7$, $COR^7$, $CO_2R^7$ or $CONR^6R^7$; wherein said heterocycles contain one to three heteroatoms selected from N, O or S; and wherein said heterocycles are substituted by 0 to 3 atoms or groups selected from $C_{1-6}$ alkyl, $C_{1-6}$ alkylcarbonyl, $C_{1-6}$ alkoxy, $C_{1-6}$ alkoxycarbonyl, halogen, $CF_3$, OH, CN, $NR^6R^7$, $COR^7$, $CO_2R^7$ or $CONR^6R^7$;

$R^6$ is H; $C_{1-6}$ alkyl; $C_{2-6}$ alkenyl; $C_{2-6}$ alkynyl; $C_{3-7}$ cycloalkyl; a 5 or 6-membered aromatic heterocycle; or a 4 to 7-membered saturated heterocycle; wherein said alkyl, alkenyl, alkynyl and cycloalkyl are substituted by 0 to 3 atoms or groups selected from oxo, halogen, $CF_3$, $OR^7$, CN, $COR^7$ or $CO_2R^7$; wherein said heterocycles contain one to three heteroatoms selected from N, O or S; and wherein said heterocycles are substituted by 0 to 3 atoms or groups selected from $C_{1-6}$ alkyl, $C_{1-6}$ alkylcarbonyl, $C_{1-6}$ alkoxy, $C_{1-6}$ alkoxycarbonyl, halogen, $CF_3$, OH, CN, $COR^7$ or $CO_2R^7$;

$R^7$ is H or $C_{1-6}$ alkyl;

or, when $R^6$ and $R^7$ are both attached to the same N atom, $NR^5R^7$ may also represent a 5 to 7 membered, saturated, partially unsaturated or aromatic, heterocycle containing from 0 to 2 additional heteroatoms selected from O, N or S.

2. A compound as defined in claim 1 wherein X is $CH_2$, $NC_{1-4}$ alkyl, $NCH_2$phenyl, $NCOC_{1-4}$ alkyl substituted by 0 to 3 fluorine atoms, $NCO_2C_{1-4}$ alkyl or $NSO_2C_{1-2}$ alkyl.

3. A compound as defined in claim 1 wherein X is $CH_2$, $NCOC_{1-2}$ alkyl substituted by 0 to 3 fluorine atoms or $NCO_2C_{1-4}$ alkyl.

4. A compound as defined in claim 1 wherein X is $CH_2$, $NCOC_{1-2}$ alkyl or $NCO_2C_{1-2}$ alkyl.

5. A compound as defined in claim 1 wherein Y is $CH_2$, $NC_{1-6}$ alkyl, $N(C_{1-6}$ alkylene)phenyl, $NCOC_{1-6}$ alkyl substituted by 0 to 3 fluorine atoms, $NCO_2C_{1-6}$ alkyl or $NSO_2C_{1-6}$ alkyl.

6. A compound as defined in claim 1 wherein Y is $CH_2$, $NC_{1-4}$ alkyl, $N(C_{1-4}$ alkylene)phenyl, $NCOC_{1-4}$ alkyl substituted by 0 to 3 fluorine atoms, $NCO_2C_{1-4}$ alkyl or $NSO_2C_{1-4}$ alkyl.

7. A compound as defined in claim 1 wherein Y is $CH_2$, $NC_{1-4}$ alkyl, $NCH_2$phenyl, $NCOC_{1-4}$ alkyl substituted by 0 or 3 fluorine atoms, $NCO_2C_{1-4}$ alkyl or $NSO_2C_{1-2}$ alkyl.

8. A compound as defined in claim 1 wherein Y is $CH_2$, $NCOC_{1-2}$ alkyl, or $NCO_2C_{1-2}$ alkyl.

9. A compound as defined in claim 1 wherein $R^1$ is $COR^5$ or $CO_2R^5$ and $R^5$ is $C_{1-6}$ alkyl substituted by 0 to 3 fluorine atoms, $C_{3-7}$ cycloalkyl substituted by 0 to 3 fluorine atoms, $C_{1-6}$ alkoxy substituted by 0 to 3 fluorine atoms, or a 4- to 7-membered saturated heterocycle containing 1 to 3 heteroatoms selected from N, O or S.

10. A compound as defined in claim 1 wherein $R^1$ is $COR^5$ or $CO_2R^5$, wherein $R^5$ is $C_{1-4}$ alkyl substituted by 0 to 3 fluorine atoms, $C_{3-5}$ cycloalkyl substituted by 0 to 3 fluorine atoms, or a 5- or 6-membered, N-, O-, or S- containing, saturated heterocycle.

11. A compound as defined in claim 1 wherein $R^1$ is $COR^5$ or $CO_2R^5$ and $R^5$ is $C_{1-3}$ alkyl substituted by 0 or 3 fluorine atoms, $C_{3-4}$ cycloalkyl, or a 5- or 6-membered, O-containing, saturated heterocycle.

12. A compound as defined in claim 1 wherein $R^1$ is $COC_{1-2}$ alkyl or $CO_2C_{1-2}$ alkyl.

13. A compound as defined in claim 1 wherein $R^2$ is phenyl substituted by 0 or 3 fluorine atoms.

14. A compound as defined in claim 1 wherein $R^2$ is phenyl substituted by 0 or 1 fluorine atoms.

15. A compound as defined in claim 1 wherein $R^2$ is mono-fluoro-substituted phenyl.

16. A compound as defined in claim 1 wherein $R^3$ is $C_{1-4}$ alkyl.

17. A compound as defined in claim 1 wherein $R^3$ is methyl.

18. A pharmaceutical composition comprising a compound of the formula (I) or a pharmaceutically acceptable salt or solvate thereof together with one or more pharmaceutically acceptable excipients, diluents or carriers.

19. A method of treating a disorder in which the antagonism of CCR5 receptors is implicated comprising administering to a mammal in need thereof a therapeutically effective amount of a compound of the formula (1) of claim 1 or a pharmaceutically acceptable salt or solvate thereof wherein the disorder is HIV infection or an inflammatory disease.

20. A method of treatment of a mammal suffering from a disorder in which the antagonism of CCR5 receptors is implicated which comprises treating said mammal with an effective amount of a pharmaceutical composition of claim 18, wherein the disorder is HIV infection or an inflammatory disease.

* * * * *